(12) United States Patent
Badiger et al.

(10) Patent No.: US 8,637,508 B2
(45) Date of Patent: Jan. 28, 2014

(54) HETEROCYCLIC DERIVATIVES AND THEIR USE IN THE TREATMENT OF NEUROLOGICAL DISORDERS

(75) Inventors: Sangamesh Badiger, Karnataka (IN); Murali Chebrolu, Andhra Pradesh (IN); Konstanze Hurth, Loerrach (DE); Sébastien Jacquier, Hegenheim (FR); Rainer Martin Lueoend, Therwil (CH); Rainer Machauer, Freiburg (DE); Heinrich Rueeger, Flueh (CH); Marina Tintelnot-Blomley, Maulburg (DE); Siem Jacob Veenstra, Loerrach (DE); Markus Voegtle, Loerrach (DE)

(73) Assignee: Novartis AG, Basel (CH)

( * ) Notice: Subject to any disclaimer, the term of this patent is extended or adjusted under 35 U.S.C. 154(b) by 28 days.

(21) Appl. No.: 13/348,039

(22) Filed: Jan. 11, 2012

(65) Prior Publication Data

US 2012/0184539 A1 Jul. 19, 2012

Related U.S. Application Data

(60) Provisional application No. 61/534,591, filed on Sep. 14, 2011.

(30) Foreign Application Priority Data

Jan. 13, 2011 (IN) .............................. 77/DEL/2011

(51) Int. Cl.
   A61K 31/5377 (2006.01)
   C07D 413/14 (2006.01)
(52) U.S. Cl.
   CPC .................................. C07D 413/14 (2013.01)
   USPC .................. 514/233.8; 514/234.2; 514/235.8; 514/236.5; 544/120; 544/131
(58) Field of Classification Search
   CPC ................................................... C07D 413/14
   USPC ..................... 514/233.8, 234.2, 236.5, 235.8; 544/120, 131
   See application file for complete search history.

(56) References Cited

U.S. PATENT DOCUMENTS

| | | | |
|---|---|---|---|
| 5,691,336 | A | 11/1997 | Dorn et al. |
| 7,642,272 | B2 | 1/2010 | Shankar et al. |
| 7,745,438 | B2 | 6/2010 | Broughton et al. |
| 7,888,374 | B2 | 2/2011 | Liu et al. |
| 8,207,164 | B2 | 6/2012 | Holzer et al. |
| 8,338,413 | B1 | 12/2012 | Rueeger |
| 8,524,897 | B2 | 9/2013 | Ramos |
| 2004/0186148 | A1 | 9/2004 | Shankar et al. |
| 2006/0173050 | A1 | 8/2006 | Liu et al. |
| 2007/0149547 | A1 | 6/2007 | Bonnefous et al. |
| 2007/0225267 | A1 | 9/2007 | Broughton |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0137336 | A1 | 6/2010 | Bolea |
| 2010/0197688 | A1 | 8/2010 | Nantermet et al. |
| 2011/0021520 | A1 | 1/2011 | Badiger et al. |
| 2011/0190279 | A1 | 8/2011 | Hori et al. |
| 2011/0237576 | A1 | 9/2011 | Yonesawa et al. |
| 2012/0172359 | A1 | 7/2012 | Veenstra et al. |
| 2012/0178745 | A1 | 7/2012 | Ramos |
| 2012/0184539 | A1 | 7/2012 | Badiger |

FOREIGN PATENT DOCUMENTS

| | | |
|---|---|---|
| EP | 1942105 | 7/2008 |
| EP | 2151435 | 2/2010 |
| EP | 2360155 | 8/2011 |
| WO | 2005/079802 | 9/2005 |
| WO | 2006/034093 | 3/2006 |
| WO | 2007/049532 | 3/2007 |
| WO | 2008/106692 | 9/2008 |
| WO | 2008/133273 | 11/2008 |
| WO | 2008/133274 | 11/2008 |
| WO | 2009/010454 | 1/2009 |
| WO | 2009/091016 | 7/2009 |
| WO | 2009/151098 | 12/2009 |
| WO | 2010/007756 | 1/2010 |
| WO | 2010/047372 | 4/2010 |
| WO | 2010/070502 | 6/2010 |
| WO | 2010/128058 | 11/2010 |
| WO | 2011/009943 | 1/2011 |
| WO | 2011/020806 | 2/2011 |

(Continued)

OTHER PUBLICATIONS

AlzheimersClinicalTrials, 2012, http://www.nature.com/nm/journal/v17/n8/full/nm0811-932.html.
Tacrine, 2012, http://en.wikipedia.org/wiki/Tacrine.
Patani et al., Bioisosterism: A Rational Approach in Drug Design, Chem. Rev., 96:3147-3176 (1996).
AlzheimersCure, 2012, http://www.alz.org/alzheimers_disease_treatments.asp.
AlzheimersCure, 2012, http://www.alz.org/research/science/alzheimers_prevention_and_risk.asp.
AlzheimersDrugs, 2012, http://www.alz.org/research/science/alzheimers_disease_treatments.asp.

(Continued)

*Primary Examiner* — Rebecca Anderson
(74) *Attorney, Agent, or Firm* — Joshua Roth

(57) ABSTRACT

The invention relates to novel heterocyclic compounds of the formula

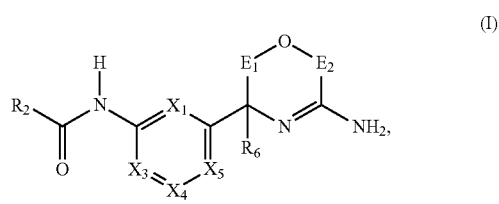

(I)

in which all of the variables are as defined in the specification, pharmaceutical compositions thereof, combinations thereof, and their use as medicaments, particularly for the treatment of Alzheimer's Disease or diabetes via inhibition of BACE-1 or BACE-2.

25 Claims, No Drawings

(56) References Cited

FOREIGN PATENT DOCUMENTS

| | | |
|---|---|---|
| WO | 2011/058763 | 5/2011 |
| WO | 2011/069934 | 6/2011 |
| WO | 2011/070029 | 6/2011 |
| WO | 2011/071135 | 6/2011 |
| WO | 2011/077726 | 6/2011 |
| WO | 2011/080176 | 7/2011 |
| WO | 2011/138293 | 11/2011 |
| WO | 2011/154374 A1 | 12/2011 |
| WO | 2011/154431 A1 | 12/2011 |
| WO | 2012/006953 A1 | 1/2012 |
| WO | 2012/095463 | 7/2012 |
| WO | 2012/095521 | 7/2012 |
| WO | 2012/129258 | 9/2012 |
| WO | 2013/054291 | 4/2013 |

OTHER PUBLICATIONS

Donezepil, 2012, http://en.wikipedia.org/wiki/Donepezil.
Galantamine, 2012, http://en.wikipedia.orgiwiki/Galantamine.
Memantine, 2012, http://en.wikipedia.orgiwiki/Memantine.
Rivastigmine, 2012, http://en.wikipedia.org/wiki/Rivastigmine.
Rueeger, H., Presenatation at FMC Saarbrucken "Structure and Property Based Design of Cyclic Hydroxyethylamine BACE-1 Inhibitors", Mar. 23, 2011.
U.S. Appl. No. 13/347,067 "Novel Crystalline Oxazine Derivative" filed in the name of Novartis AG on Jan. 10, 2012.
U.S. Appl. No. 13/414,440 "Oxazine Derivatives and their Use in the Treatment of Neurological Disorders" filed in the name of Novartis AG on Apr. 4, 2012.
U.S. Appl. No. 13/414,483 "Oxazine Derivatives and their Use in the Treatment of Neurological Disorders" filed in the name of Novartis AG on Apr. 4, 2012.

HETEROCYCLIC DERIVATIVES AND THEIR USE IN THE TREATMENT OF NEUROLOGICAL DISORDERS

FIELD OF THE INVENTION

The invention relates to novel heterocyclic derivatives and pharmaceutically acceptable salts thereof, pharmaceutical compositions thereof, pharmaceutical combinations thereof, and their use as medicaments, particularly for the treatment of neurodegeneration via inhibition of BACE-1 or diabetes via inhibition of BACE-2.

BACKGROUND OF THE INVENTION

Alzheimer's Disease is a devastating neurodegenerative disorder. Its sporadic forms affect an elderly population (sharp increase in incidence at >75 years of age), in addition, there are various familial forms with an onset of the disease in the fourth or fifth decade of life. Pathologically, it is characterized by the presence of extracellular senile plaques, and intracellular neurofibrillar tangles in patient's brains. The core constituent of the senile plaques are small, 4 kDa amyloid peptides. They are generated by the proteolytic processing of a large transmembrane protein, amyloid precursor protein (APP). Cleavage of APP by beta-secretase (BACE-1) releases the soluble APP-beta fragment, while the 99-amino acid long C-terminus remains tethered to the membrane. This C-terminal fragment is subsequently proteolytically processed by gamma-secretase (a membrane multi-enzyme complex) to generate amyloid peptides of various length, predominantly 40 and 42 amino acids long (Hardy J, Selkoe D J (2002) Science; 297 (5580):353-356).

If, under pathologic conditions, the generation of these peptides occurs at an increased rate, or if their removal from the brain is disturbed, increased brain amyloid peptide concentrations leads to the formation of oligomers, fibrils and eventually plaques (Farris W, et al (2007) Am. J. Pathol.; 171(1):241-251). It has been shown, that deposition of amyloid peptides and plaques in the brain is the first measurable event in the pathogenesis of Alzheimers Disease, and that it is the trigger for loss of synapses, synaptic contacts, and neurons (Grimmer T, et al (2009) Neurobiology of Aging; 30 (12):1902-1909). Brain atrophy caused by massive neuron loss is followed by impairments in cognition, memory, orientation and the ability to perform the tasks of daily living, i.e. clinically manifest dementia (Okello A, et al (2009) Neurology; 73 (10):754-760).

BACE-1, also known as Asp2 or Memapsin 2, is a transmembrane aspartic protease highly expressed in neurons. It co-localizes with its substrate APP in Golgi and endocytic compartments (Willem M, Lammich S, Haass C (2009) Semin. Cell Dev. Biol; 20 (2):175-182). Knock-out studies in mice have demonstrated the absence of amyloid peptide formation, while the animals are healthy and fertile (Ohno M, et al (2007) Neurobiol. Dis.; 26 (1):134-145). Genetic ablation of BACE-1 in APP-overexpressing mice has demonstrated absence of plaque formation and the reversal of cognitive deficits (Ohno M, et al (2004) Neuron; 41 (1):27-33). BACE-1 levels are elevated in the brains of sporadic Alzheimer's Disease patients (Hampel H, Shen Y (2009) Scand. J. Clin. Lab. Invest.; 69 (1):8-12).

Taken together, these findings suggest that the inhibition of BACE-1 may be a favourable therapeutic strategy for the treatment of Alzheimer's Disease.

Beta-site amyloid precursor protein cleaving enzyme 2 (BACE-2) is a transmembrane aspartic protease that is highly expressed in pancreatic β cells and other peripheral tissues (Brian D. Bennett, Safura Babu-Khan, Richard Loeloff, Jean-Claude Louis, Eileen Curran; Martin Citron, and Robert Vassar (2000) JJ. Biol. Chem. 275 (27) 20647-20651). BACE-2 is closely related to BACE-1 or beta secretase. However, despite structural and sequence similarities the substrate specificity of BACE-1 and BACE-2 appear to be different. While Aβ or β-amyloid peptide is the main substrate of BACE-1, BACE-2 does not generate either form of Aβ (Vassar, R., Bennett, B. D., Babu-Khan, S., Kahn, S., Mendiaz, E. A., Denis, P., Teplow, D. B., Ross, S., Amarante, P., Loeloff, R., Luo, Y., Fisher, S., Fuller, J., Edenson, S., Lile, J., Jarosinski, M. A., Biere, A. L., Curran, E., Burgess, T., Louis, J.-C., Collins, F., Treanor, J., Rogers, G., and Citron, M. (1999) Science 286, 735-741).

Transmembrane protein 27 (TMEM27 or collectrin) plays an important role in 6-cell proliferation and insulin secretion (Pinar Akpinar, Satoru Kuwajima, Jan Krützfeldt, and Markus Stoffel (2005) Tmem27: Cell Metabolism. 2(6) 385-397) and has been identified as a substrate for BACE-2 (WO 2010/063718). Tmem27 exists as a dimer and the extracellular domain is cleaved and shed from the plasma in a β cell-specific manner. Overexpression of full-length Tmem27, but not the truncated or soluble protein, increases β cell proliferation, suggesting that the full length protein is required for this biological function. Tcf1 (hepatocyte nuclear factor-1α, HNF-1α) controls the transcription of TMEM27. Mice with targeted deletion of Tcf1 exhibit decreased β cell mass, and knockdown of Tmem27 using RNAi results in a reduction of cell proliferation. Transgenic mice with increased expression of Tmem27 in pancreatic β cells exhibit increased β cell mass compared to their wild-type littermates. This data indicates that TMEM27 plays a role in control of β cell mass and that inhibition of BACE-2 which cleaves TMEM27 could be useful for treating loss of β cell mass and function, the underlying cause of diabetes.

Taken together, these findings suggest that the inhibition of BACE-2 may be a favourable therapeutic strategy for the treatment and prevention of metabolic disorders related to decreased β cell mass and/or function, such as type 2 diabetes.

SUMMARY OF THE INVENTION

The present invention relates to novel heterocyclic derivatives having BACE inhibitory activity, to their preparation, to their medical use and to medicaments comprising them.

More particularly, in a first aspect, the invention relates to a compound of the formula

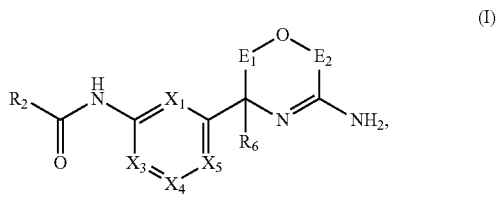

in which
either
$X_1$ is $CR_1$, or N;
$X_3$ is $CR_3$ or N;
$X_4$ is $CR_4$ or N;
$X_5$ is $CR_5$ or N;
wherein at least one of $X_1$, $X_3$, $X_4$ and $X_5$ is N and not more than 2 of $X_1$, $X_3$, $X_4$ and $X_5$ are N;

or $X_1$ is $CR_1$, or N;

$X_3$ is $CR_3$, N or S;

$X_4$ is a bond;

$X_5$ is $CR_5$, N or S;

wherein at least one of $X_1$, $X_3$ and $X_5$ is N or S, not more than 2 of $X_1$, $X_3$ and $X_5$ are N and not more than 1 of $X_3$ and $X_5$ are S;

$R_1$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_2$ is an aryl, heteroaryl or non-aromatic heterocyclyl group $G_1$, which group $G_1$ is optionally substituted by 1, 2, 3 or 4 substituents independently selected from the group, consisting of cyano, amino, amino-$(C_{1-8})$alkyl, N—$(C_{1-4})$alkyl-amino-$(C_{1-8})$alkyl, N,N-di$(C_{1-4})$alkyl-amino-$(C_{1-8})$alkyl, aminocarbonyl, thiocarbamoyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{3-8})$cycloalkyl-$(C_{1-8})$alkoxy, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3, or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

$R_3$ is hydrogen, cyano, halogen, $(C_{1-8})$alkyl, halogen-$(C_{1-8})$alkyl, $(C_{1-8})$alkoxy; halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_4$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_5$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

or $R_4$ and $R_5$, taken together, are —C(H)═C(H)—C(H)═C(H)— or a $(C_{1-8})$alkylene group, in which $(C_{1-8})$alkylene group 1 or 2 —CH$_2$— ring members are optionally replaced with hetero ring members independently selected from the group, consisting of —N(H)—, —N[$(C_{1-8})$alkyl]-, —O—, —S—, —S(═O)— or —S(═O)$_2$—;

$R_6$ is $(C_{1-8})$alkyl, halogen-$(C_{1-8})$alkyl, hydroxy-$(C_{1-8})$alkyl, $(C_{1-8})$alkoxy-$(C_{1-8})$alkyl, mercapto-$(C_{1-8})$alkyl, $(C_{1-8})$alkylthio-$(C_{1-8})$alkyl, amino-$(C_{1-8})$alkyl, N—$(C_{1-4})$alkyl-amino-$(C_{1-8})$alkyl, N,N-di$(C_{1-4})$alkyl-amino-$(C_{1-8})$alkyl, $(C_{2-8})$alkenyl, or $(C_{2-8})$alkynyl;

or $R_5$ and $R_6$, taken together, are a $(C_{1-4})$alkylene group, in which $(C_{1-4})$alkylene group 1 —CH$_2$— ring member is optionally replaced with a hetero ring member independently selected from the group, consisting of —N(H)—, —N[$(C_{1-4})$alkyl]-, —O—, —S—, —S(═O)— or —S(═O)$_2$—;

$E_1$ is —C($R_7$)($R_8$)—, or —C($R_7$)($R_8$)—C($R_9$)($R_{10}$)—;

$E_2$ is —C($R_{11}$)($R_{12}$)—, or —C($R_{11}$)($R_{12}$)—C($R_{13}$)($R_{14}$)—;

either each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_7$ and $R_8$, taken together, are oxo or —CH$_2$—CH$_2$—;

either each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_9$ and $R_{10}$, taken together, are oxo or —CH$_2$—CH$_2$—;

either each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl; or $R_{11}$ and $R_{12}$, taken together, are oxo or —CR$_{15}$R$_{16}$—CR$_{17}$R$_{18}$— wherein $R_{15}$, $R_{16}$, $R_{17}$ and $R_{18}$ are independently selected from hydrogen and fluoro;

and either each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_{13}$ and $R_{14}$, taken together, are oxo or —CH$_2$—CH$_2$—;

or a pharmaceutically acceptable salt thereof.

In a second aspect, the invention relates to a compound of the formula

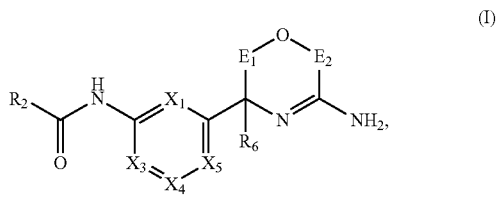

(I)

in which either $X_1$ is $CR_1$, or N;

$X_3$ is $CR_3$ or N;

$X_4$ is $CR_4$ or N;
$X_5$ is $CR_5$ or N;
wherein at least one of $X_1$, $X_3$, $X_4$ and $X_5$ is N and not more than 2 of $X_1$, $X_3$, $X_4$ and $X_5$ are N;

or $X_1$ is $CR_1$, or N;
$X_3$ is $CR_3$, N or S;
$X_4$ is a bond;
$X_5$ is $CR_5$, N or S;
wherein at least one of $X_1$, $X_3$ and $X_5$ is N or S, not more than 2 of $X_1$, $X_3$ and $X_5$ are N and not more than 1 of $X_3$ and $X_5$ are S;

$R_1$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_2$ is an aryl, heteroaryl or non-aromatic heterocyclyl group $G_1$, which group $G_1$ is optionally substituted by 1, 2, 3 or 4 substituents independently selected from the group, consisting of cyano, amino, amino-$(C_{1-8})$alkyl, N—$(C_{1-4})$alkyl-amino-$(C_{1-8})$alkyl, N,N-di$(C_{1-4})$alkyl-amino-$(C_{1-8})$alkyl, aminocarbonyl, thiocarbamoyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{3-8})$cycloalkyl-$(C_{1-8})$alkoxy, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3, or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

$R_3$ is hydrogen, cyano, halogen, $(C_{1-8})$alkyl, halogen-$(C_{1-8})$alkyl, $(C_{1-8})$alkoxy; halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_4$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_5$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

or $R_4$ and $R_5$, taken together, are —C(H)=C(H)—C(H)=C(H)— or a $(C_{1-8})$alkylene group, in which $(C_{1-8})$alkylene group 1 or 2 —$CH_2$— ring members are optionally replaced with hetero ring members independently selected from the group, consisting of —N(H)—, —N[$(C_{1-8})$alkyl]-, —O—, —S—, —S(=O)— or —S(=O)$_2$—;

$R_6$ is hydrogen, $(C_{1-8})$alkyl, halogen-$(C_{1-8})$alkyl, hydroxy-$(C_{1-8})$alkyl, $(C_{1-8})$alkoxy-$(C_{1-8})$alkyl, mercapto-$(C_{1-8})$alkyl, $(C_{1-8})$alkylthio-$(C_{1-8})$alkyl, amino-$(C_{1-8})$alkyl, N—$(C_{1-4})$alkyl-amino-$(C_{1-8})$alkyl, N,N-di$(C_{1-4})$alkyl-amino-$(C_{1-8})$alkyl, $(C_{2-8})$alkenyl, or $(C_{2-8})$alkynyl;

or $R_5$ and $R_6$, taken together, are a $(C_{1-4})$alkylene group, in which $(C_{1-4})$alkylene group 1 —$CH_2$— ring member is optionally replaced with a hetero ring member independently selected from the group, consisting of —N(H)—, —N[$(C_{1-4})$alkyl]-, —O—, —S—, —S(=O)— or —S(=O)$_2$—;

$E_1$ is —C($R_7$)($R_8$)—, or —C($R_7$)($R_8$)—C($R_9$)($R_{10}$)—;
$E_2$ is —C($R_{11}$)($R_{12}$)—, or —C($R_{11}$)($R_{12}$)—C($R_{13}$)($R_{14}$)—;

either
each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_7$ and $R_8$, taken together, are oxo or —$CH_2$—$CH_2$—;
either
each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_8$ and $R_{10}$, taken together, are oxo or —$CH_2$—$CH_2$—;
either
each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_{11}$ and $R_{12}$, taken together, are oxo or —$CR_{15}R_{16}$—$CR_{17}R_{18}$—
wherein $R_{15}$, $R_{16}$, $R_{17}$ and $R_{18}$ are independently selected from hydrogen and fluoro;

and
either
each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_{13}$ and $R_{14}$, taken together, are oxo or —$CH_2$—$CH_2$—;
or a pharmaceutically acceptable salt thereof.

DEFINITIONS

Halogen denotes fluorine, chlorine, bromine or iodine.
A halogenated group or moiety, such as halogenalkyl, can be mono-, di-, tri-, poly- or per-halogenated.
An aryl group, ring or moiety is a naphthyl or phenyl group, ring or moiety.
A heteroaryl group, ring or moiety is a monocyclic aromatic 5- or 6-membered structure, in which structure 1, 2, 3 or 4 ring members are hetero ring members independently selected from the group, consisting of a nitrogen ring member, an oxygen ring member and a sulfur ring member, such as furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl; or a bicyclic aromatic 9- or 10- or membered structure, in which structure 1, 2, 3, 4 or 5 ring members are hetero ring members independently selected from the group, consisting of a nitrogen ring member, an oxygen ring member and a sulfur ring member. The fused rings completing the bicyclic groups may contain only carbon atoms and may be saturated, partially saturated, or unsaturated. Heteroaryl groups which are bicyclic include at least one fully aromatic ring but the other fused ring may be aromatic or non-aromatic. Examples of bicyclic heteroaryl groups include, benzofuranyl, benzothiophenyl, imidazopyridinyl, indazolyl, indolyl, isoquinolinyl, pyrazolopyridinyl, quinolinyl, pyrrolopyrazinyl (in particular pyrrolo[2,3-b]pyrazinyl) and pyrrolopyridinyl (in particular pyrrolo[3,2-b]pyridinyl). The heteroaryl radical may be bonded via a carbon atom or heteroatom.

A non-aromatic heterocyclyl group, ring or moiety is a non-aromatic 4-, 5-, 6- or 7-membered cyclic structure, in which structure 1, 2 or 3 ring members are hetero ring members independently selected from the group, consisting of a nitrogen ring member, an oxygen ring member and a sulfur ring member, such as azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

Any non-cyclic carbon containing group or moiety with more than 1 carbon atom is straight-chain or branched.

The terms "alkoxy", "alkenoxy" and "alkynoxy" respectively denote alkyl, alkenyl and alkynyl groups when linked by oxygen.

A "N,N-di($C_{1-4}$)alkyl-amino-($C_{1-8}$)alkyl" group may contain two identical or two different ($C_{1-4}$) moieties.

DETAILED DESCRIPTION OF THE INVENTION

The present invention provides compounds of formula (I) as defined hereinbefore and pharmaceutical compositions thereof that may be useful in the treatment or prevention of diseases, conditions and/or disorders modulated by BACE inhibition.

On account of one or more than one asymmetrical carbon atom, which may be present in a compound of the formula I, a corresponding compound of the formula I may exist in pure optically active form or in the form of a mixture of optical isomers, e.g. in the form of a racemic mixture. All of such pure optical isomers and all of their mixtures, including the racemic mixtures, are part of the present invention.

In one embodiment, the invention therefore relates to a compound of the formula

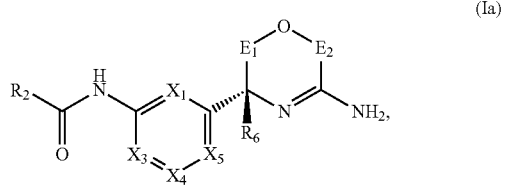

(Ia)

in which
$E_1$, $E_2$, $R_2$, $R_6$, $X_1$, $X_3$, $X_4$ and $X_5$ are as defined hereinbefore in relation to the formula I, or a pharmaceutically acceptable salt thereof.

In one embodiment, the invention therefore relates to a compound of the formula

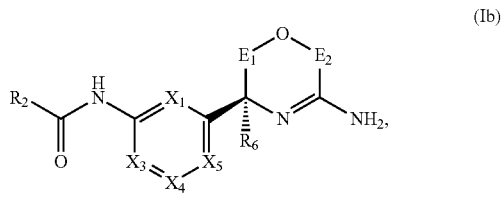

(Ib)

in which
$E_1$, $E_2$, $R_2$, $R_6$, $X_1$, $X_3$, $X_4$ and $X_5$ are as defined hereinbefore in relation to the formula I, or a pharmaceutically acceptable salt thereof.

In one embodiment, there is provided a compound of the Examples as an isolated stereoisomer wherein the compound has one stereocenter and the stereoisomer is in the R configuration.

In one embodiment, there is provided a compound of the Examples as an isolated stereoisomer wherein the compound has one stereocenter and the stereoisomer is in the S configuration.

In one embodiment, there is provided a compound of the Examples as an isolated stereoisomer wherein the compound has two stereocenters and the stereoisomer is in the R R configuration.

In one embodiment, there is provided a compound of the Examples as an isolated stereoisomer wherein the compound has two stereocenters and the stereoisomer is in the R S configuration.

In one embodiment, there is provided a compound of the Examples as an isolated stereoisomer wherein the compound has two stereocenters and the stereoisomer is in the S R configuration.

In one embodiment, there is provided a compound of the Examples as an isolated stereoisomer wherein the compound has two stereocenters and the stereoisomer is in the S S configuration.

In one embodiment, there is provided a compound of the Examples, wherein the compound has one or two stereocenters, as a racemic mixture.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

A compound of the formula I may exist in tautomeric form. All such tautomers are part of the present invention.

A compound of the formula I may exist in free form or in salt form, for example a basic compound in acid addition salt form or an acidic compound in the form of a salt with a base. All of such free compounds and salts are part of the present invention.

In one embodiment, the invention relates to a compound of the formula I, Ia, Ib, Ic, Id or Ie in free form. In another embodiment, the invention relates to a compound of the formula I, Ia, Ib, Ic, Id or Ie as defined herein, in salt form. In another embodiment, the invention relates to a compound of the formula I, Ia, Ib, Ic, Id or Ie as defined herein, in acid addition salt form. In a further embodiment, the invention relates to a compound of the formula I, Ia, Ib, Ic, Id or Ie as defined herein, in pharmaceutically acceptable salt form. In yet a further embodiment, the invention relates to a compound of the formula I, Ia, Ib, Ic, Id or Ie as defined herein, in hydrochloride salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form. In yet a further embodiment, the invention relates to any one of the compounds of the Examples in hydrochloride salt form.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid and sulfosalicylic acid. Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines and basic ion exchange resins. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs. All such polymorphs are part of the present invention.

The present invention includes all pharmaceutically acceptable isotope-labeled compounds of the formula I, wherein one or more than one atom is/are replaced by one or more than one atom having the same atomic number as, but an atomic mass different from, the one(s) usually found in nature. Examples of such isotopes are those of carbon, such as $^{11}C$, $^{13}C$ or chlorine, such as $^{36}Cl$, fluorine, such as $^{18}F$, bromine, such as $^{76}$Br, hydrogen, such as $^2$H or $^3$H, iodine, such as $^{123}$I, $^{124}$I, $^{125}$I, or $^{131}$I, nitrogen, such as $^{13}$N or $^{15}$N, oxygen, such as $^{15}$O, $^{17}$O or $^{18}$O, phosphorus, such as $^{32}$P, or sulphur, such as $^{35}$S. An isotope-labeled compound of the formula I can be prepared by a process analogous to those described in the Examples or by a conventional technique known to those skilled in the art using an appropriate isotopically-labeled reagent or starting material. The incorporation of a heavier isotope, such as $^2$H (deuterium or D), may provide greater metabolic stability to a compound of the formula I, which may result in, for example, an increased in vivo-half-life of the compound or in reduced dosage requirements. Certain isotope-labeled compounds of the formula I, for example those incorporating a radioactive isotope, such as $^3$H or $^{14}$C, may be used in drug or substrate-tissue distribution studies. Compounds of the formula I with a positron emitting isotope, such as $^{11}$C, $^{18}$F, $^{13}$N or $^{15}$O, may be useful in positron emission tomography (PET) or single photon emission computed tomography (SPECT) studies, e.g. to examine substrate-receptor occupancies.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I, Ia, Ib, Ic, Id or Ie that contain groups capable of acting as donors and/or acceptors for hydrogen bonds may be capable of forming co-crystals with suitable co-crystal formers. These co-crystals may be prepared from compounds of formula I, Ia, Ib, Ic, Id or Ie by known co-crystal forming procedures. Such procedures include grinding, heating, co-subliming, co-melting, or contacting in solution compounds of formula I, Ia, Ib, Ic, Id or Ie with the co-crystal former under crystallization conditions and isolating co-crystals thereby formed. Suitable co-crystal formers include those described in WO 2004/078163. Hence the invention further provides co-crystals comprising a compound of formula I, Ia, Ib, Ic, Id or Ie.

In certain embodiments, the invention relates to a compound of the formula I, Ia, Ib, Ic, Id or Ie, or a pharmaceutically acceptable salt thereof, in which:

(1) $X_1$ is $CR_1$ or N;
 $X_3$ is $CR_3$ or N;
 $X_4$ is $CR_4$ or N;
 $X_5$ is $CR_5$;
 wherein at least one of $X_1$, $X_3$ and $X_4$ is N and not more than 2 of $X_1$, $X_3$ and $X_4$ are N.
(2) $X_1$ is CH or N;
 $X_3$ is CH or N;
 $X_4$ is $CR_4$ or N;
 $X_5$ is $CR_5$;
 wherein one and not more than one of $X_1$, $X_3$ and $X_4$ is N;
(3) $X_1$ is N; $X_3$ is $CR_3$; $X_4$ is $CR_4$; and $X_5$ is $CR_5$.
(4) $X_1$ is $CR_1$; $X_3$ is N; $X_4$ is $CR_4$; and $X_5$ is $CR_5$.
(5) $X_1$ is $CR_1$; $X_3$ is $CR_3$; $X_4$ is N; and $X_5$ is $CR_5$.
(6) $X_1$ is $CR_1$; $X_3$ is $CR_3$; $X_4$ is $CR_4$; and $X_5$ is N.
(7) $X_1$ is N; $X_3$ is N; $X_4$ is $CR_4$; and $X_5$ is $CR_5$.
(8) $X_1$ is N; $X_3$ is $CR_3$; $X_4$ is N; and $X_5$ is $CR_5$.
(9) $X_1$ is N; $X_3$ is $CR_3$; $X_4$ is $CR_4$; and $X_5$ is N.
(10) $X_1$ is $CR_1$; $X_3$ is N; $X_4$ is N; and $X_5$ is $CR_5$.
(11) $X_1$ is $CR_1$; $X_3$ is N; $X_4$ is $CR_4$; and $X_5$ is N.
(12) $X_1$ is $CR_1$; $X_3$ is $CR_3$; $X_4$ is N; and $X_5$ is N.
(13) $R_1$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl.
(14) $R_1$ is hydrogen, cyano, halogen, $(C_{1-4})$alkyl, halogen-$(C_{1-4})$alkyl, $(C_{1-4})$alkoxy, or halogen-$(C_{1-4})$alkoxy.
(15) $R_1$ is hydrogen.
(16) $R_2$ is an aryl or heteroaryl group $G_1$, which group $G_1$ is optionally substituted by 1, 2, 3 or 4 substituents independently selected from the group, consisting of cyano, amino, amino-$(C_{1-6})$alkyl, $(C_{1-6})$alkyl-amino-$(C_{1-6})$alkyl, di$(C_{1-4})$alkyl-amino-$(C_{1-6})$alkyl, aminocarbonyl, thiocarbamoyl, halogen, $(C_{1-6})$alkyl, halogen-$(C_{1-6})$alkyl, hydroxy, oxo, $(C_{1-6})$alkoxy, halogen-$(C_{1-6})$alkoxy, $(C_{1-6})$alkylthio, halogen-$(C_{1-6})$alkylthio, $(C_{1-6})$alkoxy-$(C_{1-6})$alkyl, $(C_{3-6})$cycloalkyl-$(C_{1-6})$alkoxy, $(C_{1-6})$alkoxy-$(C_{1-6})$alkoxy, $(C_{1-6})$alkoxy-$(C_{1-6})$alkylthio, $(C_{1-6})$alkylthio-$(C_{1-6})$alkyl, $(C_{1-6})$alkylthio-$(C_{1-8})$alkoxy, $(C_{1-6})$alkylthio-$(C_{1-6})$alkylthio, $(C_{2-6})$alkenyl, $(C_{2-6})$alkynyl, $(C_{2-6})$alkenoxy, $(C_{2-6})$alkynoxy and a $(C_{3-6})$cycloalkyl, aryl, heteroaryl or non-aromatic heterocyclyl group $G_2$, which group $G_2$ is optionally substituted by 1 to 4 substituents independently selected from the group, consisting of cyano, aminocarbonyl, halogen, $(C_{1-6})$alkyl, halogen-$(C_{1-6})$alkyl, hydroxy, $(C_{1-6})$alkoxy, halogen-$(C_{1-6})$alkoxy, $(C_{1-6})$alkylthio, halogen-$(C_{1-6})$alkylthio, $(C_{1-6})$alkoxy-$(C_{1-6})$alkyl, $(C_{1-6})$alkoxy-$(C_{1-6})$alkoxy, $(C_{1-6})$alkoxy-$(C_{1-6})$alkylthio, $(C_{1-6})$alkylthio-$(C_{1-6})$alkyl, $(C_{1-6})$alkylthio-$(C_{1-6})$alkoxy, $(C_{1-6})$alkylthio-$(C_{1-6})$alkylthio, $(C_{2-6})$alkenyl and $(C_2$-6$)$alkynyl.
(17) $R_2$ is a heteroaryl group, which is optionally substituted by 1, 2, 3 or 4 substituents independently selected from the group, consisting of cyano, amino, amino-$(C_{1-6})$alkyl, $(C_{1-6})$alkyl-amino-$(C_{1-6})$alkyl, di$(C_{1-4})$alkyl-amino-$(C_{1-6})$alkyl, aminocarbonyl, thiocarbamoyl, halogen, $(C_{1-6})$alkyl, halogen-$(C_{1-6})$alkyl, hydroxy, oxo, $(C_{1-6})$alkoxy, halogen-$(C_{1-6})$alkoxy, $(C_1$-6$)$alkylthio, halogen-$(C_{1-6})$alkylthio, $(C_{1-6})$alkoxy-$(C_{1-6})$alkyl, $(C_{3-6})$cycloalkyl-$(C_{1-6})$alkoxy, $(C_{1-6})$alkoxy-$(C_{1-6})$alkoxy, $(C_{1-6})$alkoxy-$(C_{1-6})$alkylthio, $(C_{1-6})$alkylthio-$(C_{1-6})$alkyl, $(C_{1-6})$alkylthio-$(C_{1-6})$alkoxy, $(C_{1-6})$alkylthio-$(C_{1-6})$alkylthio, $(C_{2-6})$alkenyl, $(C_{2-6})$alkynyl, $(C_{2-6})$alkenoxy, $(C_2$-6$)$alkynoxy.
(18) $R_2$ is a 9- or 10- or membered bicyclic heteroaryl group, which is optionally substituted by 1, 2, 3 or 4 substituents independently selected from the group, consisting of cyano, amino, amino-$(C_{1-6})$alkyl, $(C_{1-6})$alkyl-amino-$(C_{1-6})$alkyl, di$(C_{1-4})$alkyl-amino-$(C_{1-6})$alkyl, aminocarbonyl, thiocarbamoyl, halogen, $(C_{1-6})$alkyl, halogen-$(C_{1-6})$alkyl, hydroxy, oxo, $(C_1$-6$)$alkoxy, halogen-$(C_{1-6})$alkoxy, $(C_{1-6})$alkylthio, halogen-$(C_{1-6})$alkylthio, $(C_{1-6})$alkoxy-$(C_{1-6})$alkyl, $(C_{3-6})$cycloalkyl-$(C_{1-6})$alkoxy, $(C_{1-6})$alkoxy-$(C_{1-6})$alkoxy, $(C_{1-6})$alkoxy-$(C_{1-6})$alkylthio, $(C_1$-6$)$alkylthio-$(C_{1-6})$alkyl, $(C_{1-6})$alkylthio-$(C_{1-6})$alkoxy, $(C_{1-6})$alkylthio-$(C_{1-6})$alkylthio, $(C_{2-6})$alkenyl, $(C_{2-6})$alkynyl, $(C_{2-6})$alkenoxy, $(C_{2-6})$alkynoxy.
(19) $R_2$ is a 9- or 10- or membered bicyclic heteroaryl group, which is optionally substituted by 1, 2, 3 or 4 substituents independently selected from the group, consisting of cyano, amino, halogen, $(C_{1-4})$alkyl, difluoromethyl, trifluoromethyl, hydroxy, oxo, $(C_{1-4})$alkoxy, $(C_{1-4})$alkoxy-$(C_{1-4})$alkyl and halogen-$(C_{1-4})$alkoxy.
(20) $R_2$ is a 9-membered bicyclic heteroaryl group in which structure 1, 2 or 3 ring members are nitrogen ring members, which is optionally substituted by 1, 2, 3 or 4 substituents independently selected from the group, consisting of cyano, amino, amino-$(C_{1-6})$alkyl, $(C_{1-6})$alkyl-amino-$(C_{1-6})$alkyl, di$(C_{1-4})$alkyl-amino-$(C_{1-6})$alkyl, aminocarbonyl, thiocarbamoyl, halogen, $(C_{1-6})$alkyl, halogen-$(C_{1-6})$alkyl, hydroxy, oxo, $(C_{1-6})$alkoxy, halogen-$(C_{1-6})$alkoxy, $(C_{1-6})$alkylthio, halogen-$(C_{1-6})$alkylthio, $(C_{1-6})$alkoxy-$(C_{1-6})$alkyl, $(C_{3-6})$cycloalkyl-$(C_{1-6})$alkoxy, $(C_{1-6})$alkoxy-$(C_{1-6})$alkoxy, $(C_{1-6})$alkoxy-$(C_{1-6})$alkylthio, $(C_{1-6})$alkylthio-$(C_{1-6})$alkyl, $(C_{1-6})$alkylthio-$(C_{1-6})$alkoxy, $(C_{1-6})$alkylthio-$(C_{1-6})$alkylthio, $(C_{2-6})$alkenyl, $(C_{2-6})$alkynyl, $(C_{2-6})$alkenoxy, $(C_{2-6})$alkynoxy.

(21) $R_2$ is a 9-membered bicyclic heteroaryl group in which structure 1, 2 or 3 ring members are nitrogen ring members, which is optionally substituted by 1, 2, 3 or 4 substituents independently selected from the group, consisting of cyano, amino, halogen, $(C_{1-4})$alkyl, difluoromethyl, trifluoromethyl, hydroxy, oxo, $(C_{1-4})$alkoxy, $(C_{1-4})$alkoxy-$(C_{1-4})$alkyl and halogen-$(C_{1-4})$alkoxy.

(22) $R_2$ is a 5- or 6-membered heteroaryl group in which structure 1, 2, 3, or 4 ring members are hetero ring members independently selected from the group consisting of a nitrogen ring member, an oxygen ring member and a sulfur ring member, which group is optionally substituted by 1, 2, 3 or 4 substituents independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{3-4})$cycloalkyl-$(C_{1-4})$alkoxy, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

(23) $R_2$ is a 6-membered heteroaryl group in which structure 1, 2, 3, or 4 ring members are hetero ring members independently selected from the group consisting of a nitrogen ring member, an oxygen ring member and a sulfur ring member, which group is optionally substituted by 1, 2, 3 or 4 substituents independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{3-4})$cycloalkyl-$(C_{1-4})$alkoxy, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

(24) $R_2$ is a 6-membered heteroaryl group in which structure 1, 2, 3, or 4 ring members are hetero ring members independently selected from the group consisting of a nitrogen ring member, an oxygen ring member and a sulfur ring member, which group is optionally substituted by 1, 2, 3 or 4 substituents independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(25) $R_2$ is a pyridyl or pyrazinyl group which is optionally substituted by 1, 2 or 3 substituents independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{3-4})$cycloalkyl-$(C_{1-4})$alkoxy, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

(26) $R_2$ is a pyridyl or pyrazinyl group which is optionally substituted by 1, 2 or 3 substituents independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(27) $R_2$ is a pyridin-2-yl or pyrazin-2-yl group which is optionally substituted by 1, 2 or 3 substituents independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{3-4})$cycloalkyl-$(C_{1-4})$alkoxy, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

(28) $R_2$ is a pyridin-2-yl or pyrazin-2-yl group which is optionally substituted by 1, 2 or 3 substituents independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(29) $R_2$ is a pyridin-2-yl or pyrazin-2-yl group which is optionally substituted by 1 or 2 substituents independently selected from the group, consisting of cyano, amino, fluoro, bromo, chloro, hydroxyl, oxo, methyl, fluoromethyl, difluoromethyl, trifluoromethyl, methoxy, fluoromethoxy, difluoromethoxy and trifluoromethoxy.

(30) $R_2$ is a pyridyl or pyrazinyl group which is substituted by 1, 2 or 3 substituents and wherein one of the substituents is located at the para position of the pyridyl or pyrazinyl group relative to the amide linker and wherein the substituents are independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{3-4})$cycloalkyl-$(C_{1-4})$alkoxy, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

(31) $R_2$ is a pyridyl or pyrazinyl group which is substituted by 1, 2 or 3 substituents and wherein one of the substituents is located at the para position of the pyridyl or pyrazinyl group relative to the amide linker and wherein the substituents are independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(32) $R_2$ is a pyridin-2-yl or pyrazin-2-yl group which is substituted by 1, 2 or 3 substituents and wherein one of the substituents is located at the para position of the pyridin-2-yl or pyrazin-2-yl group relative to the amide linker and wherein the substituents are independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(33) $R_2$ is a pyridyl or pyrazinyl group which is substituted by 2 or 3 substituents and wherein one of the substituents is located at the para position and one of the substituents is located at the ortho position of the pyridyl or pyrazinyl group relative to the amide linker and wherein the substituents are independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{3-4})$cycloalkyl-$(C_{1-4})$alkoxy, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

(34) $R_2$ is a pyridyl or pyrazinyl group which is substituted by 2 or 3 substituents and wherein one of the substituents is located at the para position and one of the substituents is located at the ortho position of the pyridyl or pyrazinyl group relative to the amide linker and wherein the substituents are independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(35) $R_2$ is a pyridin-2-yl or pyrazin-2-yl group which is substituted by 2 substituents and wherein one of the substituents is located at the para position and one of the substituents is located at the ortho position of the pyridin-2-yl or pyrazin-2-yl group relative to the amide linker and wherein the substituents are independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy.

(36) $R_2$ is a pyridin-2-yl or pyrazin-2-yl group which is substituted by 2 substituents and wherein one of the substituents is located at the para position and one of the substituents is located at the ortho position of the pyridin-2-yl or pyrazin-2-yl group relative to the amide linker and wherein the substituents are independently selected from the group, consisting of cyano, amino, fluoro, bromo, chloro, hydroxyl, oxo, methyl, fluoromethyl, difluoromethyl, trifluoromethyl, methoxy, fluoromethoxy, difluoromethoxy and trifluoromethoxy.

(37) $R_3$ is hydrogen, cyano, halogen, $(C_{1-4})$alkyl, halogen-$(C_{1-4})$alkyl, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, or $(C_{2-4})$alkynyl.

(38) $R_3$ is hydrogen, cyano, halogen, $(C_{1-4})$alkyl, halogen-$(C_{1-4})$alkyl, $(C_{1-4})$alkoxy, or halogen-$(C_{1-4})$alkoxy.

(39) $R_3$ is hydrogen.

(40) $R_4$ is hydrogen, cyano, halogen, $(C_{1-4})$alkyl, halogen-$(C_{1-4})$alkyl, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, or $(C_{2-4})$alkynyl.

(41) $R_4$ is hydrogen, cyano, halogen, $(C_{1-4})$alkyl, halogen-$(C_{1-4})$alkyl, $(C_{1-4})$alkoxy, or halogen-$(C_{1-4})$alkoxy.

(42) $R_4$ is hydrogen or halogen.

(43) $R_4$ is hydrogen.

(44) $R_4$ is fluoro.

(45) $R_5$ is hydrogen, cyano, halogen, $(C_{1-4})$alkyl, halogen-$(C_{1-4})$alkyl, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, or $(C_{2-4})$alkynyl.

(46) $R_5$ is hydrogen, cyano, halogen, $(C_{1-4})$alkyl, halogen-$(C_{1-4})$alkyl, $(C_{1-4})$alkoxy, or halogen-$(C_{1-4})$alkoxy.

(47) $R_5$ is hydrogen or halogen.

(48) $R_5$ is hydrogen or fluoro.

(49) $R_5$ is halogen.

(50) $R_5$ is fluoro;

(51) $R_5$ is hydrogen.

(52) $R_6$ is hydrogen, $(C_{1-4})$alkyl, halogen-$(C_{1-4})$alkyl, hydroxy-$(C_{1-4})$alkyl, $(C_{1-4})$alkoxy-$(C_{1-4})$alkyl, mercapto-$(C_{1-4})$alkyl, $(C_{1-4})$alkylthio-$(C_{1-4})$alkyl, amino-$(C_{1-4})$alkyl, $(C_{1-4})$alkyl-amino-$(C_{1-4})$alkyl, di$(C_{1-4})$alkyl-amino-$(C_{1-4})$alkyl, $(C_{2-4})$alkenyl, or $(C_{2-4})$alkynyl.

(53) $R_6$ is $(C_{1-4})$alkyl, halogen-$(C_{1-4})$alkyl, hydroxy-$(C_{1-4})$alkyl, $(C_{1-4})$alkoxy-$(C_{1-4})$alkyl, mercapto-$(C_{1-4})$alkyl, $(C_{1-4})$alkylthio-$(C_{1-4})$alkyl, amino-$(C_{1-4})$alkyl, $(C_{1-4})$alkyl-amino-$(C_{1-4})$alkyl, di$(C_{1-4})$alkyl-amino-$(C_{1-4})$alkyl, $(C_{2-4})$alkenyl, or $(C_{2-4})$alkynyl.

(54) $R_6$ is $(C_{1-3})$alkyl or halogen-$(C_{1-3})$alkyl.

(55) $R_6$ is $(C_{1-3})$alkyl or fluoro-$(C_{1-3})$alkyl.

(56) $R_6$ is methyl, fluoromethyl, difluoromethyl or trifluoromethyl.

(57) $E_1$ is —$C(R_7)(R_8)$—, or —$C(R_7)(R_8)$—$C(R_9)(R_{10})$,

(58) $E_1$ is —$C(R_7)(R_8)$—.

(59) $E_2$ is —$C(R_{11})(R_{12})$—, or —$C(R_{11})(R_{12})$—$C(R_{13})(R_{14})$—.

(60) $E_2$ is —$C(R_{11})(R_{12})$—.

(61) either each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_7$ and $R_8$, taken together, are oxo or —$CH_2$—$CH_2$—.

(62) either each of $R_7$ and $R_8$ is independently selected from the group, consisting of hydrogen, cyano, halogen, $(C_{1-3})$alkyl and halogen-$(C_{1-3})$alkyl;

or $R_7$ and $R_8$, taken together, are oxo or —$CH_2$—$CH_2$—.

(63) either each of $R_7$ and $R_8$ is hydrogen;

or $R_7$ and $R_8$, taken together, are oxo.

(64) each of $R_7$ and $R_8$ is hydrogen.

(65) either each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_9$ and $R_{10}$, taken together, are oxo or —$CH_2$—$CH_2$—.

(66) each of $R_9$ and $R_{10}$ is hydrogen.

(67) either each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_{11}$ and $R_{12}$, taken together, are oxo or —$CH_2$—$CH_2$—;

(68) each of $R_{11}$ and $R_{12}$ is independently selected from the group, consisting of hydrogen, halogen, $(C_{1-8})$alkyl and halogen-$(C_{1-8})$alkyl;

each of $R_{11}$ and $R_{12}$ is independently selected from the group, consisting of hydrogen, $(C_{1-8})$alkyl and halogen-$(C_{1-8})$alkyl;

(69) either each of $R_{11}$ and $R_{12}$ is independently selected from the group, consisting of hydrogen, cyano, halogen, $(C_{1-3})$alkyl and halogen-$(C_{1-3})$alkyl;

or $R_{11}$ and $R_{12}$, taken together, are oxo or —$CR_{15}R_{16}$—$CR_{17}R_{18}$— wherein $R_{16}$, $R_{17}$, $R_{18}$ and $R_{19}$ are independently selected from hydrogen and fluoro;

(70) either each of $R_{11}$ and $R_{12}$ is independently selected from the group, consisting of hydrogen, $(C_{1-3})$alkyl and halogen-$(C_{1-3})$alkyl;

or $R_{11}$ and $R_{12}$, taken together, are oxo;

(71) either each of $R_{11}$ and $R_{12}$ is independently selected from the group, consisting of hydrogen, methyl and ethyl;

or $R_{11}$ and $R_{12}$, taken together, are oxo;

(72) each of $R_{11}$ and $R_{12}$ is independently selected from the group, consisting of hydrogen, $(C_{1-3})$alkyl and halogen-$(C_{1-3})$alkyl;
(73) $R_{11}$ is $(C_{1-8})$alkyl, and $R_{12}$ is halogen-$(C_{1-8})$alkyl;
(74) $R_{11}$ is $(C_{1-3})$alkyl, and $R_{12}$ is halogen-$(C_{1-3})$alkyl;
(75) each of $R_{11}$ and $R_{12}$ is independently selected from the group, consisting of hydrogen, $(C_{1-3})$alkyl and fluoro-$(C_{1-3})$alkyl;
(76) each of $R_{11}$ and $R_{12}$ is independently selected from the group, consisting of hydrogen, methyl, fluoromethyl, difluoromethyl and trifluoromethyl;
(77) $R_{11}$ and $R_{12}$ is hydrogen;
(78) $R_{11}$ and $R_{12}$, taken together, are oxo;
(79) either
each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{13}$ and $R_{14}$, taken together, are oxo or —$CH_2$—$CH_2$—;
(80) each of $R_{13}$ and $R_{14}$ is hydrogen.

The skilled person would understand that the embodiments (1) to (80) may be used independently, collectively or in any combination or sub-combination to the limit the scope of the invention as described hereinbefore in relation to compounds of the formula I, Ia, Ib, Ic, Id or Ie.

In one embodiment, the invention relates to a compound of the formula

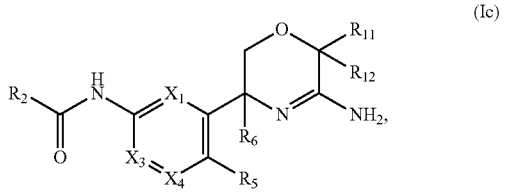

(Ic)

in which
$X_1$ is $CR_1$ or N;
$X_3$ is $CR_3$ or N;
$X_4$ is $CR_4$ or N;
wherein at least one of $X_1$, $X_3$ and $X_4$ is N and not more than 2 of $X_1$, $X_3$ and $X_4$ are N;
$R_1$ is hydrogen, cyano, halogen, $(C_{1-4})$alkyl, halogen-$(C_{1-4})$alkyl, $(C_{1-4})$alkoxy, or halogen-$(C_{1-4})$alkoxy;
$R_2$ is a 5- or 6-membered heteroaryl group in which structure 1, 2, 3, or 4 ring members are hetero ring members independently selected from the group consisting of a nitrogen ring member, an oxygen ring member and a sulfur ring member, which group is optionally substituted by 1, 2, 3 or 4 substituents independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{1-4})$alkoxy-$(C_{1-4})$alkoxy, $(C_{1-4})$alkoxy-$(C_{1-4})$alkylthio, $(C_{1-4})$alkylthio-$(C_1-4)$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy;
$R_3$, $R_4$ and $R_5$ are independently selected from the group consisting of hydrogen, cyano, halogen, $(C_{1-4})$alkyl, halogen-$(C_{1-4})$alkyl, $(C_{1-4})$alkoxy, or halogen-$(C_{1-4})$alkoxy;
$R_6$ is $(C_{1-3})$alkyl or fluoro-$(C_{1-3})$alkyl; and each of $R_{11}$ and $R_{12}$ is independently selected from the group, consisting of hydrogen, $(C_{1-3})$alkyl and halogen-$(C_{1-3})$alkyl;
or a pharmaceutically acceptable salt thereof.

In another embodiment, the invention relates to a compound of the formula Ic
in which
$X_1$ is CH or N;
$X_3$ is CH or N;
$X_4$ is $CR_4$ or N;
wherein one and not more than one of $X_1$, $X_3$ and $X_4$ is N;
$R_2$ is a pyridyl or pyrazinyl group which is optionally substituted by 1, 2 or 3 substituents independently selected from the group, consisting of cyano, amino, aminocarbonyl, thiocarbamoyl, halogen, $(C_{1-4})$alkyl, halogen-$(C_{1-4})$alkyl, hydroxy, oxo, $(C_1-4)$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy;
$R_4$ and $R_5$ are independently hydrogen, or halogen;
$R_6$ is $(C_{1-3})$alkyl or fluoro-$(C_{1-3})$alkyl; and
each of $R_{11}$ and $R_{12}$ is independently selected from the group, consisting of hydrogen, $(C_{1-3})$alkyl and fluoro-$(C_{1-3})$alkyl;
or a pharmaceutically acceptable salt thereof.

In a further embodiment, the invention relates to a compound of the formula

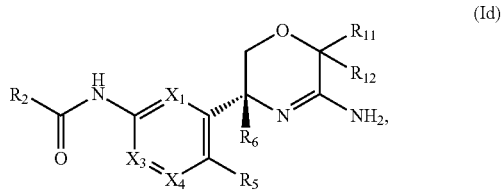

(Id)

in which
$X_1$ is CH or N;
$X_3$ is CH or N;
$X_4$ is $CR_4$ or N;
wherein one and not more than one of $X_1$, $X_3$ and $X_4$ is N;
$R_2$ is a pyridyl or pyrazinyl group which is substituted by 2 or 3 substituents and wherein one of the substituents is located at the para position and one of the substituents is located at the ortho position of the pyridyl or pyrazinyl group relative to the amide linker and wherein the substituents are independently selected from the group, consisting of cyano, amino, halogen, $(C_{1-4})$alkyl, halogen-$(C_{1-4})$alkyl, hydroxy, oxo, $(C_{1-4})$alkoxy and halogen-$(C_{1-4})$alkoxy;
$R_4$ and $R_5$ are independently hydrogen, or halogen;
$R_6$ is methyl, fluoromethyl, difluoromethyl or trifluoromethyl; and
each of $R_{11}$ and $R_{12}$ is independently selected from the group, consisting of hydrogen, methyl, fluoromethyl, difluoromethyl and trifluoromethyl;
or a pharmaceutically acceptable salt thereof.

In a further embodiment, the invention relates to a compound of the formula

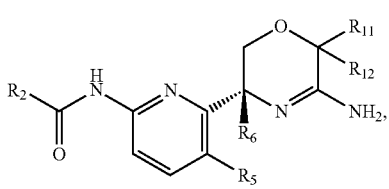
(Ie)

in which
R$_2$ is a pyridin-2-yl or pyrazin-2-yl group which is substituted by 2 substituents and wherein one of the substituents is located at the para position and one of the substituents is located at the ortho position of the pyridin-2-yl or pyrazin-2-yl group relative to the amide linker and wherein the substituents are independently selected from the group, consisting of cyano, amino, fluoro, bromo, chloro, hydroxyl, oxo, methyl, fluoromethyl, difluoromethyl, trifluoromethyl, methoxy, fluoromethoxy, difluoromethoxy and trifluoromethoxy;
R$_5$ is hydrogen or fluoro;
R$_6$ is methyl, fluoromethyl or difluoromethyl; and
each of R$_{11}$ and R$_{12}$ is independently selected from the group, consisting of hydrogen, methyl, fluoromethyl, difluoromethyl and trifluoromethyl;
or a pharmaceutically acceptable salt thereof.

In another embodiment, the invention relates to a compound of the invention which is selected from:
5-Bromo-pyridine-2-carboxylic acid [6-(5-amino-3-methyl-3,6-dihydro-2H-[1,4]-oxazin-3-yl)-pyridin-2-yl]-amide;
5-Chloro-pyridine-2-carboxylic acid [6-(5-amino-3-fluoromethyl-3,6-dihydro-2H-[1,4]oxazin-3-yl)-pyridin-2-yl]-amide;
5-Bromo-pyridine-2-carboxylic acid [6-(5-amino-3-fluoromethyl-3,6-dihydro-2H-[1,4]oxazin-3-yl)-pyridin-2-yl]-amide;
5-Cyano-3-methyl-pyridine-2-carboxylic acid [6-(5-amino-3-fluoromethyl-3,6-dihydro-2H-[1,4]oxazin-3-yl)-pyridin-2-yl]-amide;
4,6-Dideutero-5-chloro-3-trideuteromethyl-pyridine-2-carboxylic acid [6-(5-amino-3-fluoromethyl-3,6-dihydro-2H-[1,4]oxazin-3-yl)-pyridin-2-yl]-amide;
5-Thiocarbamoyl-pyridine-2-carboxylic acid [6-(5-amino-3-fluoromethyl-3,6-dihydro-2H-[1,4]oxazin-3-yl)-pyridin-2-yl]amide;
5-Cyano-3-methyl-pyridine-2-carboxylic acid [6-(5-amino-3,6-dimethyl-6-trifluoro-methyl-3,6-dihydro-2H-[1,4]oxazin-3-yl)-pyridin-2-yl]-amide;
5-Cyano-pyridine-2-carboxylic acid [6-(5-amino-3,6-dimethyl-6-trifluoromethyl-3,6-dihydro-2H-[1,4]oxazin-3-yl)-pyridin-2-yl]-amide;
5-Cyano-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]-amide;
4,6-Dideutero-5-chloro-3-trideuteromethyl-pyridine-2-carboxylic acid [4-(5-amino-3-fluoromethyl-3,6-dihydro-2H-[1,4]oxazin-3-yl)-pyridin-2-yl]-amide;
5-Chloro-pyridine-2-carboxylic acid [4-(5-amino-3-fluoromethyl-3,6-dihydro-2H-[1,4]oxazin-3-yl)-pyridin-2-yl]amide;
5-Cyano-3-methyl-pyridine-2-carboxylic acid [4-(5-amino-3,6-dimethyl-6-trifluoromethyl-3,6-dihydro-2H-[1,4]oxazin-3-yl)-5-fluoro-pyridin-2-yl]-amide;
5-Bromo-pyridine-2-carboxylic acid [5-(5-amino-3-fluoromethyl-3,6-dihydro-2H-[1,4]oxazin-3-yl)-6-chloro-pyridin-3-yl]-amide;
3-Amino-5-cyano-pyridine-2-carboxylic acid [6-(5-amino-3,6-dimethyl-6-trifluoromethyl-3,6-dihydro-2H-[1,4]oxazin-3-yl)-pyridin-2-yl]-amide;
3-Chloro-5-cyano-pyridine-2-carboxylic acid [6-(5-amino-3,6-dimethyl-6-trifluoromethyl-3,6-dihydro-2H-[1,4]oxazin-3-yl)-pyridin-2-yl]-amide;
5-Chloro-4,6-dideuterio-3-trideuteriomethyl-pyridine-2-carboxylic acid [6-(5-amino-3,6-dimethyl-6-trifluoromethyl-3,6-dihydro-2H-[1,4]oxazin-3-yl)-pyridin-2-yl]-amide;
5-Bromo-3-chloro-pyridine-2-carboxylic acid [6-(5-amino-3,6-dimethyl-6-trifluoromethyl-3,6-dihydro-2H-[1,4]oxazin-3-yl)-pyridin-2-yl]-amide;
3-Amino-5-(2,2,2-trifluoro-ethoxy)-pyrazine-2-carboxylic acid [6-(5-amino-3,6-dimethyl-6-trifluoromethyl-3,6-dihydro-2H-[1,4]oxazin-3-yl)-pyridin-2-yl]-amide;
3-Chloro-5-cyano-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]-amide;
5-Methoxy-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3-Amino-5-(2,2,2-trifluoro-ethoxy)-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3-Amino-5-cyano-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
5-Difluoromethoxy-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3-Chloro-5-difluoromethoxy-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3,5-Dichloro-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
5-Fluoromethoxy-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
5-Methyl-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3-Chloro-5-trifluoromethyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3-Chloro-5-cyano-pyridine-2-carboxylic acid [4-(5-amino-3,6-dimethyl-6-trifluoromethyl-3,6-dihydro-2H-[1,4]oxazin-3-yl)-5-fluoro-pyridin-2-yl]amide;
3-Chloro-5-difluoromethoxy-pyridine-2-carboxylic acid [4-(5-amino-3,6-dimethyl-6-trifluoromethyl-3,6-dihydro-2H-[1,4]oxazin-3-yl)-5-fluoro-pyridin-2-yl]-amide;
5-Cyano-3-methyl-pyridine-2-carboxylic acid [4-(5-amino-6,6-bis-fluoromethyl-3-methyl-3,6-dihydro-2H-[1,4]oxazin-3-yl)-5-fluoro-pyridin-2-yl]-amide;
5-Cyano-3-methyl-pyridine-2-carboxylic acid [6-(5-amino-3-difluoromethyl-3,6-dihydro-2H-[1,4]oxazin-3-yl)-5-fluoro-pyridin-2-yl]amide;
3-Chloro-5-cyano-pyridine-2-carboxylic acid [6-(5-amino-3-difluoromethyl-3,6-dihydro-2H-[1,4]oxazin-3-yl)-5-fluoro-pyridin-2-yl]amide;
3,5-Dimethyl-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Amino-5-(3-fluoro-propoxy)-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Amino-5-(2-methoxy-ethyl)-5H-pyrrolo[2,3-b]pyrazine-2-carboxylic acid [6-((5-amino-3,6-dimethyl-6-trifluoromethyl-3,6-dihydro-2H-[1,4]oxazin-3-yl)-5-fluoro-pyridin-2-yl]amide;

3-Amino-5-trifluoromethyl-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Amino-5-(2,2-difluoro-ethyl)-5H-pyrrolo[2,3-b]pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]-amide;

4-Chloro-1-difluoromethyl-1H-pyrazole-3-carboxylic acid [6-(5-amino-3,6-dimethyl-6-trifluoromethyl-3,6-dihydro-2H-[1,4]oxazin-3-yl)-5-fluoro-pyridin-2-yl]-amide;

6-Chloro-1-(2,2-difluoro-ethyl)-1H-pyrrolo[3,2-b]pyridine-5-carboxylic acid [6-(5-amino-3,6-dimethyl-6-trifluoromethyl-3,6-dihydro-2H-[1,4]oxazin-3-yl)-5-fluoro-pyridin-2-yl]-amide; and 6-Chloro-1-(2-methoxy-ethyl)-1H-pyrrolo[3,2-b]pyridine-5-carboxylic acid [6-(5-amino-3,6-dimethyl-6-trifluoromethyl-3,6-dihydro-2H-[1,4]oxazin-3-yl)-5-fluoro-pyridin-2-yl]-amide;

and pharmaceutically acceptable salts thereof.

In another embodiment, the invention relates to a compound of the invention which is selected from:

5-Bromo-pyridine-2-carboxylic acid [6-((R)-5-amino-3-methyl-3,6-dihydro-2H-[1,4]-oxazin-3-yl)-pyridin-2-yl]-amide;

5-Chloro-pyridine-2-carboxylic acid [6-(5-amino-3-fluoromethyl-3,6-dihydro-2H-[1,4]oxazin-3-yl)-pyridin-2-yl]-amide;

5-Bromo-pyridine-2-carboxylic acid [6-(5-amino-3-fluoromethyl-3,6-dihydro-2H-[1,4]oxazin-3-yl)-pyridin-2-yl]-amide;

5-Cyano-3-methyl-pyridine-2-carboxylic acid [6-(5-amino-3-fluoromethyl-3,6-dihydro-2H-[1,4]oxazin-3-yl)-pyridin-2-yl]amide;

4,6-Dideutero-5-chloro-3-trideuteromethyl-pyridine-2-carboxylic acid [6-(5-amino-3-fluoromethyl-3,6-dihydro-2H-[1,4]oxazin-3-yl)-pyridin-2-yl]-amide;

5-Thiocarbamoyl-pyridine-2-carboxylic acid [6-(5-amino-3-fluoromethyl-3,6-dihydro-2H-[1,4]oxazin-3-yl)-pyridin-2-yl]-amide;

5-Cyano-3-methyl-pyridine-2-carboxylic acid [6-((3R,6R)-5-amino-3,6-dimethyl-6-trifluoro-methyl-3,6-dihydro-2H-[1,4]oxazin-3-yl)-pyridin-2-yl]-amide;

5-Cyano-pyridine-2-carboxylic acid [6-((3S,6R)-5-amino-3,6-dimethyl-6-trifluoromethyl-3,6-dihydro-2H-[1,4]oxazin-3-yl)-pyridin-2-yl]-amide;

5-Cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]amide;

5-Cyano-3-methyl-pyridine-2-carboxylic acid [6-((3R,6R)-5-amino-3,6-dimethyl-6-trifluoro-methyl-3,6-dihydro-2H-[1,4]oxazin-3-yl)-5-fluoro-pyridin-2-yl]-amide;

5-Cyano-3-methyl-pyridine-2-carboxylic acid [6-((3S,6R)-5-amino-3,6-dimethyl-6-trifluoromethyl-3,6-dihydro-2H-[1,4]oxazin-3-yl)-5-fluoro-pyridin-2-yl]-amide;

4,6-Dideutero-5-chloro-3-trideuteromethyl-pyridine-2-carboxylic acid [4-(5-amino-3-fluoromethyl-3,6-dihydro-2H-[1,4]oxazin-3-yl)-pyridin-2-yl]-amide;

5-Chloro-pyridine-2-carboxylic acid [4-(5-amino-3-fluoromethyl-3,6-dihydro-2H-[1,4]oxazin-3-yl)-pyridin-2-yl]-amide;

5-Cyano-3-methyl-pyridine-2-carboxylic acid [4-((3R,6R)-5-amino-3,6-dimethyl-6-trifluoromethyl-3,6-dihydro-2H-[1,4]oxazin-3-yl)-5-fluoro-pyridin-2-yl]-amide;

5-Cyano-3-methyl-pyridine-2-carboxylic acid [4-((3S,6R)-5-amino-3,6-dimethyl-6-trifluoromethyl-3,6-dihydro-2H-[1,4]oxazin-3-yl)-5-fluoro-pyridin-2-yl]-amide;

5-Bromo-pyridine-2-carboxylic acid [5-(5-amino-3-fluoromethyl-3,6-dihydro-2H-[1,4]oxazin-3-yl)-6-chloro-pyridin-3-yl]-amide;

3-Amino-5-cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide;

3-Chloro-5-cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide;

5-Chloro-4,6-dideuterio-3-trideuteriomethyl-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide;

5-Bromo-3-chloro-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide;

3-Amino-5-(2,2,2-trifluoro-ethoxy)-pyrazine-2-carboxylic acid [6-((3R,6R)-5-amino-3,6-dimethyl-6-trifluoromethyl-3,6-dihydro-2H-[1,4]oxazin-3-yl)-pyridin-2-yl]-amide;

3-Chloro-5-cyano-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide;

5-Methoxy-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Amino-5-(2,2,2-trifluoro-ethoxy)-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Amino-5-cyano-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Chloro-5-cyano-pyridine-2-carboxylic acid [6-((3S,6R)-5-amino-3,6-dimethyl-6-trifluoromethyl-3,6-dihydro-2H-[1,4]oxazin-3-yl)-5-fluoro-pyridin-2-yl]amide;

5-Difluoromethoxy-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Chloro-5-difluoromethoxy-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3,5-Dichloro-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

5-Fluoromethoxy-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

5-Methyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Chloro-5-trifluoromethyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Chloro-5-cyano-pyridine-2-carboxylic acid [4-((3R,6R)-5-amino-3,6-dimethyl-6-trifluoromethyl-3,6-dihydro-2H-[1,4]oxazin-3-yl)-5-fluoro-pyridin-2-yl]-amide;

3-Chloro-5-difluoromethoxy-pyridine-2-carboxylic acid [4-((3S,6R)-5-amino-3,6-dimethyl-6-trifluoromethyl-3,6-dihydro-2H-[1,4]oxazin-3-yl)-5-fluoro-pyridin-2-yl]-amide;

5-Cyano-3-methyl-pyridine-2-carboxylic acid [4-((R)-5-amino-6,6-bis-fluoromethyl-3-methyl-3,6-dihydro-2H-[1,4]oxazin-3-yl)-5-fluoro-pyridin-2-yl]-amide;

5-Cyano-3-methyl-pyridine-2-carboxylic acid [6-((R)-5-amino-3-difluoromethyl-3,6-dihydro-2H-[1,4]oxazin-3-yl)-5-fluoro-pyridin-2-yl]amide;

5-Cyano-3-methyl-pyridine-2-carboxylic acid [6-((S)-5-amino-3-difluoromethyl-3,6-dihydro-2H-[1,4]oxazin-3-yl)-5-fluoro-pyridin-2-yl]amide;

3-Chloro-5-cyano-pyridine-2-carboxylic acid [6-((R)-5-amino-3-difluoromethyl-3,6-dihydro-2H-[1,4]oxazin-3-yl)-5-fluoro-pyridin-2-yl]amide;

3,5-Dimethyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Amino-5-(3-fluoro-propoxy)-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Amino-5-(2-methoxy-ethyl)-5H-pyrrolo[2,3-b]pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Amino-5-trifluoromethyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide;

3-Amino-5-(2,2-difluoro-ethyl)-5H-pyrrolo[2,3-b]pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide;

4-Chloro-1-difluoromethyl-1H-pyrazole-3-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide;

6-Chloro-1-(2,2-difluoro-ethyl)-1H-pyrrolo[3,2-b]pyridine-5-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide; and 6-Chloro-1-(2-methoxy-ethyl)-1H-pyrrolo[3,2-b]pyridine-5-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide;

and pharmaceutically acceptable salts thereof.

In a further aspect, the invention relates to a process for the preparation of a compound of the formula I, in free form or in salt form, comprising a) the reaction of a compound of the formula

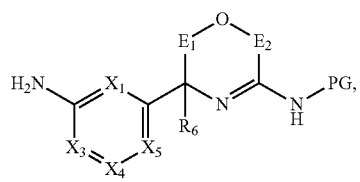
(II)

in free form or in salt form, in which $X_1$, $X_3$, $X_4$, $X_5$, $R_6$, $E_1$ and $E_2$ are as defined for the formula I and PG is a protecting group, with a compound of the formula

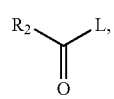
(III)

in which $R_2$ is as defined for the formula I and L is a leaving group, for example a hydroxy group, in free form or in salt form, b) the reaction of a compound of the formula

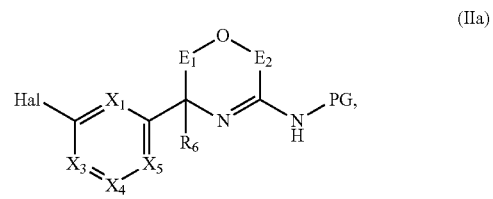
(IIa)

in free form or in salt form, in which $X_1$, $X_3$, $X_4$, $X_5$, $R_6$, $E_1$ and $E_2$ are as defined for the formula I, Hal is halogen, for example bromine, and PG is a protecting group, with a compound of the formula

(IIIa)

in which $R_2$ is as defined for the formula I, in free form or in salt form, c) the reaction of a compound of the formula

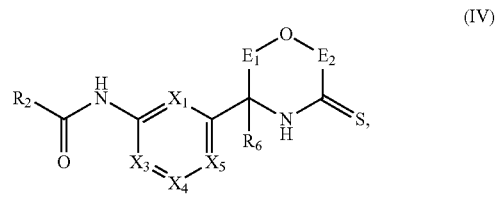
(IV)

in which $X_1$, $X_3$, $X_4$, $X_5$, $R_2$, $R_6$, $E_1$ and $E_2$ are as defined for the formula I, in free form or in salt form, with ammonia, d) the optional reduction, oxidation or other functionalisation of the resulting compound, e) the cleavage of any protecting group(s) optionally present and f) the recovery of the so obtainable compound of the formula I in free form or in salt form.

The reactions can be effected according to conventional methods, for example as described in the Examples.

The working-up of the reaction mixtures and the purification of the compounds thus obtainable may be carried out in accordance with known procedures.

Salts may be prepared from free compounds in known manner, and vice-versa.

In more detail, the reaction of a compound of formula (II) with a compound of formula (III) as described in step a) may be carried out in the presence of a suitable coupling agent, for example 1-hydroxy-7-azabenzotriazole, a suitable activating agent, for example 1-(3-dimethylaminopropyl)-3-ethylcarbodiimide hydrochloride, a suitable base, for example diisopropylethylamine, a suitable solvent, for example dimethylformamide, and at a suitable temperature, for example 0 to 50° C., more suitably 0 to 25° C.

In more detail, the reaction of a compound of formula (IIa) with a compound of formula (IIIa) as described in step b) may be carried out in the presence of, a suitable catalyst, for example tris(dibenzylidene-acetone) di palladium, a suitable ligand, for example Xanthphos, a suitable base, for example cesium carbonate, a suitable solvent, for example 1,4-dioxane, and at a suitable temperature, for example 10 to 100° C., more suitably 30 to 85° C.

In more detail, the reaction of a compound of formula (IV) with ammonia as described in step c) may be carried out in the presence of a suitable solvent, for example methanol, and at a suitable temperature, for example 0 to 50° C., more suitably 0 to 30° C.

Compounds of the formula I can also be prepared by further processes, which processes are further aspects of the invention, for example as described in the Examples.

The starting materials of the formulae II, IIa, III, IIIa and IV are known or may be prepared according to conventional procedures starting from known compounds, may be prepared from known compounds as described in the Examples or may be prepared using procedures analogous to those described in the Examples.

Compounds of the formula I, in free form, salt form, or in pharmaceutically acceptable salt form, hereinafter often referred to as "agents of the invention", exhibit valuable pharmacological properties, when tested in vitro or in vivo, and may, therefore, be useful in medicaments, in therapy or for use as research chemicals, for example as tool compounds.

For example, agents of the invention are inhibitors of BACE-1 and BACE-2 and may be used for the treatment or prevention of a condition, disease or disorder involving processing by such enzymes, particularly the generation of beta-amyloid and the subsequent aggregation into oligomers and fibrils, and loss of β cell mass and/or function.

The inhibiting properties of an agent of the invention towards proteases can be evaluated in tests as described hereinafter.

Test 1: Inhibition of Human BACE-1

Recombinant BACE-1 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic fluorescence-quenched peptide substrate, derived from the sequence of APP and containing a suitable fluorophore-quencher pair, is added to a final concentration of 1 to 5 μM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-1 activity as a function of the test compound concentration.

Test 2: Inhibition of Human BACE-2

Recombinant BACE-2 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic fluorescence-quenched peptide substrate, derived from the sequence of APP and containing a suitable fluorophore-quencher pair, is added to a final concentration of 1 to 5 μM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-2 activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0 to 5.0. Synthetic peptide substrate Mca-Gly-Lys-Pro-Ile-Leu-Phe-Phe-Arg-Leu-Lys(DNP)-D-Arg-$NH_2$ is added to a final concentration of 1 to 5 μM, and the increase in fluorescence is recorded at excitation of 325 nm and emission at 400 nm in a microplate spectro-fluorimeter for 5 to 30 minutes in 1-minute intervals. $IC_{50}$ values are calculated from the percentage of inhibition of cathepsin D-activity as a function of the test compound concentration.

Test 4: Inhibition of Cellular Release of Amyloid Peptide 1-40

Chinese hamster ovary cells are transfected with the human gene for amyloid precursor protein. The cells are plated at a density of 8000 cells/well into 96-well microtiter plates and cultivated for 24 hours in DMEM cell culture medium containing 10% FCS. The test compound is added to the cells at various concentrations, and the cells are cultivated for 24 hours in the presence of the test compound. The supernatants are collected, and the concentration of amyloid peptide 1-40 is determined using state of the art immunoassay techniques, for example sandwich ELISA, homogenous time-resolved fluorescence (HTRF) immunoassay, or electro-chemiluminescence immunoassay. The potency of the compound is calculated from the percentage of inhibition of amyloid peptide release as a function of the test compound concentration.

Agents of the invention were tested in at least one of the above-described tests.

The compounds of the Examples show the following mean $IC_{50}$ values in Test 1 described hereinbefore:

TABLE 1

| Example | BACE-1 $IC_{50}$ [μM] | Example | BACE-1 $IC_{50}$ [μM] |
|---|---|---|---|
| 1 | 0.39 | 2 | 0.79 |
| 3 | 2.6 | 4 | 1.6 |
| 5 | 0.27 | 6 | 0.55 |
| 7 | 2.1 | 8 | 0.005 |
| 9 | 6.2 | 10 | 0.039 |
| 11 | 0.004 | 12 | 0.49 |
| 13 | 3.7 | 14 | 8.1 |
| 15 | >10 | 16 | 0.082 |
| 17 | 7.6 | 18 | 0.14 |
| 19 | 0.043 | 20 | 0.01 |
| 21 | 0.031 | 22 | 0.013 |
| 23 | 1.2 | 24 | 0.006 |
| 25 | 0.093 | 26 | 0.4 |
| 27 | 0.011 | 28 | 1.1 |
| 29 | 0.026 | 30 | 0.025 |
| 31 | 0.007 | 32 | 0.045 |
| 33 | 0.82 | 34 | 0.007 |
| 35 | 0.15 | 36 | 0.41 |
| 37 | 0.38 | 38 | 0.033 |
| 39 | 1.5 | 40 | 0.042 |
| 41 | 0.23 | 42 | 0.2 |
| 43 | 1.2 | 44 | 0.04 |
| 45 | >10 | 46 | 0.01 |
| 47 | >10 | 48 | 7.3 |

The compounds of the Examples show the following mean $IC_{50}$ values in Test 2 described hereinbefore:

TABLE 2

| Example | BACE-2 $IC_{50}$ [μM] | Example | BACE-2 $IC_{50}$ [μM] |
|---|---|---|---|
| 1 | 0.26 | 2 | 0.36 |
| 3 | 1.4 | 4 | 1.7 |
| 5 | 1 | 6 | 0.24 |
| 7 | 8.7 | 8 | 0.02 |
| 9 | 9.9 | 10 | 0.1 |
| 11 | 0.012 | 12 | 1.3 |
| 13 | 1.5 | 14 | 4.8 |
| 15 | >10 | 16 | 0.055 |
| 17 | 4.2 | 18 | 0.13 |
| 19 | 0.082 | 20 | 0.041 |
| 21 | 0.008 | 22 | 0.005 |
| 23 | >10 | 24 | 0.01 |

TABLE 2-continued

| Example | BACE-2 IC$_{50}$ [µM] | Example | BACE-2 IC$_{50}$ [µM] |
|---|---|---|---|
| 25 | 0.015 | 26 | 6.4 |
| 27 | 0.012 | 28 | 1.9 |
| 29 | 0.024 | 30 | 0.024 |
| 31 | 0.001 | 32 | 0.007 |
| 33 | 0.33 | 34 | 0.03 |
| 35 | 0.12 | 36 | 0.28 |
| 37 | 0.43 | 38 | 0.16 |
| 39 | 6.5 | 40 | 0.17 |
| 41 | 0.13 | 42 | 1.0 |
| 43 | >10 | 44 | 0.18 |
| 45 | >10 | 46 | 0.005 |
| 47 | 5.4 | 48 | >10 |

Compounds of the Examples show the following mean IC$_{50}$ values in Test 4 described hereinbefore:

TABLE 3

| Example | Amyloid-β1-40 release IC$_{50}$ [µM] | Example | Amyloid-β1-40 release IC$_{50}$ [µM] |
|---|---|---|---|
| 1 | 0.041 | 2 | 0.058 |
| 3 | 0.14 | 4 | 0.098 |
| 5 | 0.04 | 6 | 0.063 |
| 7 | 0.64 | 8 | 0.006 |
| 9 | 1.9 | 10 | 0.017 |
| 11 | 0.002 | 12 | 0.28 |
| 13 | 0.55 | 14 | 0.66 |
| 15 | NT | 16 | 0.077 |
| 17 | 4.8 | 18 | 0.015 |
| 19 | 0.048 | 20 | 0.005 |
| 21 | 0.11 | 22 | 0.029 |
| 23 | 0.7 | 24 | 0.003 |
| 25 | 0.076 | 26 | 0.28 |
| 27 | 0.005 | 28 | NT |
| 29 | 0.024 | 30 | 0.024 |
| 31 | 0.01 | 32 | 0.026 |
| 33 | 0.13 | 34 | 0.003 |
| 35 | 0.14 | 36 | 0.41 |
| 37 | 0.083 | 38 | 0.005 |
| 39 | 0.29 | 40 | 0.012 |
| 41 | 0.161 | 42 | 0.072 |
| 43 | 0.37 | 44 | 0.03 |
| 45 | 3.6 | 46 | NT |
| 47 | NT | 48 | NT |

NT = Not Tested

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by BACE-1 or (ii) associated with BACE-1 activity, or (iii) characterized by activity (normal or abnormal) of BACE-1; or (2) reducing or inhibiting the activity of BACE-1. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of BACE-1. The meaning of the term "a therapeutically effective amount" as illustrated in the above embodiments for BACE-1 also applies by the same means to any other relevant proteins/peptides/enzymes, such as BACE-2, or cathepsin D.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevention" of any particular disease or disorder refers to the administration of a compound of the invention to a subject before any symptoms of that disease or disorder are apparent.

As used herein, a subject is "in need of" a treatment if such subject would benefit biologically, medically or in quality of life from such treatment.

As used herein, the term an "agent" of the invention is used interchangeably with the term a "compound" of the invention and has no difference in meaning therefrom.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

Due to their inhibiting properties towards proteases, and BACE-1 in particular, agents of the invention may be useful, e.g., in the treatment or prevention of a variety of disabilitating psychiatric, psychotic, neurological or vascular states, e.g. of a condition, disease or disorder of the vascular system or of the nervous system, in which beta-amyloid generation or aggregation plays a role. Based on the inhibition of BACE-2 (beta-site APP-cleaving enzyme 2) or cathepsin D, which are close homologues of the pepsin-type aspartyl proteases and beta-secretase, and the correlation of BACE-2 or cathepsin D expression with a more tumorigenic or metastatic potential of tumor cells, the agents of the invention may also be useful as anti-cancer medicaments, e.g. in the suppression of the metastasis process associated with tumor cells. Furthermore, based on the inhibition of BACE-2 and the correlation of BACE-2 activity with TME27 cleavage and β cell mass, the agents of the invention may also be useful for treating or preventing loss of β cell mass and/or function, e.g. in the treatment of diabetes.

The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e.g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e.g. neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile X syndrome; scrapie; cerebral amyloid angiopathy; an encephalopathy, e.g. transmissible spongiform encephalopathy; stroke; an attention disorder, e.g. attention deficit hyperactivity disorder; Tourette's syndrome; a speech disorder, including stuttering; a disorder of the circadian rhythm, e.g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e.g. in paraplegic patients; a hearing disorder, e.g. tinnitus or age-related hearing impairment; urinary incontinence; glaucoma; inclusion-body myositis; or a substance-related disorder, including substance abuse or dependency, including a substance, such as alcohol, withdrawal disorder. Agents of the invention may also be useful in enhancing cognition, e.g. in a subject suffering from a dementing condition, such as Alzheimer's disease; as premedication prior to anaesthesia or a minor medical intervention, such as endoscopy, including gastric endoscopy; or as ligands, e.g. radioligands or positron emission tomography (PET) ligands.

Due to their inhibiting properties towards BACE-2, compounds of the invention may be useful in the treatment or prevention of a disease or disorder mediated by BACE-2. Diseases and disorders associated with BACE-2 include: metabolic syndrome (such as dyslipidemia, obesity, insulin resistance, hypertension, microalbuminemia, hyperuricaemia, and hypercoagulability), insulin resistance, glucose intolerance (also known as impaired glucose tolerance or impaired glucose tolerance, IGT), obesity, hypertension, or diabetic complications (such as retinopathy, nephropathy, diabetic foot, ulcers, macroangiopathies, metabolic acidosis or ketosis, reactive hypoglycaemia, hyperinsulinaemia), glucose metabolic disorder, dyslipidaemias of different origins, atherosclerosis and related diseases, high blood pressure, chronic heart failure, Syndrome X, diabetes, non-insulin-dependent diabetes mellitus, Type 2 diabetes, Type 1 diabetes, body weight disorders, weight loss, body mass index and leptin related diseases.

Compounds of the invention may be suitable for preventing beta-cell degeneration such as apoptosis or necrosis of pancreatic beta cells, for improving or restoring the functionality of pancreatic cells, and/or increasing the number and/or size of pancreatic beta cells.

As used herein a patient is suffering from "obesity" if the patient exhibits at least one of:
a body mass index (BMI), i.e. the patient's mass (in kg) divided by the square of the patient's height (in m), of 30 or more;
an absolute waist circumference of >102 cm in men or >88 cm in women;
a waist-to-hip ratio >0.9 in men or >0.85 in women; or
a percent body fat >25% in men or >30% in women.

As used herein a patient is suffering from "Type 2 diabetes" if they meet the World Health Organisation criteria for Diabetes diagnosis (Definition and diagnosis of diabetes mellitus and intermediate hyperglycaemia, WHO, 2006), i.e. the patient exhibits at least one of:
a fasting plasma glucose ≥7.0 mmol/l (126 mg/dl); or
a venous plasma glucose ≥11.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
a fasting plasma glucose <7.0 mmol/l (126 mg/dl); and
a venous plasma glucose ≥7.8 and <11.1 mmol/l (200 mg/dl) 2 hours after ingestion of 75 g oral glucose load.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaernia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

For the above-mentioned indications, the appropriate dosage will vary depending on, e.g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e.g. in the form of a tablet or capsule, or parenterally, e.g. in the form of an injectable solution or suspension.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e.g. grapefruit juice, ketoconazole or, preferably, ritonavir. Such a composition may be manufactured in conventional manner, e.g. by mixing its components. Unit dosage forms contain, e.g., from about 0.1 to about 1000, preferably from about 1 to about 500, mg of an agent of the invention.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
- a) diluents, e.g., lactose, dextrose, sucrose, mannitol, sorbitol, cellulose and/or glycine;
- b) lubricants, e.g., silica, talcum, stearic acid, its magnesium or calcium salt and/or polyethyleneglycol; for tablets also
- c) binders, e.g., magnesium aluminum silicate, starch paste, gelatin, tragacanth, methylcellulose, sodium carboxymethylcellulose and/or polyvinylpyrrolidone; if desired
- d) disintegrants, e.g., starches, agar, alginic acid or its sodium salt, or effervescent mixtures; and/or
- e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to an agent of the invention for use as a medicament, for example for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In one embodiment, the invention relates to an agent of the invention for use in the treatment of a disease or disorder mediated by BACE-1, BACE-2 or cathepsin D activity. In another embodiment, the invention relates to an agent of the invention for use in the treatment or prevention of Alzheimer's Disease or mild cognitive impairment. In a further embodiment, the invention relates to an agent of the invention for use in the treatment or prevention of insulin resistance, glucose intolerance, type 2 diabetes, obesity, hypertension, or diabetic complications. In yet another embodiment, the invention relates to a compound of the invention for use in the treatment of impaired glucose tolerance or Type 2 diabetes.

In a further aspect, the invention relates to the use of an agent of the invention as an active pharmaceutical ingredient in a medicament, for example for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In a further embodiment, the invention relates to the use of an agent of the invention as an active pharmaceutical ingredient in a medicament for the treatment or prevention of a disease or disorder mediated by BACE-1, BACE-2 or cathepsin D activity. In one embodiment, the invention relates to the use of an agent of the invention as an active pharmaceutical ingredient in a medicament for the treatment or prevention of Alzheimer's Disease or mild cognitive impairment. In a further embodiment, the invention relates to the use of a compound of the invention as an active pharmaceutical ingredient in a medicament for the treatment or prevention of insulin resistance, glucose intolerance, type 2 diabetes, obesity, hypertension, or diabetic complications. In yet a further embodiment, the invention relates to the use of a compound of the invention as an active pharmaceutical ingredient in a medicament for the treatment or prevention of impaired glucose tolerance or Type 2 diabetes.

In a further aspect, the invention relates to the use of an agent of the invention for the manufacture of a medicament for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In a further embodiment, the invention relates to the use of an agent of the invention for the manufacture of a medicament for the treatment or prevention of a disease or disorder mediated by BACE-1, BACE-2 or cathepsin D activity. In one embodiment, the invention relates to the use of an agent of the invention for the manufacture of a medicament for the treatment or prevention of Alzheimer's Disease or mild cognitive impairment. In a further embodiment, the invention relates to the use of a compound of the invention as an active pharmaceutical ingredient in a medicament for the treatment or prevention of insulin resistance, glucose intolerance, type 2 diabetes, obesity, hypertension, or diabetic complications. In yet a further embodiment, the invention relates to the use of a compound of the invention as an active pharmaceutical ingredient in a medicament for the treatment or prevention of impaired glucose tolerance or Type 2 diabetes.

In a further aspect, the invention relates to a method for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function, in a subject in need of such treatment, prevention or suppression, which method comprises administering to such subject an effective amount of an agent of the invention. In one embodiment, the invention relates to a method of modulating BACE-1, BACE-2 or cathepsin D activity in a subject, wherein the method comprises administering to the subject a therapeutically effective amount of an agent of the invention. In another embodiment, the invention relates to a method for the treatment or prevention of a disease mediated by BACE-1, BACE-2 or cathepsin D activity, in a subject in need of such treatment or prevention, which method comprises administering to such subject an effective amount of an agent of the invention. In yet another embodiment, the invention relates to a method for the treatment or prevention of Alzheimer's Disease or mild cognitive impairment, in a subject in need of such treatment or prevention, which method comprises administering to such subject an effective amount of an agent of the invention. In a further embodiment, the invention relates to a method for the treatment or prevention of insulin resistance, glucose intolerance, type 2 diabetes, obesity, hypertension, or diabetic complications, in a subject in need of such treatment or prevention, which method comprises administering to such subject a therapeutically effective amount of a compound of the invention. In yet a further embodiment, the invention relates to a method for the treatment or prevention of impaired glucose tolerance or Type 2 diabetes, in a subject in need of such treatment or prevention, which method comprises administering to such subject a therapeutically effective amount of a compound of the invention.

An agent of the invention can be administered as sole active pharmaceutical ingredient or as a combination with at least one other active pharmaceutical ingredient effective, e.g., in the treatment or prevention of a neurological or vascular condition, disease or disorder, in which beta-amyloid generation or aggregation plays a role, or in the suppression of the metastasis process associated with tumor cells, or in the treatment or prevention of loss of β cell mass and/or function. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e.g. a pack or dispenser-device adapted for the concomitant or separate administration of the at least two active components, in which these active components are separately arranged. In a further aspect, the invention relates to such pharmaceutical combinations.

In a further aspect, the invention therefore relates to a pharmaceutical combination comprising a therapeutically effective amount of an agent of the invention and a second drug substance, for simultaneous or sequential administration.

In one embodiment, the invention provides a product comprising an agent of the invention and at least one other therapeutic agent as a combined preparation for simultaneous, separate or sequential use in therapy. In one embodiment, the therapy is the treatment of a disease or condition mediated by BACE-1, BACE-2 or cathepsin D activity, such as Alzheimer's Disease, mild cognitive impairment, impaired glucose tolerance or type 2 diabetes.

In one embodiment, the invention provides a pharmaceutical composition comprising an agent of the invention and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition mediated by BACE-1, BACE-2 or cathepsin D activity, such as Alzheimer's Disease, impaired glucose tolerance or type 2 diabetes, wherein the medicament is prepared for administration with another therapeutic agent. The invention also provides the use of another therapeutic agent for treating a disease or condition mediated by BACE-1, BACE-2 or cathepsin D activity, such as Alzheimer's Disease, impaired glucose tolerance or type 2 diabetes, wherein the medicament is administered with an agent of the invention.

The invention also provides an agent of the invention for use in a method of treating a disease or condition mediated by BACE-1, BACE-2 or cathepsin D activity, such as Alzheimer's Disease, impaired glucose tolerance or type 2 diabetes, wherein the agent of the invention is prepared for administration with another therapeutic agent. The invention also provides another therapeutic agent for use in a method of treating a disease or condition mediated by BACE-1, BACE-2 or cathepsin D activity, such as Alzheimer's Disease, impaired glucose tolerance or type 2 diabetes, wherein the other therapeutic agent is prepared for administration with an agent of the invention. The invention also provides an agent of the invention for use in a method of treating a disease or condition mediated by BACE-1, BACE-2 or cathepsin D activity, such as Alzheimer's Disease, impaired glucose tolerance or type 2 diabetes, wherein the agent of the invention is administered with another therapeutic agent. The invention also provides another therapeutic agent for use in a method of treating a disease or condition mediated by BACE-1, BACE-2 or cathepsin D activity, such as Alzheimer's Disease, impaired glucose tolerance or type 2 diabetes, wherein the other therapeutic agent is administered with an agent of the invention.

The invention also provides the use of an agent of the invention for treating a disease or condition mediated by BACE-1, BACE-2 or cathepsin D activity, such as Alzheimer's Disease, impaired glucose tolerance or type 2 diabetes, wherein the patient has previously (e.g. within 24 hours) been treated with another therapeutic agent. The invention also provides the use of another therapeutic agent for treating a disease or condition mediated by BACE-1, BACE-2 or cathepsin D activity, such as Alzheimer's Disease, impaired glucose tolerance or type 2 diabetes, wherein the patient has previously (e.g. within 24 hours) been treated with an agent of the invention.

In one embodiment, the invention relates to a compound of the invention in combination with another therapeutic agent wherein the other therapeutic agent is selected from:
(a) acetylcholinesterase inhibitors, such as donepezil (Aricept™), rivastigmine (Exelon™) and galantamine (Razadyne™);
(b) glutamate antagonists, such as memantine (Namenda™);
(c) antidepressant medications for low mood and irritability, such as citalopram (Celexa™) fluoxetine (Prozac™), paroxeine (Paxil™), sertraline (Zoloft™) and trazodone (Desyrel™);
(d) anxiolytics for anxiety, restlessness, verbally disruptive behavior and resistance, such as lorazepam (Ativan™) and oxazepam (Serax™);
(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers, such as carbamazepine (Tegretol™) and divalproex (Depakote™);
(g) nicotinic apha—7 agonists;
(h) mGluR5 antagonists;
(i) H3 agonists; and
(j) amyloid therapy vaccines.

Thus, in one embodiment, the invention provides a pharmaceutical composition comprising:
i) a compound of the invention, or a pharmaceutically acceptable salt thereof;
ii) at least one compound selected from:
   a) acetylcholinesterase inhibitors,
   b) glutamate antagonists,
   c) antidepressant medications,
   d) anxiolytics,
   e) antipsychotic medications,
   f) mood stabilizers,
   g) nicotinic apha-7 agonists,
   h) mGluR5 antagonists,
   i) H3 agonists, and
   j) amyloid therapy vaccines; and
ii) one or more pharmaceutically acceptable carriers.

In another embodiment, the invention relates to a compound of the invention, or a pharmaceutically acceptable salt thereof, in combination with another therapeutic agent wherein the other therapeutic agent is selected from:
a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

Thus, in one embodiment, the invention provides a pharmaceutical composition comprising;
i) a compound of the invention, or a pharmaceutically acceptable salt thereof, and
ii) at least one compound selected from
   a) antidiabetic agents,
   b) hypolipidemic agents,
   c) anti-obesity agents,
   d) anti-hypertensive agents,
   e) agonists of peroxisome proliferator-activator receptors, and
ii) one or more pharmaceutically acceptable carriers.

Other specific anti-diabetic compounds are described by Patel Mona in *Expert Opin Investig Drugs*, 2003, 12(4), 623-633, in the FIGS. 1 to 7.

The structure of the therapeutic agents identified by code numbers, generic or trade names may be taken from the actual edition of the standard compendium "The Merck Index" or from databases, e.g., Patents International (e.g. IMS World Publications).

EXAMPLES

The following Examples illustrate the invention, but do not limit it.

| Abbreviations | |
|---|---|
| aq. | aqueous |
| anhy. | anhydrous |
| Boc | tert-butoxycarbonyl |
| Boc$_2$O | di-tert-butyl dicarbonate |
| t-Bu | tert-butyl |
| t-BuOH | tert-butanol |
| conc. | concentrated |
| (1R)-(−)-10-CSA | (1R)-(−)-10-Camphor sulphonic acid |
| DCM | dichloromethane |
| DEA | diethylamine |
| DIPEA | diisopropylethylamine |
| DMAP | 4-dimethyl amino pyridine |
| DMF | N,N-dimethylformamide |
| DMSO | dimethylsulfoxide |
| EDC | 1-(3-dimethylaminopropyl)-3-ethylcarbodiimide hydrochloride |
| eq. | equivalent(s) |
| ESI | electrospray ionisation |
| ETA | ethanol/conc. aq. ammonia 95/5 |
| Et$_3$N | triethylamine |
| Et$_2$O | diethylether |
| EtOAc | ethyl acetate |
| EtOH | ethanol |
| h | hour(s) |
| HOAt | 1-hydroxy-7-azabenzotriazole |
| HPLC | high performance liquid chromatography |
| LC | liquid chromatography |
| MeOH | methanol |
| min | minute(s) |
| MS | mass spectrometry |
| NEt$_3$ | triethylamine |
| NMR | nuclear magnetic resonance spectrometry |
| org | organic |
| Rf | retention factor |
| ROESY | Rotating-frame Overhauser Effect SpectroscopY |
| Rt | retention time (min) |
| rt | room temperature |
| soln. | solution |
| TBDMS | tertiary butyl dimethyl silyl |
| TBME | tert-butyl-methyl-ether |
| TFAA | trifluoroacetic acid anhydride |
| THF | tetrahydrofuran |
| TLC | thin layer chromatography |
| UPLC | ultra performance liquid chromatography |
| Xantphos | 4,5-bis(diphenylphosphino)-9,9-dimethylxanthene |

NMR Methodology

Proton spectra are recorded on a Bruker 400 MHz ultrashield spectrometer unless otherwise noted. Chemical shifts are reported in ppm relative to methanol ($\delta$ 3.31), dimethyl sulfoxide ($\delta$ 2.50), or chloroform ($\delta$ 7.29). A small amount of the dry sample (2-5 mg) is dissolved in an appropriate deuterated solvent (0.7 mL). The shimming is automated and the spectra obtained in accordance with normal procedure.

General Chromatography Information

HPLC Method H1 (Rt$_{H1}$):
HPLC-column dimensions: 3.0×30 mm
HPLC-column type: Zorbax SB-C18, 1.8 µm
HPLC-eluent: A) water+0.05 Vol.-% TFA; B) ACN+0.05 Vol.-% TFA
HPLC-gradient: 30-100% B in 3.25 min, flow=0.7 ml/min
HPLC Method H2 (Rt$_{H2}$):
HPLC-column dimensions: 3.0×30 mm HPLC-column type: Zorbax SB-C18, 1.8 μm
HPLC-eluent: A) water+0.05 Vol.-% TFA; B) ACN+0.05 Vol.-% TFA
HPLC-gradient: 0-100% B in 3.25 min, flow=0.7 ml/min
LCMS Method H3 (Rt$_{H3}$):
HPLC-column dimensions: 3.0×30 mm
HPLC-column type: Zorbax SB-C18, 1.8 μm
HPLC-eluent: A) water+0.05 Vol.-% TFA, B) ACN+0.05 Vol.-% TFA
HPLC-gradient: 10-100% B in 3.25 min, flow=0.7 ml/min
HPLCMS Method H4 (Rt$_{H4}$):
HPLC-column dimensions: 2.1×50 mm
HPLC-column type: Acquity HPLC HSS T3, 1.8 μm
HPLC-eluent: A) water+0.05 Vol.-% formic acid+3.75 mM ammonium acetate B) ACN+0.04 Vol.-% formic acid
HPLC-gradient: 2-98% B in 1.4 min, 98% B 0.75 min, flow=1.2 ml/min
HPLC-column temperature: 50° C.
UPLCMS Method H5 (Rt$_{H5}$):
HPLC-column dimensions: 2.1×50 mm
HPLC-column type: Acquity HPLC HSS T3, 1.8 μm
HPLC-eluent: A) water+0.1 Vol.-% formic acid, B) ACN+ 0.1% formic acid
HPLC-gradient: 10-95% B in 1.5 min, 1.0 min 95% B, flow=1.2 ml/min
HPLC-column temperature: 50° C.
LCMS method H6 (Rt$_{H6}$):
HPLC-column dimensions: 2.1×30 mm
HPLC-column type: Ascentis Express C18, 2.7 μm
HPLC-eluent: A) water+0.05 Vol.-% formic acid+0.05 ammonium acetate, B) ACN+0.04 Vol.-% formic acid
HPLC-gradient: 2-98% B in 1.4 min, 0.75 min 98% B, flow=1.2 ml/min
HPLC-column temperature: 50° C.
LCMS Method H7 (Rt$_{H7}$):
HPLC-column dimensions: 4.0×20 mm
HPLC-column type: Mercury MS Synergi, 2 μm
HPLC-eluent: A) water+0.1 Vol.-% formic acid, B) ACN
HPLC-gradient: 0.5 min 30% B, 30-95% B in 1 min, 0.9 min 95% B, flow=2.0 ml/min
HPLC-column temperature: 30° C.
LCMS Method H8 (Rt$_{H8}$):
HPLC-column dimensions: 4.0×20 mm
HPLC-column type: Mercury MS Synergi, 2 μm
HPLC-eluent: A) water+0.1 Vol.-% formic acid, B) ACN
HPLC-gradient: 0.5 min 70% B, 70-100% B in 1 min, 0.9 min 100% B, flow=2.0 ml/min
HPLC-column temperature: 30° C.
HPLC Method H9 (Rt$_{H9}$):
HPLC-column dimensions: 4.6×150 mm
HPLC-column type: Zorbax XDB-C18, 5 μm
HPLC-eluent: A) water+0.01 Vol.-% TFA; B) ACN/MeOH 1:1
HPLC-gradient: 1 min 30% B, 30-100% B in 5 min, 100-30% B in 4 min, flow=1.0 ml/min
HPLC-column temperature: 40° C.
HPLC Method H10 (Rt$_{H10}$):
HPLC-column dimensions: 4.6×150 mm
HPLC-column type: Zorbax XDB-C18, 5 μm
HPLC-eluent: A) water+0.01 Vol.-% TFA; B) ACN/MeOH 1:1
HPLC-gradient: 1 min 5% B, 5-100% B in 5 min, 100-5% B in 4 min, flow=1.0 ml/min
HPLC-column temperature: 40° C.
LCMS Method H11 (Rt$_{H11}$):
HPLC-column dimensions: 3.0×30 mm
HPLC-column type: Zorbax SB-C18, 1.8 μm
HPLC-eluent: A) water+0.05 Vol.-% TFA; B) ACN+0.05 Vol.-% TFA
HPLC-gradient: 70-100% B in 3.25 min, flow=0.7 ml/min
LCMS Method H12 (Rt$_{H12}$):
HPLC-column dimensions: 3.0×30 mm
HPLC-column type: Zorbax SB-C18, 1.8 μm
HPLC-eluent: A) water+0.05 Vol.-% TFA; B) ACN+0.05 Vol.-% TFA
HPLC-gradient: 80-100% B in 3.25 min, flow=0.7 ml/min
LCMS Method H13 (Rt$_{H13}$):
HPLC-column dimensions: 3.0×30 mm
HPLC-column type: Zorbax SB-C18, 1.8 μm
HPLC-eluent: A) water+0.05 Vol.-% TFA; B) ACN+0.05 Vol.-% TFA
HPLC-gradient: 40-100% B in 3.25 min, flow=0.7 ml/min Example 1

5-Bromo-pyridine-2-carboxylic acid [6-((R)-5-amino-3-methyl-3,6-dihydro-2H-[1,4]-oxazin-3-yl)-pyridin-2-yl]-amide

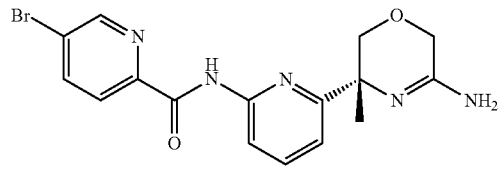 [SMILES: C[C@@]1(c2cccc(NC(=O)c3ccc(Br)cn3)n2)COCC(N)=N1]

a) 5-(6-Bromo-pyridin-2-yl)-5-methyl-imidazolidine-2,4-dione

To a solution of 1-(6-bromo-pyridin-2-yl)-ethanone (CAS 49669-13-8, 8.75 g, 43.7 mmol) and potassium cyanide (4.27 g, 65.6 mmol) in ethanol/water (40.0/26.7 ml) was added ammonium carbonate (21.02 g, 219.0 mmol). The reaction mixture was stirred in an autoclave at 100° C. for 17 h, then diluted with H$_2$O, 1M aq. NaHCO$_3$ soln. and EtOAc. The phases were separated and the aq. phase was reextracted with EtOAc, Et$_2$O and DCM. The combined org. phases were dried over Na$_2$SO$_4$, filtered and concentrated to leave the title compound as a pale white solid that was used in the next step without further purification. HPLC Rt$_{H4}$=0.62 min; ESIMS: 270, 272 [(M+H)$^+$]; $^1$H NMR (400 MHz, DMSO-d$_6$): δ 10.86 (br s, 1H), 8.48 (s, 1H), 7.81 (m, 1H), 7.64 (d, 1H), 7.57 (d, 1H), 1.68 (s, 3H).

b) 4-(6-Bromo-pyridin-2-yl)-4-methyl-2,5-dioxo-imidazolidine-1,3-dicarboxylic acid di-tert-butyl ester A solution of 5-(6-bromo-pyridin-2-yl)-5-methyl-imidazolidine-2,4-dione (22.8 g, 84.4 mmol), Boc$_2$O (58.8 ml, 55.3 g, 253.4 mmol) and DMAP (0.516 g, 4.22 mmol) in THF (600 ml) was stirred at rt for 4 h. The reaction mixture was concentrated to dryness, then taken up with EtOAc and filtered through silica. The silica cartridge was washed with EtOAc and THF, the combined filtrates were concentrated to leave the title compound as a pale yellow solid that was used in the next step without further purification.

HPLC Rt$_{H4}$=1.23 min; ESIMS: 470, 472 [(M+H)$^+$]; $^1$H NMR (400 MHz, CD$_3$OD): δ 7.82 (m, 1H), 7.65 (m, 2H), 2.11 (s, 3H), 1.60 (s, 9H), 1.30 (s, 9H).

c) 2-Amino-2-(6-bromo-pyridin-2-yl)-propionic acid

A solution of 4-(6-bromo-pyridin-2-yl)-4-methyl-2,5-dioxo-imidazolidine-1,3-dicarboxylic acid di-tert-butyl ester (31.53 g, 67.0 mmol) in 2.5M aq. NaOH soln. (215 ml) was refluxed for 40 h. The reaction mixture was diluted with EtOAc (100 ml) and filtered. The filtrates were separated and the org. layer was washed with $H_2O$. The combined aq. layers were evaporated to dryness to leave a solid that was suspended in MeOH (350 ml) and stirred for 30 min. The suspension was filtered and the white precipitate was washed with MeOH. The filtrates were evaporated to leave a pale orange solid which was used for the next step without further purification.

HPLC $Rt_{H4}$=0.35-0.37 min; ESIMS: 245, 247 [(M+H)+]; $^1$H NMR (400 MHz, CD$_3$OD): δ 7.60-7.51 (m, 2H), 7.36 (dd, 1H), 1.62 (s, 3H).

d) 2-Amino-2-(6-bromo-pyridin-2-yl)-propan-1-ol

To a suspension of 2-amino-2-(6-bromo-pyridin-2-yl)-propionic acid (25.5 g, 72.8 mmol) and Boc$_2$O (33.8 ml, 31.8 g, 145.7 mmol) in acetonitrile (300 ml) and methanol (150 ml) was added tetramethylammonium hydroxide (65.1 ml of a 25% aq. soln., 182 mmol). The reaction was allowed to stir at rt for 6.5 h and was filtered. The filtrates were washed with MeOH and CH$_3$CN, then evaporated to leave an orange solid which was triturated with DCM and brine. The phases were separated and the aq. phase was 3× extracted with DCM. The combined org. phases were concentrated to leave crude 2-(6-bromo-pyridin-2-yl)-2-tert-butoxycarbonylamino-propionic acid as a pale brown foam (HPLC $Rt_{H4}$=0.96-0.97 min, ESIMS: 345, 347 [(M+H)+]).

To a suspension of 2-(6-bromo-pyridin-2-yl)-2-tert-butoxycarbonylamino-propionic acid (14.1 g, 40.8 mmol) in THF (150 ml) was added portionwise NaBH$_4$ (3.45 g, 90.0 mmol) at 0° C. BF$_3$*Et$_2$O soln. (11.39 ml, 12.75 g, 90.0 mmol) was added dropwise over a period of 15 min and the reaction mixture was allowed to stir for 17 h at rt. In order to react remaining starting material, NaBH$_4$ (1.0 g, 26.43 mmol), and BF$_3$*Et$_2$O soln. (3.3 ml, 26.43 mmol) was added at 0° C. and the reaction mixture was stirred at rt for another 23 h. MeOH was added and the reaction mixture was stirred at 80° C. for 30 min, then cooled to rt and filtered. The filtrates were evaporated to leave a white foam which was taken up with EtOAc and 1N aq. NaOH soln. The phases were separated and the aq. phase was extracted three times with EtOAc. The combined org. phases were dried over Na$_2$SO$_4$, filtered and concentrated to leave [1-(6-bromo-pyridin-2-yl)-2-hydroxy-1-methyl-ethyl]-carbamic acid tert-butyl ester in a mixture with 2-amino-2-(6-bromo-pyridin-2-yl)-propan-1-ol. This mixture (7.5 g, 9.74 mmol) was rebocylated using Boc$_2$O (5.65 ml, 5.31 g, 24.34 mmol) and tetramethylammonium hydroxide (65.1 ml of a 25% aq. soln., 182 mmol) in acetonitrile (100 ml). After stirring for 1.5 h at rt, the reaction mixture was quenched with H$_2$O and diluted with EtOAc. The phases were separated and the aq. layer was twice reextracted with EtOAc. The combined org. layers were dried over Na$_2$SO$_4$, filtered and the solvent was removed to leave a yellow solid that was without further purification debocylated on a 8.1 g scale using 100 ml 4N aq. HCl. The reaction mixture was stirred at rt for 17 h, concentrated and the residue was taken up with H$_2$O and EtOAc. The phases were separated and the org. phase was washed with H$_2$O. The combined aq. phases were basified using 2N aq. NaOH soln. and then extracted with EtOAc. The phases were separated and the aq. phase was reextracted twice with EtOAc. The combined org. phases were dried over Na$_2$SO$_4$, filtered and concentrated to leave 2-amino-2-(6-bromo-pyridin-2-yl)-propan-1-ol as a colourless solid. HPLC $Rt_{H4}$=0.35 min; ESIMS: 231, 233 [(M+H)+]; $^1$H NMR (400 MHz, DMSO-d$_6$): δ 7.73-7.63 (m, 2H), 7.45 (dd, 1H), 4.72-4.69 (m, 1H), 3.58 (dd, 1H), 3.40 (dd, 1H), 2.00 (br s, 2H), 1.26 (s, 3H).

e) N-[1-(6-Bromo-pyridin-2-yl)-2-hydroxy-1-methyl-ethyl]-2-chloro-acetamide

To a solution of 2-amino-2-(6-bromo-pyridin-2-yl)-propan-1-ol (4.9 g, 21.2 mmol) in DCM (50 ml) was added K$_2$CO$_3$ (5.86 g, 42.4 mmol). The reaction mixture was cooled to 0° C. and 2-chloroacetyl chloride (2.55 ml, 3.59 g, 31.8 mmol) was added dropwise. The reaction mixture was allowed to warm to rt and to stir for 5 h. MeOH (20 ml) was added and stirring was continued at rt for 1 h. The reaction mixture was diluted with H$_2$O and DCM, the phases were separated and the aq. phase was twice extracted with DCM. The combined org. phases were dried over Na$_2$SO$_4$, filtered and the solvent was removed to leave N-[1-(6-bromo-pyridin-2-yl)-2-hydroxy-1-methyl-ethyl]-2-chloro-acetamide as an orange oil. HPLC $Rt_{H4}$=0.73-0.77 min; ESIMS: 307, 309 [(M+H)+]; $^1$H NMR (400 MHz, DMSO-d$_6$): δ 8.35 (s, 1H), 7.70-7.66 (m, 1H), 7.48 (dd, 1H), 7.38 (dd, 1H), 5.05-5.02 (m, 1H), 4.14 (s, 2H), 3.68-3.66 (m, 2H), 1.55 (s, 3H).

f) 5-(6-Bromo-pyridin-2-yl)-5-methyl-morpholin-3-one

To a solution of N-[1-(6-bromo-pyridin-2-yl)-2-hydroxy-1-methyl-ethyl]-2-chloro-acetamide in tert-butanol (90 ml) was added KOtBu and the reaction mixture was stirred at rt for 4 h. The reaction mixture was quenched with H$_2$O and diluted with EtOAc. The phases were separated and the aq. phase was twice extracted with EtOAc. The combined org. phases were washed with brine, dried over Na$_2$SO$_4$, filtered and the solvent was removed to leave the title compound as a pale yellow solid. HPLC $Rt_{H4}$=0.73 min; ESIMS: 271, 273 [(M+H)+]; $^1$H NMR (400 MHz, DMSO-d$_6$): δ 8.72 (s, 1H), 7.82-7.78 (m, 1H), 7.57-7.51 (m, 2H), 4.10 (d, 2H), 4.00 (d, 1H), 3.65 (d, 1H), 1.42 (s, 3H).

g) 5-(6-Bromo-pyridin-2-yl)-5-methyl-morpholine-3-thione

A mixture of 5-(6-bromo-pyridin-2-yl)-5-methyl-morpholin-3-one (4.65 g, 17.15 mmol) and P$_2$S$_5$ (4.57 g, 20.58 mmol) in pyridine (60 ml) was stirred at 80° C. under N$_2$ for 6 h. The reaction mixture was cooled to rt and diluted with 0.5N aq. HCl and EtOAc. The phases were separated and the aq. phase was twice extracted with EtOAc. The combined org. phases were washed with brine, dried over Na$_2$SO$_4$, filtered and concentrated. The title compound was obtained as a pale yellow solid after flash chromatography on silica gel (cyclohexane/EtOAc 100:0 to 75:25). HPLC $Rt_{H4}$=0.89 min; ESIMS: 287, 289 [(M+H)+]; $^1$H NMR (400 MHz, DMSO-d$_6$): δ 11.15 (s, 1H), 7.86-7.82 (m, 1H), 7.61 (dd, 1H), 7.39 (dd, 1H), 4.44-4.34 (d, 2H), 4.13 (d, 1H), 3.74 (d, 1H), 1.52 (s, 3H).

h) 5-(6-Bromo-pyridin-2-yl)-5-methyl-5,6-dihydro-2H-[1,4]oxazin-3-ylamine

A mixture of 5-(6-bromo-pyridin-2-yl)-5-methyl-morpholine-3-thione (1.4 g, 4.88 mmol) in 7N NH$_3$/MeOH (20.89 ml, 146 mmol) was stirred at 50° C. for 3 d in an autoclave. The reaction mixture was evaporated to dryness and purified by FC (gradient cyclohexane:EtOAc 75:25 to 50:50, then +10% Et$_3$N, finally MeOH+10% Et$_3$N) to obtain the crude title compound that was further purified by washing with DCM. HPLC $Rt_{H4}$=0.54 min; ESIMS: 270, 272 [(M+H)+];

$^1$H NMR (400 MHz, DMSO-d$_6$): δ 8.51 (br s, 2H), 7.83-7.79 (m, 1H), 7.63-7.61 (m, 2H), 4.45 (s, 2H), 4.11 (d, 1H), 3.84 (d, 1H), 1.51 (s, 3H).

i) [5-(6-Bromo-pyridin-2-yl)-5-methyl-5,6-dihydro-2H-[1,4]oxazin-3-yl]-carbamic acid tert-butyl ester A suspension of 5-(6-bromo-pyridin-2-yl)-5-methyl-5,6-dihydro-2H-[1,4]oxazin-3-ylamine (1.100 g, 4.07 mmol), Boc$_2$O (1.229 ml, 1.155 g, 5.29 mmol) and DIPEA (1.067 ml, 0.789 g, 6.11 mmol) in DCM (30 ml) was stirred at rt for 20 h. The reaction mixture was diluted with H$_2$O and DCM. The phases were separated and the aq. phase was twice reextracted with DCM. The combined org. phases were washed with brine, dried over Na$_2$SO$_4$, filtered and concentrated to yield the title compound as a colourless solid that was used in the next step without further purification. HPLC Rt$_{H4}$=0.92 min; ESIMS: 370, 372 [(M+H)$^+$].

j) (+)- and (−)-5-(6-Amino-pyridin-2-yl)-5-methyl-5,6-dihydro-2H-[1,4]oxazin-3-yl]-carbamic acid tert-butyl ester A mixture of [5-(6-Bromo-pyridin-2-yl)-5-methyl-5,6-dihydro-2H-[1,4]oxazin-3-yl]-carbamic acid tert-butyl ester (986 mg, 2.66 mmol), cyclohexanedimethyldiamine (0.420 ml, 379 mg, 2.66 mmol), sodium ascorbate (211 mg, 1.07 mmol), NaN$_3$ (1385 mg, 21.31 mmol) and CuI (203 mg, 1.07 mmol) in ethanol/water (22.0/8.8 ml) was degassed with N$_2$ in a dry ice/EtOH bath. The reaction mixture was then stirred at 45° C. for 4 h. The reaction mixture was allowed to warm to rt and filtered through hyflo, rinsed with EtOAc and concentrated. Flash chromatography on silica gel (cyclohexane/EtOAc gradient 0-3 min 100:0, 3-25 min 60:40, 40-52 min 50:50) yielded the title compound. HPLC Rt$_{H4}$=0.60, 0.66 min; ESIMS: 305 [(M−H)$^+$]; $^1$H NMR (400 MHz, DMSO-d$_6$): δ 7.77-7.73 (m, 1H), 6.81-6.76 (m, 2H), 4.71-4.63 (m, 1H), 4.70-4.56 (m, 2H), 4.06-3.96 (m, 2H), 1.69 (s, 3H), 1.51 (s, 9H).

Racemic 5-(6-amino-pyridin-2-yl)-5-methyl-5,6-dihydro-2H-[1,4]oxazin-3-yl]-carbamic acid tert-butyl ester was separated into the pure enantiomers by preparative chiral HPLC (column: Chiralpak AS; solvent: n-heptane/ethanol/isopropylamine=80:12:8; flow: 70 ml/min; detection at 220 nm). Enantiomer 1: [α]$_D$=−138.5° (c=1.00, MeOH). Enantiomer 2: [α]$_D$=+141.5° (c=1.03, MeOH). (−)-Enantiomer 1 was used for the following steps, its configuration was assigned (R) in analogy to similar structures of which the configuration has been determined by x-ray crystallography.

k) ((R)-5-{6-[(5-Bromo-pyridine-2-carbonyl)-amino]-pyridin-2-yl}-5-methyl-5,6-dihydro-2H-[1,4]oxazin-3-yl)-carbamic acid tert-butyl ester To a solution of 5-bromopyridine-2-carboxylic acid (34.5 mg, 0.171 mmol) in DCM (2 ml) was added 1-chloro-N,N,2-trimethylpropenylamine (0.045 ml, 45.7 mg, 0.342 mmol) and the reaction mixture was stirred at 0° C. for 1 h. The reaction mixture was then added dropwise to a dry solution of (−)-5-(6-amino-pyridin-2-yl)-5-methyl-5,6-dihydro-2H-[1,4]oxazin-3-yl]-carbamic acid tert-butyl ester (enantiomer 1 from procedure step j) above, 47.6 mg, 0.155 mmol) and NEt$_3$ (0.048 ml, 34.6 mg, 0.342 mmol) in DCM (2 ml) at 0° C. The reaction mixture was allowed to warm to rt and to stir for 20 min at rt. The reaction mixture was diluted with DCM and quenched with H$_2$O. The phases were separated and the aq. phase was extracted with DCM. The combined org. phases were washed with brine, dried over Na$_2$SO$_4$, filtered and twice purified by HPLC (Alltech Grom Saphir65 Si 10 μM column 150×30 mm, gradient 1 n-heptane:EtOAc 0-1.2 min 85:15, 1.2-9 min 0:100, 9-12 min 0:100, gradient 2 n-heptane:EtOAc:MeOH 0-1.2 min 47:50:3, 1.2-9 min 0:60:40, 9-12 min 0:60:40, flow 50 ml/min, detection 254 nm]. HPLC Rt$_{H4}$=1.10 min; ESIMS: 490, 492 [(M+H)$^+$].

l) 5-Bromo-pyridine-2-carboxylic acid [6-((R)-5-amino-3-methyl-3,6-dihydro-2H-[1,4]-oxazin-3-yl)-pyridin-2-yl]-amide To a solution of 5-{6-[(5-bromo-pyridine-2-carbonyl)-amino]-pyridin-2-yl}-5-methyl-5,6-dihydro-2H-[1,4]oxazin-3-yl)-carbamic acid tert-butyl ester (43 mg, 0.088 mmol) in DCM (270 μl) was added TFA (270 μl, 400 mg, 3.51 mmol) and the reaction mixture was stirred at rt for 1 h. The reaction mixture was quenched with 1M aq. NaHCO$_3$ soln. and diluted with DCM. The phases were separated and the aq. phase was twice reextracted with DCM. The combined org. phases were dried over Na$_2$SO$_4$, filtered, concentrated and purified by manual flash chromatography (NH$_3$-desactivated silica gel, hexane:DCM:MeOH 10:10:1 then DCM:MeOH 10:1, then +0.1% NH$_3$ and finally MeOH+1% NH$_3$) to yield the title compound as a colourless solid. To a solution of the free base in DCM was added 1 eq. 2N HCl/Et$_2$O and the resulting hydrochloride salt was collected. HPLC Rt$_{H4}$=0.76 min; ESIMS: 390, 392 [(M+H)$^+$]; $^1$H NMR (400 MHz, CD$_3$OD): δ 8.88 (d, 1H), 8.38 (d, 1H), 8.33 (dd, 1H), 8.27-8.24 (m, 1H), 8.24-7.98 (m, 1H), 7.33 (d, 1H), 4.69 (d, 1H), 4.67 (d, 1H), 4.30 (d, 1H), 4.11 (d, 1H), 1.78 (s, 3H).

Example 2

5-Bromo-pyridine-2-carboxylic acid [6-(5-amino-3-methyl-3,6-dihydro-2H-[1,4]-oxazin-3-yl)-pyridin-2-yl]-amide

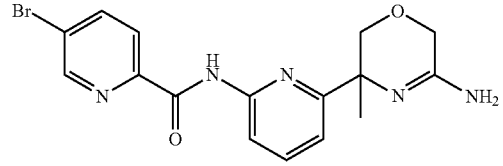 [SMILES: CC1(c2cccc(NC(=O)c3ccc(Br)cn3)n2)COCC(N)=N1]

The racemate of Example 1 can be prepared by a procedure analogous to that used in Example 1 completing the synthesis using the racemic mixture obtained in step j) of Example 1 and has the same analytical data.

Example 3

5-{6-[(5-Chloro-pyridine-2-carbonyl)-amino]-pyridin-2-yl}-5-fluoromethyl-5,6-dihydro-2H-[1,4]oxazin-3-yl-ammonium trifluoro acetate

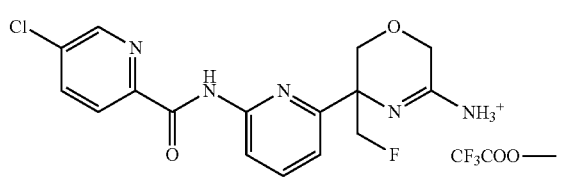

a) 2-(6-Bromo-pyridin-2-yl)-malonic acid diethyl ester

Lithium diisopropylamide (2.0 M solution in heptane/THF/ethyl benzene, 581.3 ml) was taken in dry THF (400 mL) and cooled to −78° C. 2-Bromo-6-methylpyridine (50.0 g, 296.64 mmol) was added slowly to the LDA solution at the same temperature for 15 min., allowed to stir constantly for 30 min. Ethylchloroformate (94.62 g, 871.94 mmol) in dry THF (50 ml) was then added to the stirred contents drop wise and allowed the reaction mass to stir at −78° C. for 2 h. Reaction mixture was quenched with saturated ammonium chloride solution and product formed was extracted with ethyl acetate by washing with water, brine and dried over anhy. $Na_2SO_4$. Organic layer was concentrated under reduced pressure and the crude product was purified by column chromatography using 10% ethyl acetate in hexane to furnish title compound as a brown colored liquid. Yield=65.0 g (71.4%). TLC (10% ethyl acetate in hexane) $R_f$=0.31; LCMS: $Rt_{H8}$=1.866; [M+1]=315.8 and 317.9; HPLC: $Rt_{H9}$=4.636 min (48%); $^1$H NMR (400 MHz, $CDCl_3$): δ 7.587 (t, 1H), 7.47 (d, 1H), 7.27 (d, 1H), 3.91 (s, 1H), 4.25-4.09 (m, 4H), 1.24 (t, 6H).

b) (6-Bromo-pyridin-2-yl)-acetic acid 2-(6-Bromo-pyridin-2-yl)-malonic acid diethyl ester (64.0 g, 202.4 mmol) was added to a solution of potassium carbonate (279.8 g, 2024 mmol) in water (400 ml) at rt and the reaction mixture was heated to reflux at 100° C. for 36 h. The reaction mixture was treated with sat. ammonium chloride solution and the product formed was extracted with ethyl acetate (3×800 ml), washed with brine (10 ml). Organic layer was concentrated under reduced pressure to obtain title compound as a pale brown solid. Yield=34.0 g (77.7%). TLC (50% ethyl acetate in hexane) $R_f$=0.11; LCMS: $Rt_{H8}$=0.45; [M+1]=216.0 and 218.0.

c) (6-Bromo-pyridin-2-yl)-acetic acid ethyl ester

To a solution of (6-bromo-pyridin-2-yl)-acetic acid (34.0 g, 158.14 mmol) in ethanol (300 ml) was added conc. $H_2SO_4$ (5.0 ml) and heated to reflux for 12 h. The reaction mixture was cooled to rt and concentrated under reduced pressure to dryness. Water was added to the residue and the product was extracted with ethyl acetate. Organic layer was washed with brine, dried over anhy. $Na_2SO_4$ and concentrated under reduced pressure to furnish the crude product. Column chromatography purification furnished the title compound as a brown liquid. Yield=31.2 g (82%). TLC (20% ethyl acetate in hexane) $R_f$=0.51; LCMS: $Rt_{H7}$=0.996, [M+1]$^+$=244.0 and 246.0; HPLC: $Rt_{H9}$=3.87 min (97.2%); $^1$H NMR (400 MHz, $CDCl_3$): δ 7.53 (t, 1H), 7.39 (d, 1H), 7.28 (d, 1H), 4.19 (q, 2H), 3.83 (s, 2H), 1.25 (t, 3H).

d) 2-(6-Bromo-pyridin-2-yl)-3-hydroxy-2-hydroxymethyl-propionic acid ethyl ester To the solution of para formaldehyde (9.6 g, 319.55 mmol) and sodium ethoxide (0.87 g, 12.784 mmol) in dry THF (250 ml) was added (6-bromo-pyridin-2-yl)-acetic acid ethyl ester (31.2 g, 127.82 mmol) at 0° C. to −10° C. and allowed the reaction mixture to stir at same temperature for 4 h. Solids formed in the reaction mixture were filtered and washed with ethyl acetate and the filtrate was concentrated to obtain crude product as a brown liquid. Yield=30.0 g (crude). TLC (30% ethyl acetate in hexane) $R_f$=0.28; LCMS: $Rt_{H8}$=0.702, M+1=304.0 and 306.0.

e) 2-(6-Bromo-pyridin-2-yl)-3-methoxymethoxy-2-methoxymethoxymethyl-propionic acid ethyl ester To the solution of 2-(6-bromo-pyridin-2-yl)-3-hydroxy-2-hydroxymethyl-propionic acid ethyl ester (30.0 g, 98.638 mmol) in dry THF (250 ml) was added tetrabutyl ammonium bromide (15.8 g, 49.319 mmol) and di-isopropyl ethyl amine (127.47 g, 163.0 ml) followed by methoxymethyl chloride was added drop wise at rt. Resultant reaction contents were refluxed at 65° C. for 3 h and cooled to rt. Reaction mixture was concentrated under reduced pressure and purified by column chromatography over silica gel using 10% ethyl acetate in hexane to furnish title compound as a brown liquid. Yield=20.4 g (52%). TLC (30% ethyl acetate in hexane) $R_f$=0.55; LCMS: $Rt_{H7}$=1.639, [M+1]$^+$=392.0 and 394.0; $^1$H NMR (400 MHz, $CDCl_3$): δ 7.49 (t, 1H), 7.35 (d, 1H), 7.22 (d, 1H), 4.62-4.47 (m, 4H), 4.24-4.16 (m, 6H), 3.25 (s, 6H), 1.23 (t, 3H).

f) 2-(6-Bromo-pyridin-2-yl)-3-methoxymethoxy-2-methoxymethoxymethyl-propionic acid Lithium hydroxide (10.69 g, 254.95 mmol) was added to a solution of 2-(6-bromo-pyridin-2-yl)-3-methoxymethoxy-2-methoxymethoxymethyl-propionic acid ethyl ester (20.0 g, 50.99 mmol) in ethanol (100 ml) and water (100 ml) at rt and the reaction mixture was allowed to stir overnight. The reaction mass was concentrated under reduced pressure and acidified with dilute HCl and at 0° C. The product was extracted with ethyl acetate, washed with minimum amount of brine. Organic layer was concentrated under reduced pressure to obtain title compound as a brown liquid. Yield=18.0 g. TLC (50% ethyl acetate in hexane) $R_f$=0.05; LCMS: $Rt_{H9}$=1.383, [M+1]=364.0 and 366.0; HPLC: $Rt_{H9}$=3.844 min (49%) and 3.885 min. (22%).

g) 1-(6-Bromo-pyridin-2-yl)-2-methoxymethoxy-1-methoxymethoxymethyl-ethylamine To a suspension of 2-(6-bromo-pyridin-2-yl)-3-methoxymethoxy-2-methoxymethoxymethyl-propionic acid (18.0 g) in toluene (150 ml) diphenyl phosphoryl azide (4.08 g, 148.27 mmol) and triethylamine (14.97 g [20.6 ml], 148.27 mmol) were added at rt and stirred at 100° C. for 15 h. Reaction mixture was cooled to rt and concentrated under reduced pressure. The residue obtained was dissolved in THF (600 ml) and 20% NaOH solution was added at rt and stirred for 1 h. Solvent was removed under reduced pressure and the product formed was extracted with ethyl acetate. Organic layer was washed with brine, followed by dried over $MgSO_4$. The organic portion was concentrated under reduced pressure and column chromatographic purification of the crude product using 35% ethyl acetate in hexane furnished title compound as a brown liquid. Yield=15.0 g (88% [2 steps]). TLC (70% ethyl acetate in hexane) $R_f$=0.51; LCMS: $Rt_{H7}$=0.28, [M+1]=335.0 and 337.0.

h) N-[1-(6-Bromo-pyridin-2-yl)-2-methoxymethoxy-1-methoxymethoxymethyl-ethyl]-2-chloro-acetamide To a solution of 1-(6-bromo-pyridin-2-yl)-2-methoxymethoxy-1-methoxymethoxymethyl-ethylamine (15.0 g, 44.75 mmol) in DCM (150 ml) was added aqueous $Na_2CO_3$ solution (10.91 g, 102.925 mmol in water, 30 ml) was added at 0° C. and stirred for 10 min. Chloroacetylchloride (5.56 g, 49.225 mmol) was added to the resultant reaction mixture at 0° C. stirring continued for 1 h at ambient temperature. Reaction mixture was diluted with DCM (~1 l), and worked up the reaction mixture by washing with water, brine and dried over anhy. $Na_2SO_4$. Organic layer was separated and concentrated under reduced pressure to obtain title compound as a brown liquid. Yield=9.0 g (48%). TLC (50% ethyl acetate in hexane) $R_f$=0.54; LCMS: $Rt_{H7}$=1.341, [M+1]=411.0 and 413.0; HPLC: $Rt_{H9}$=4.27 min (50.4%); $^1$H NMR (400 MHz, CDCl$_3$): δ 8.11 (d, 1H), 7.57-7.52 (m, 1H), 7.46-7.37 (m, 2H), 4.59-4.52 (m, 4H), 4.23-4.17 (m, 4H), 4.09-4.04 (m, 2H), 3.21 (s, 6H).

i) N-[1-(6-Bromo-pyridin-2-yl)-2-hydroxy-1-hydroxymethyl-ethyl]-2-chloro-acetamide To a solution of N-[1-(6-bromo-pyridin-2-yl)-2-methoxymethoxy-1-methoxymethoxymethyl-ethyl]-2-chloro-acetamide (9.0 g, 21.861 mmol) in ethanethiol (30 ml) and BF$_3$.Et$_2$O (9.3 g, 141.93 mmol) was added at 0° C. and stirred for 10 min. Stirring was continued for 3 h at rt. Reaction mixture was quenched with saturated NaHCO$_3$ solution and the product formed was extracted with ethyl acetate. Organic layer was separated and washed with brine solution, followed by drying over anhydrous Na$_2$SO$_4$. Organic layer was concentrated under reduced pressure and purified by column chromatography using 2% methanol in chloroform to obtain title compound as a brown liquid. Yield=5.5 g (77%). TLC (10% methanol in chloroform) $R_f$=0.51; LCMS: $Rt_{H8}$=0.916, [M+1]=322.9 and 324.8; HPLC $Rt_{H9}$=5.931 min (89%); $^1$H NMR (400 MHz, CDCl$_3$): δ 8.27 (s, 1H), 7.56 (t, 1H), 7.42-7.39 (m, 2H), 4.38 (s, 2H), 4.09-4.07 (m, 4H), 3.95 (d, 2H).

j) 5-(6-Bromo-pyridin-2-yl)-5-hydroxymethyl-morpholin-3-one

To the solution of N-[1-(6-bromo-pyridin-2-yl)-2-hydroxy-1-hydroxymethyl-ethyl]-2-chloro-acetamide (5.4 g, 16.69 mmol) in t-BuOH (80 ml) was added t-BuOK (2.06 g, 18.38 mmol) at rt followed by sodium iodide (0.25 g, 1.669 mmol) and allowed the reaction mixture to stir at 90° C. for 1 h. The reaction mixture was concentrated under reduced pressure and the residue obtained was treated with water. Compound present in the residue was extracted with ethyl acetate (2×100 ml). Organic portion was washed with brine, dried over Na$_2$SO$_4$ and concentrated under reduced pressure to obtain gummy compound. Further trituration of the formed product with n-pentane (5.0 ml) and diethyl ether (5.0 ml) furnished title compound as a pale yellow gummy compound. Yield=3.3 g (68.8%). TLC (50% ethyl acetate in hexane) $R_f$=0.21; LCMS: $Rt_{H8}$=0.155, [M+1]=286.9 and 288.8; HPLC $Rt_{H9}$=3.03 min (69.8%); $^1$H NMR (400 MHz, CDCl$_3$): δ 8.40 (s, 1H), 7.79 (t, 1H), 7.57 (d, 2H), 5.11 (s, 1H), 4.15 (d, 1H), 3.99 (d, 2H), 3.88 (d, 1H), 3.71-3.60 (m, 2H).

k) 5-(6-Bromo-pyridin-2-yl)-5-fluoromethyl-morpholin-3-one

To a solution of 5-(6-bromo-pyridin-2-yl)-5-hydroxymethyl-morpholin-3-one (2.8 g, 9.756 mmol) in dry THF (30 ml), diethylamino sulfur trifluoride (4.72 g, 29.268 mmol) was added at rt and stirring continued for 4 h. Na$_2$CO$_3$ was then added to the resultant reaction mixture and stirred for further 30 min. The reaction mixture was concentrated under reduced pressure and the product was extracted with ethyl acetate. Organic layer was washed with brine, dried over anhy. Na$_2$SO$_4$ and concentrated under reduced pressure to obtain crude compound as gummy residue. Purification of the crude product with 45% ethyl acetate in hexane solvent system furnished the title compound as off-white solid. Yield=1.15 g (40%). TLC (70% ethyl acetate in hexane) $R_f$=0.49; LCMS: $Rt_{H7}$=0.383, [M+1]$^+$=289 and 289; HPLC $Rt_{H9}$=3.27 min (84%); $^1$H NMR (400 MHz, CDCl$_3$): δ 7.62 (t, 1H), 7.49 (dd, 1H), 7.32 (d, 1H), 7.09 (br. s, 1H), 4.92 (dd, 1H), 4.52 (dd, 1H), 4.32-4.17 (m, 3H), 3.98-3.93 (dd, 1H); $^{19}$F NMR (376.2 MHz): δ−255.65 (t, 1F).

l) 5-Chloro-pyridine-2-carboxylic acid [6-(3-fluoromethyl-5-oxo-morpholin-3-yl)-pyridin-2-yl]-amide A mixture of 4,5-Bis(diphenyl phosphino)-9,9-dimethyl xanthene (0.04 g, 0.069 mmol), tris(dibenzylidene-acetone) di palladium(0) (0.032 g, 0.035 mmol) and cesium carbonate (0.678 g, 2.083 mmol) were taken in 1,4-dioxane and degassed with argon for 10 min. 5-(6-Bromo-pyridin-2-yl)-5-fluoromethyl-morpholin-3-one (0.2 g, 0.694 mmol) followed by 5-chloropicolinamide (0.119 g, 0.764 mmol) were added to the resultant reaction mixture and degassed with argon for further 5 min. Reaction mixture was then heated at 80° C. for 16 h and cooled to rt. Reaction contents were treated with water and product was extracted with ethyl acetate, washed with brine and dried over anhy. Na$_2$SO$_4$. The organic layer was concentrated under reduced pressure to obtain liquid which was triturated with n-pentane to furnish title compound as a off-white solid. Yield=0.24 g (crude). TLC (50% ethyl acetate in hexane) $R_f$=0.45; LCMS: $Rt_{H8}$=1.215, [M+1]=365.1 and 366.9; HPLC $Rt_{H9}$=4.367 min (53 m) 5-Chloro-pyridine-2-carboxylic acid [6-(3-fluoromethyl-5-thioxo-morpholin-3-yl)-pyridin-2-yl]-amide To a solution of 5-chloro-pyridine-2-carboxylic acid [6-(3-fluoromethyl-5-oxo-morpholin-3-yl)-pyridin-2-yl]-amide (0.24 g, 0.658 mmol) in THF (10.0 ml), Lawesson's reagent (0.798 g, 1.974 mmol) was added at rt and heated at reflux temperature for 24 h. Reaction mass was concentrated under reduced pressure. The crude compound was directly purified by column chromatography using 23% ethyl acetate in hexane to furnish title compound as off-white solid. Yield=0.19 g (72% [2 steps]). TLC (50% ethyl acetate in hexane) $R_f$=0.71; LCMS: $Rt_{H8}$=1.578, [M+1]$^+$=381.1 and 382.9.

n) 5-{6-[(5-Chloro-pyridine-2-carbonyl)-amino]-pyridin-2-yl}-5-fluoromethyl-5,6-dihydro-2H-[1,4] oxazin-3-yl-ammonium trifluoro acetate To a solution of 5-chloro-pyridine-2-carboxylic acid [6-(3-fluoromethyl-5-thioxo-morpholin-3-yl)-pyridin-2-yl]-amide (0.19 g, 0.499 mmol) in methanol (2.0 ml), 10% ammonia in methanol (8.0 ml) was added at 0° C. in a sealed tube and stirred at rt for 24 h. Reaction mass was concentrated under reduced pressure and directly purified by preparative HPLC. Conditions: column: C18-ZORBAX 21.2×150 mm; 5 μm. mobile phase: 0.1% TFA in water (A)/ACN; flow: 20 ml/min. Yield: 86 mg (36%). M.P: 216-218° C. TLC (20% methanol in chloroform) $R_f$=0.45; LCMS: $Rt_{H8}$=0.194 [M+1]=364.0 and 366.1; HPLC $Rt_{H9}$=3.222 min (98.7%); $^1$H NMR (400 MHz, DMSO-d$_6$): δ 10.85 (s, 1H), 10.37 (s, 1H), 9.37 (s, 1H), 8.50-8.79 (m, 2H), 8.31-8.23 (m, 3H), 8.06 (t, 1H), 7.37 (d, 1H), 4.96 (dd, 1H), 4.85 (dd, 1H), 4.62 (dd, 2H), 4.25-4.16 (m, 2H). Product formation was also confirmed by 2D NMR-ROESY.

Examples 4 to 7

The compounds listed in Table 4 were prepared by a procedure analogous to those used in Example 3.

TABLE 4

| Example | Compound | $^1$H-NMR (δ; DMSO-$d_6$) | MS [m/z; (M + 1)$^+$] |
|---|---|---|---|
| 4 | 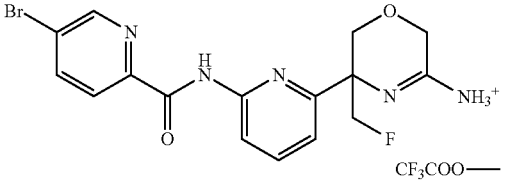 5-{6-[(5-Bromo-pyridine-2-carbonyl)-amino]-pyridin-2-yl}-5-fluoromethyl-5,6-dihydro-2H-[1,4]oxazin-3-yl-ammonium trifluoro acetate | 10.74 (s, 1H), 10.34 (s, 1H), 9.35 (s, 1H), 8.92 (t, 1H), 8.69 (s, 1H), 8.39 (dd, 1H), 8.29 (dd, 1H), 8.17 (dd, 1H), 8.05 (t, 1H), 7.36 (d, 1H), 4.96 (dd, 1H), 4.86 (dd, 1H), 4.62 (dd, 2H), 4.25-4.15 (m, 2H). | LCMS: Rt$_{H8}$ = 0.239 [M + 1] = 408.0, 410.0 |
| 5 | 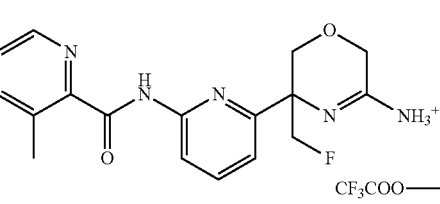 5-{6-[(5-Cyano-3-methyl-pyridine-2-carbonyl)-amino]-pyridin-2-yl}-5-fluoromethyl-5,6-dihydro-2H-[1,4]oxazin-3-yl-ammonium trifluoro acetate | 9.01 (s, 1H), 8.43 (s, 1H), 8.11 (d, 1H), 7.874 (t, 1H), 7.40 (d, 1H), 4.59-4.45 (m, 2H), 4.03-3.85 (m, 6H), 2.61 (s, 3H), 1.89 (s, 3H). | LCMS: Rt$_{H8}$ = 0.127; [M + 1] = 369.4 |
| 6 | 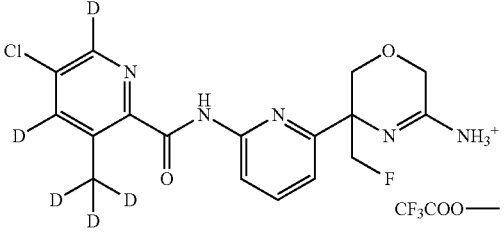 5-{6-[(4,6-Dideutero-5-chloro-3-trideuteromethyl-pyridine-2-carbonyl)-amino]-pyridin-2-yl}-5-fluoromethyl-5,6-dihydro-2H-[1,4]oxazin-3-yl-ammonium trifluoro acetate | 10.80 (s, 1H), 10.54 (s, 1H), 9.35 (s, 1H), 8.76 (s, 1H), 8.25 (d, 1H), 8.02 (t, 1H), 7.33 (d, 1H), 4.99-4.76 (m, 2H), 4.61 (m, 2H), 4.18 (t, 2H). | LCMS: Rt$_{H8}$ = 0.208; [M + 1] = 383.3 |
| 7 | 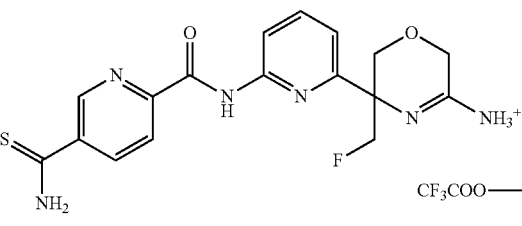 5-{6-[(5-Thiocarbamoyl-pyridine-2-carbonyl)-amino]-pyridin-2-yl}-5-fluoromethyl-5,6-dihydro-2H-[1,4]oxazin-3-yl-ammonium trifluoro-acetate | 10.82 (s, 1H), 10.46 (s, 1H), 10.33 (s, 1H), 9.96 (s, 1H), 9.36 (s, 1H), 90.1-9.09 (m, 1H), 8.73 (s, 1H), 8.44 (dd, 1H), 8.28 (dd, 2H), 8.06 (t, 1H), 7.37 (d, 1H), 5.03-4.78 (m, 2H), 4.61 (dd, 2H), 4.26-4.16 (m, 2H). | LCMS: Rt$_{H7}$ = 0.153; [M + 1] = 389.1 |

Example 8

5-Cyano-3-methyl-pyridine-2-carboxylic acid [6-((3R,6R)-5-amino-3,6-dimethyl-6-trifluoro-methyl-3,6-dihydro-2H-[1,4]oxazin-3-yl)-pyridin-2-yl]-amide

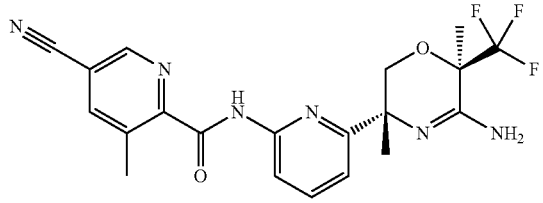 [SMILES: Cc1cc(C#N)cnc1C(=O)Nc1cccc([C@]2(C)CO[C@@](C)(C(F)(F)F)C(N)=N2)n1]

a) 4-(6-Bromo-pyridin-2-yl)-4-methyl-2-oxo-2lambda*4*-[1,2,3]oxathiazolidine-3-carboxylic acid tert-butyl ester To an at 0° C. precooled solution of thionyl chloride (3.42 ml, 5.57 g, 46.8 mmol) in pyridine (9.46 ml, 9.25 g, 117.0 mmol) was added dropwise a solution of [1-(6-bromo-pyridin-2-yl)-2-hydroxy-1-methyl-ethyl]-carbamic acid tert-butyl ester (see Example 1 step d), 7.75 g, 23.4 mmol) in DCM (230 ml). The reaction mixture was allowed to stir for 1 h at rt, then 0.5 N aq. HCl and DCM were added, the phases were separated and the aq. phase was twice reextracted with DCM. The combined org. phases were washed with brine, dried over $Na_2SO_4$, filtered and concentrated to leave the title compound (mixture of diastereomers) as an orange solid. HPLC $Rt_{H4}$=1.16, 1.20 min (diastereomers); ESIMS: 377, 379 [(M+H)$^+$].

b) 4-(6-Bromo-pyridin-2-yl)-4-methyl-2,2-dioxo-2lambda*6*-[1,2,3]oxathiazolidine-3-carboxylic acid tert-butyl ester To a solution of 4-(6-bromo-pyridin-2-yl)-4-methyl-2-oxo-2lambda*4*-[1,2,3]oxathiazolidine-3-carboxylic acid tert-butyl ester (8.83 g, 23.4 mmol) in acetonitrile (60 ml) and $H_2O$ (30.0 ml) was added $RuCl_3$ hydrate (0.971 g, 4.68 mmol) and $NaIO_4$ (10.01 g, 46.8 mmol). The reaction mixture was stirred at 0° C. for 2 h. $H_2O$ and DCM were added, the phases were separated and the aq. phase was twice reextracted with DCM. The combined org. phases were washed with brine, dried over $Na_2SO_4$, filtered and concentrated. The residue was dissolved in DCM and filtered through silica gel, the filtrate was evaporated and the residue was triturated with TBME (10 ml) and n-hexane (100 ml). The resulting precipitate was filtered and washed with n-hexane to yield the title compound as a colourless crystalline solid. HPLC $Rt_{H4}$=1.16 min; ESIMS: 393, 395 [(M+H)$^+$]; $^1$H NMR (400 MHz, $CDCl_3$): δ 7.63-7.59 (m, 1H), 7.47-7.42 (m, 2H), 4.73 (d, 1H), 4.47 (d, 1H), 2.00 (s, 3H), 1.52 (s, 9H).

c) (R)-2-[(RS)-2-(6-Bromo-pyridin-2-yl)-2-tert-butoxycarbonylamino-propoxy]-3,3,3-trifluoro-2-methyl-propionic acid ethyl ester At 0° C., NaH (0.508 g of a 60% dispersion in mineral oil, 12.69 mmol) was added to a solution of 4-(6-bromo-pyridin-2-yl)-4-methyl-2,2-dioxo-2lambda*6*-[1,2,3]oxathiazolidine-3-carboxylic acid tert-butyl ester (3.84 g, 9.76 mmol) and (R)-3,3,3-trifluoro-2-hydroxy-2-methyl-propionic acid ethyl ester (2.54 g, 13.67 mmol) in DMF (10 ml, soln. pre-dried over 4 Å mol. sieves). The reaction mixture was allowed to stir at rt for 30 min, then at 60° C. for 17 h. The reaction mixture was quenched with $H_2O$ and diluted with 1N aq. HCl and EtOAc. The phases were separated and the aq. phase was twice reextracted with EtOAc. The combined org. phases were washed with brines, dried over $Na_2SO_4$, filtered and concentrated. Flash chromatography on silica gel (cyclohexane: EtOAc, gradient 0-5 min 100:0, 5-30 min 90:10, 30-40 min 90:10, 40-50 min 80:20, 50-55 min 80:20) yielded the title compound (diastereomer mixture) as a clear oil. HPLC $Rt_{H4}$=1.39 min; ESIMS: 499, 501 [(M+H)$^+$].

d) [(RS)-1-(6-Bromo-pyridin-2-yl)-2-(R)-1-carbamoyl-2,2,2-trifluoro-1-methyl-ethoxy)-1-methyl-ethyl]-carbamic acid tert-butyl ester A solution of (R)-2-[(RS)-2-(6-bromo-pyridin-2-yl)-2-tert-butoxycarbonylamino-propoxy]-3,3,3-tri-fluoro-2-methyl-propionic acid ethyl ester (3.0 g, 6.01 mmol) in 7N $NH_3$/MeOH (6.5 ml) was stirred in a sealed glass vial at 55° C. for 72 h. The reaction mixture was concentrated to leave the title compound as a colourless solid that was used in the next step without further purification. HPLC $Rt_{H4}$=1.12, 1.14 min (diastereomers); ESIMS: 470, 472 [(M+H)$^+$].

e) [(RS)-1-(6-Bromo-pyridin-2-yl)-2-(R)-1-cyano-2,2,2-trifluoro-1-methyl-ethoxy)-1-methyl-ethyl]-carbamic acid tert-butyl ester To an at 0° C. percooled solution of [(RS)-1-(6-bromo-pyridin-2-yl)-2-((R)-1-carbamoyl-2,2,2-trifluoro-1-methyl-ethoxy)-1-methyl-ethyl]-carbamic acid tert-butyl ester (2.18 g, 4.64 mmol) and $NEt_3$ (1.615 ml, 1.173 g, 11.59 mmol) in DCM (30 ml) was added dropwise TFAA (0.773 ml, 1.168 g, 5.56 mmol). After stirring for 5 min at 0° C., then for 1 h at rt the reaction mixture was diluted with sat. aq. $Na_2CO_3$ soln. and with DCM. The phases were separated and the aq. phase was twice reextracted with DCM. The combined org. phases were dried over $Na_2SO_4$, filtered and concentrated to leave a pale yellow oil which was stirred with 7N $NH_3$/MeOH for 5 min. The mixture was evaporated to dryness and purified by flash chromatography (cyclohexane: EtOAc 0-3 min 100:0, 3-35 min 65:35) to yield the title compound as a clear oil. HPLC $Rt_{H4}$=1.30 min; ESIMS: 452, 454 [(M+H)$^+$]; $^1$H NMR (400 MHz, $CDCl_3$): δ 7.59-7.53 (m, 1H), 7.42-7.36 (m, 2H), 5.66 (br s, 1H), 4.41-4.31 (m, 1H), 4.25-4.18 (m, 1H), 1.71 (d, 3H), 1.66 (d, 3H), 1.43 (s, 9H).

f) (R)-2-[(RS)-2-Amino-2-(6-bromo-pyridin-2-yl)-propoxy]-3,3,3-trifluoro-2-methyl-propionitrile A solution of [(RS)-1-(6-bromo-pyridin-2-yl)-2-((R)-1-cyano-2,2,2-trifluoro-1-methyl-ethoxy)-1-methyl-ethyl]-carbamic acid tert-butyl ester (0.456 g, 1.008 mmol) and TFA (1.554 ml, 2.299 g, 20.17 mmol) in DCM (5 ml) was stirred at rt for 30 min, concentrated and triturated with 7N $NH_3$/MeOH at rt for 20 min and again concentrated to give the title compound that was used for the next step without further purification. HPLC $Rt_{H4}$=0.69, 0.73 min (diastereomers); ESIMS: 352, 354 [(M+H)$^+$].

g) (2R,5RS)-5-(6-Bromo-pyridin-2-yl)-2,5-dimethyl-2-trifluoromethyl-5,6-dihydro-2H-[1,4]oxazin-3-ylamine A suspension of (R)-2-[(RS)-2-amino-2-(6-bromo-pyridin-2-yl)-propoxy]-3,3,3-trifluoro-2-methyl-propionitrile (0.688 g, 1.172 mmol), N-acetyl-L-cysteine (0.383 g, 2.344 mmol) and K$_2$CO$_3$ (0.356 g, 2.560 mmol) in abs. EtOH (4 ml) was stirred at 80° C. for 18 h. The reaction mixture was quenched with 10% aq. K$_2$CO$_3$ soln. and 3× extracted with TBME. The combined org. phases were washed with brine, dried over Na$_2$SO$_4$, filtered and concentrated to leave the title compound as a colourless solid. HPLC Rt$_{H4}$=0.68-0.70 min; ESIMS: 352, 354 [(M+H)$^+$].

h) [(2R,5R)-5-(6-Bromo-pyridin-2-yl)-2,5-dimethyl-2-trifluoromethyl-5,6-dihydro-2H-[1,4]oxazin-3-yl]-carbamic acid tert-butyl ester and (2R,5S)-diastereomer A mixture of (R)-5-(6-Bromo-pyridin-2-yl)-2,5-dimethyl-2-trifluoromethyl-5,6-dihydro-2H-[1,4]oxazin-3-ylamine, Boc$_2$O and DIPEA in DCM (4 ml) was stirred at rt for 20 h. The reaction mixture was quenched with sat. aq. NaHCO$_3$ soln. and diluted with DCM. The phases were separated and the aq. phase was twice reextracted with DCM. The combined org. phases were washed with brine, dried over Na$_2$SO$_4$, filtered and concentrated. HPLC purification (Alltech Grom Saphir 65 Si, 10 μm, 250×50 mm column, gradient Hept:EtOAc 0-1.6 min 85:15, 1.6-16 min 0:100, 16-21.2 min 0:100, flow: 100 ml/min, detection: 254 nm) yielded the desired (2R,5R) as well as the undesired (2R,5S)diastereomer. HPLC Rt$_{H4}$=1.28 min (2R,5S), 1.30 min (2R,5R); ESIMS: 452, 454 [(M+H)$^+$]; $^1$H NMR (2R,5R) (400 MHz, CDCl$_3$): δ 10.98 (br s, 1H), 7.59 (t, 1H), 7.43 (d, 1H), 7.34 (d, 1H), 4.39 (d, 1H), 4.08 (d, 1H), 1.62 (s, 3H), 1.55 (s, 12H); $^1$H NMR (2R,5S) (400 MHz, CDCl$_3$): δ 11.01 (br s, 1H), 7.57 (t, 1H), 7.42 (d, 1H), 7.37 (d, 1H), 4.45 (d, 1H), 3.91 (d, 1H), 1.74 (s, 3H), 1.65 (s, 3H), 1.55 (s, 19H).

i) ((2R,5R)-5-{6-[(5-Cyano-3-methyl-pyridine-2-carbonyl)-amino]-pyridin-2-yl}-2,5-dimethyl-2-trifluoromethyl-5,6-dihydro-2H-[1,4]oxazin-3-yl)-carbamic acid tert-butyl ester A mixture of [(2R,5R)-5-(6-Bromo-pyridin-2-yl)-2,5-dimethyl-2-trifluoromethyl-5,6-dihydro-2H-[1,4]oxazin-3-yl]-carbamic acid tert-butyl ester (60.00 mg, 0.133 mmol), 5-cyano-3-methylpicolinamide (23.52 mg, 0.146 mmol), Xantphos (6.91 mg, 0.012 mmol) and Cs$_2$CO$_3$ (60.50 mg, 0.186 mmol) in dioxane (0.611 ml) was degassed with argon for 5 min, then Pd$_2$dba$_3$ (3.64 mg, 3.98 μmol) was added and the reaction mixture was stirred at 40° C. for 18 h. The reaction mixture was diluted with H$_2$O and TBME. The phases were separated and the aq. phase was reextracted with TBME. The combined org. phases were washed with brine, dried over Na$_2$SO$_4$, filtered and concentrated. HPLC purification (Alltech Grom Saphir 65 Si 10 μM column, 150×30 mm, gradient n-heptane:EtOAc 0-1.2 min 75:25, 1.2-9 min 0:100, 9-12 min 0:100, flow: 50 ml/min, detection: 254 nm) yielded the title compound as a colourless solid. HPLC Rt$_{H4}$=1.37 min; ESIMS: 533 [(M+H)$^+$]; $^1$H NMR (400 MHz, CDCl$_3$): δ 11.22 (s, 1H), 10.47 (s, 1H), 8.78 (d, 1H), 8.33 (d, 1H), 7.98 (d, 1H), 7.84-7.80 (m, 1H), 7.13 (d, 1H), 4.37 (d, 1H), 4.11 (d, 1H), 2.88 (s, 3H), 1.64 (s, 3H), 1.57 (br s, 12H).

j) 5-Cyano-3-methyl-pyridine-2-carboxylic acid [6-((3R,6R)-5-amino-3,6-dimethyl-6-trifluoro-methyl-3,6-dihydro-2H-[1,4]oxazin-3-yl)-pyridin-2-yl]-amide To a solution of ((2R,5R)-5-{6-[(5-cyano-3-methyl-pyridine-2-carbonyl)-amino]pyridin-2-yl}-2,5-dimethyl-2-trifluoromethyl-5,6-dihydro-2H-[1,4]oxazin-3-yl)-carbamic acid tert-butyl ester (50.0 mg, 0.094 mmol) in DCM (0.3 ml) was added TFA (0.289 ml, 428.0 mg, 3.760 mmol) and the reaction mixture was stirred at rt for 2 h. The solvent was evaporated off, sat. aq. NaHCO$_3$ soln. and TBME was added, the phases were separated and the aq. phase was reextracted twice with TBME. The combined org. phases were dried over Na$_2$SO$_4$, filtered and concentrated and the residue was washed with MeOH to leave the title compound as a colourless crystalline solid. HPLC Rt$_{H4}$=0.84 min; ESIMS: 433 [(M+H)$^+$]; $^1$H NMR (400 MHz, CD$_3$OD): δ 8.85 (s, 1H), 8.21-8.18 (m, 2H), 7.82-7.78 (m, 1H), 7.23 (d, 1H), 4.18 (d, 1H), 3.80 (d, 1H), 2.76 (s, 3H), 1.46-1.45 (2s, 6H).

Examples 9 and 10

The compounds listed in Table 5 can be prepared by a procedure analogous to that used in Example 8.

Hydrochloride salts were obtained from solutions of the corresponding free base by addition of hydrochloric acid in dioxane or hydrochloric acid in diethylether and evaporation of the solvents.

TABLE 5

| Example | Compound | $^1$H-NMR | MS [m/z; (M + 1)$^+$] |
|---|---|---|---|
| 9 | 5-Cyano-pyridine-2-carboxylic acid [6-((3S,6R)-5-amino-3,6-dimethyl-6-trifluoromethyl-3,6-dihydro-2H-[1,4]oxazin-3-yl)-pyridin-2-yl]-amide hydrochloride | (δ; CDCl$_3$): 10.26 (br s, 1H), 8.97 (br s, 1H), 8.45 (d, 1H), 8.29-8.12 (m, 2H), 7.78-7.76 (m, 1H), 7.38 (d, 1H), 4.14 (d, 1H), 3.94 (d, 1H), 1.69 (br s, 3H), 1.55 (br s, 3H). | UPLCMS: Rt$_{H4}$ = 0.77 [M + 1] = 419.3 |

| Example | Compound | ¹H-NMR | MS [m/z; (M + 1)⁺] |
|---|---|---|---|
| 10 | 5-Cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide | (δ; CD₃OD): 9.07 (d, 1H), 8.45-8.39 (m, 2H), 8.22 (d, 1H), 7.83 (t, 1H), 7.27 (d, 1H), 4.19 (d, 1H), 3.83 (d, 1H), 1.47 (s, 6H). | UPLCMS: Rt$_{H4}$ = 0.79 [M + 1] = 419.3 |

Example 11

5-Cyano-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide

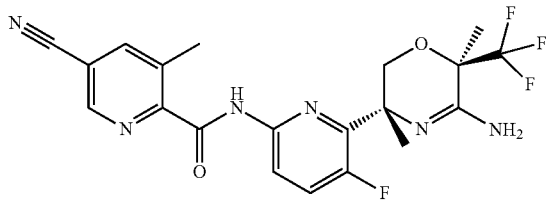 [SMILES: Cc1cc(C#N)cnc1C(=O)Nc1ccc(F)c([C@]2(C)CO[C@@](C)(C(F)(F)F)C(N)=N2)n1]

a) 2-(6-Bromo-3-fluoro-pyridin-2-yl)-propan-2-ol

To a solution of 2-bromo-5-fluoropyridine (25 g, 142 mmol) in diethylether (600 ml) was slowly added n-butyl-lithium (2.5 M in hexane, 56.8 ml, 142 mmol) at −78° C. under a nitrogen atmosphere. The resulting yellow reaction mixture was stirred at −78° C. for 2 hours and dry acetone (11.47 ml, 156 mmol) was added over 30 minutes. Stirring was continued at −78° C. for 1 hour. HCl (2N, 50 ml) was added and the reaction mixture was warmed to 0° C. The pH of the mixture was adjusted to ~7 with 2N HCl solution. The reaction mixture was diluted with ethyl acetate and washed with brine, dried over sodium sulfate, filtered and concentrated in vacuo. The crude product (29.36 g) was chromatographed over silica gel (cyclohexane:ethyl acetate 9:1): 22.3 g (67.1% yield). TLC (cyclohexane/ethyl acetate 9:1) R$_f$=0.33; LCMS Rt$_{H5}$=0.89 min (ES+ 234, 236). ¹H-NMR (360 MHz, DMSO-d₆): 7.72-7.62 (m, 2H), 5.27 (s, 1H, OH), 1.50 (s, 6H, 2×CH₃).

b) 6-Bromo-3-fluoro-2-isopropenyl-pyridine

To a solution of 2-(6-bromo-3-fluoro-pyridin-2-yl)-propan-2-ol (22.3 g, 95 mmol) and methanesulfonic acid anhydride (49.8 g, 286 mmol) in dichloromethane (53.1 ml, 381 mmol) at 0° C. The reaction mixture was stirred at room temperature for 20 hours. The reaction mixture was quenched with aq. sodium carbonate solution and diluted with dichloromethane. The aqueous phase was extracted with dichloromethane. The combined organic layers were washed with brine, dried over sodium sulfate, filtered and evaporated in vacuo (volatile). The crude brown oil was chromatographed over silica (cyclohexane:ethyl acetate 9:1) to give the title compound as a clear liquid. 17.35 g (84% yield). TLC (cyclohexane/ethyl acetate 9:1) R$_f$=0.58; ¹H-NMR (360 MHz, CDCl₃): 7.26-7.15 (m, 2H), 5.72 (s, 1H), 5.47 (s, 1H), 2.12 (s, 3H, CH₃).

c) 2-(6-Bromo-3-fluoro-pyridin-2-yl)-propane-1,2-diol

To a solution of 6-bromo-3-fluoro-2-isopropenyl-pyridine (17.35 g, 80 mmol) in acetone (45 ml) and water (90 ml) was added N-methylmorpholine-N-oxide hydrate (11.4 g, 84 mmol) and osmium tetroxide (5.04 ml, 0.402 mmol). The resulting reaction mixture was stirred at room temperature for 44 hours. Sodium dithionite (2 g) in water (70 ml) was added and the reaction mixture was stirred for 15 minutes and was then filtered and concentrated in vacuo. Ethyl acetate was added and the organic layer was washed with brine, dried over sodium sulfate, filtered and evaporated. 18.29 g slightly yellow solid (91% yield). LCMS Rt$_{H5}$=0.64 min (ES+ 250, 252); ¹H-NMR (360 MHz, CDCl₃): 7.46 (dd, 1H), 7.35 (dd, 1H), 5.09 (s, 1H, OH), 3.96 (d, 1H), 3.78 (d, 1H), 2.45 (broad, 1H, OH), 1.53 (s, 3H, CH₃).

d) Methanesulfonic acid 2-(6-bromo-3-fluoro-pyridin-2-yl)-2-hydroxy-propyl ester To a solution of 2-(6-bromo-3-fluoro-pyridin-2-yl)-propane-1,2-diol (18.29 g, 73.1 mmol) in dichloromethane (350 ml) was added triethylamine (20.39 ml, 146 mmol). Methanesulfonyl chloride (6.27 ml, 80 mmol) was added dropwise at 0° C. over 10 minutes. Stirring was continued at 0° C. for 30 minutes. The reaction mixture was washed with sat. sodium bicarbonate solution, water and brine. The organic layer was dried over sodium sulfate, filtered and evaporated. 31.46 g (crude, used without further purification in the next step). LCMS Rt$_{H5}$=0.81 min. (ES+ 328, 330); ¹H-NMR (360 MHz, CDCl₃): 7.52 (dd, 1H), 7.41 (dd, 1H), 5.13 (s, 1H, OH), 4.61 (d, 1H), 4.45 (d, 1H), 3.05 (s, 3H, CH₃SO₂), 1.61 (s, 3H, CH₃).

e) 1-Azido-2-(6-bromo-3-fluoro-pyridin-2-yl)-propan-2-ol

A mixture of methanesulfonic acid 2-(6-bromo-3-fluoro-pyridin-2-yl)-2-hydroxy-propyl ester (5 g, 15.24 mmol), ammonium chloride (4.08 g, 76 mmol) and sodium azide (2.476 g, 38.1 mmol) in ethanol (100 ml) was stirred at 80° C. for 20 hours. The reaction mixture was diluted with ethyl acetate and washed with water and brine. The organic layer was dried over sodium sulfate, filtered and evaporated. 3.1 g (74% yield). TLC (cyclohexane/ethyl acetate 9:1) $R_f$=0.35; LCMS $Rt_{H5}$=0.97 min. (ES+ 275, 277); $^1$H-NMR (360 MHz, CDCl$_3$): 7.51 (dd, 1H), 7.36 (dd, 1H), 5.18 (s broad, 1H, OH), 3.68-3.60 (AB system, 2H), 1.59 (s, 3H, CH$_3$).

f) 6-Bromo-3-fluoro-2-(2-methyl-aziridin-2-yl)-pyridine

To a solution of 1-azido-2-(6-bromo-3-fluoro-pyridin-2-yl)-propan-2-ol (11.2 g, 40.7 mmol) in THF (60 ml) was added triphenylphosphine (10.68 g, 40.7 mmol) and the reaction mixture was stirred for 18 hours at room temperature. The solvent was removed in vacuo and the residue obtained was dissolved in diethylether and filtered through a cotton plug to remove triphenylphosphine oxide. The filtrate was washed with citric acid (9.6 g in 20 ml of water) and the organic phase was separated. The aqueous layer was made basic with 2N NaOH and extracted with diethylether. The organic layer was dried over sodium sulfate, filtered and evaporated to yield the title compound with some TPPO present: 8.1 g yellow oil (69% yield). TLC (cyclohexane/ethyl acetate 2:1) $R_f$=0.28; LCMS $Rt_{H6}$=0.46 (ES+ 231, 233); $^1$H-NMR (400 MHz, CDCl$_3$): 7.34 (dd, 1H), 7.24 (dd, 1H), 1.99 (s, 1H), 1.89 (s, 1H), 1.65 (s, 3H, CH$_3$).

g) 6-Bromo-3-fluoro-2-[2-methyl-1-(2-nitro-benzenesulfonyl)-aziridin-2-yl]-pyridine To a solution of 6-bromo-3-fluoro-2-(2-methyl-aziridin-2-yl)-pyridine (8 g, 27.7 mmol) in THF (48 ml) and water (16 ml) was added N-methylmorpholine (3.5 ml, 27.7 mmol) and o-nosylchloride. The reaction mixture was stirred for 4 hours at room temperature. 3 g neutral Alox was added and the reaction mixture was filtered. The filtrate was diluted with dichloromethane, washed with sat. sodium hydrogencarbonate solution and water. The organic phase was dried over sodium sulfate, filtered and evaporated. 11.2 g of the crude product was purified over silica gel (cyclohexane:ethyl acetate 60:40) to afford the title compound. 8.69 g (75% yield). LCMS $Rt_{H5}$=1.09 min. (ES+ 416, 418). $^1$H-NMR (400 MHz, CDCl$_3$): 8.27 (m, 1H), 7.80-7.73 (m, 3H), 7.46 (dd, 1H), 7.34 (dd, 1H), 3.32 (s, 1H), 3.20 (s, 1H), 2.10 (s, 3H, CH$_3$).

h) (R)-2-[2-(6-Bromo-3-fluoro-pyridin-2-yl)-2-(2-nitro-benzenesulfonylamino)-propoxy]3,3,3-trifluoro-2-methyl-propionic acid ethyl ester To a solution of (R)-3,3,3-trifluoro-2-hydroxy-2-methyl-propionic acid ethyl ester (715 mg, 3.84 mmol) in DMF (4 ml) was added NaH (55%) (154 mg, 3.84 mmol) at room temperature and the reaction mixture was stirred for 30 minutes at room temperature. A solution of 6-bromo-3-fluoro-2-[2-methyl-1-(2-nitro-benzenesulfonyl)-aziridin-2-yl]-pyridine (800 mg, 1.922 mmol) in DMF (9 ml) was added and the reaction mixture was stirred at room temperature for 48 hours. The reaction mixture was poured onto a mixture of ice/2N HCl/t-butyl-methylether. The organic layer was washed with sat. sodium bicarbonate solution and brine, dried over sodium sulfate, filtered and evaporated. Silica gel chromatography (cyclohexane/ethyl acetate) afforded the title compound as a mixture of 2 diastereoisomers. 300 mg (26% yield). TLC (cyclohexane/ethyl acetate 2:1) $R_f$=0.42; LCMS $Rt_{H5}$=1.25 min (100%, TIC ES+ 602, 604).

i) (R)-2-[2-(6-Bromo-3-fluoro-pyridin-2-yl)-2-(2-nitro-benzenesulfonylamino)-propoxy]-3,3,3-trifluoro-2-methyl-propionamide A solution of (R)-2-[2-(6-bromo-3-fluoro-pyridin-2-yl)-2-(2-nitro-benzenesulfonylamino)-propoxy]3,3,3-trifluoro-2-methyl-propionic acid ethyl ester (720 mg, 1.195 mmol) in NH3 7N in methanol (19 ml, 133 mmol) was stirred at 50° C. for 2 days in a sealed 25 ml microwave vial. The solvent was removed in vacuo and the residue (987 mg) was chromatographed over silica gel (cyclohexane/ethyl acetate) affording the title compound as a mixture of two diastereoisomers (500 mg, 73% yield). TLC (cyclohexane/ethyl acetate 1:1) $R_f$=0.30; LC-MS $Rt_{H5}$=1.05 min (ES+ 573, 575).

j) N-[1-(6-Bromo-3-fluoro-pyridin-2-yl)-2-((R)-1-cyano-2,2,2-trifluoro-1-methyl-ethoxy)-1-methyl-ethyl]-2-nitro-benzenesulfonamide To a solution of (R)-2-[2-(6-bromo-3-fluoro-pyridin-2-yl)-2-(2-nitro-benzenesulfonylamino)-propoxy]-3,3,3-trifluoro-2-methyl-propionamide (200 mg, 0.349 mmol) and triethylamine (0.121 ml, 0.872 mmol) in dichloromethane (3 ml) was added TFAA (0.059 ml, 0.419 mmol) at 0-5° C. and the reaction mixture was stirred for 18 hours at room temperature. Further addition of TFFA and triethylamine (0.6 and 1.2 aequivalent, respectively) brought the reaction to completion after 24 hours. The reaction mixture was added to a cold sat. sodium bicarbonate solution and the product was extracted with dichloromethane. The organic layer was washed with cold 0.1 N HCl solution, water and sat. sodium bicarbonate solution, dried over sodium sulfate, filtered and evaporated in vacuo. 190 mg (98% yield) crude product as a mixture of 2 diastereoisomers. TLC (cyclohexane/ethyl acetate 3:1) $R_f$=0.24; LCMS $Rt_{H5}$=1.20 min (ESI+555, 557).

k) (2R,5S)-5-(6-Bromo-3-fluoro-pyridin-2-yl)-2,5-dimethyl-2-trifluoromethyl-5,6-dihydro-2H-[1,4]oxazin-3-ylamine and (2R,5R)-5-(6-Bromo-3-fluoro-pyridin-2-yl)-2,5-dimethyl-2-trifluoromethyl-5,6-dihydro-2H-[1,4]oxazin-3-ylamine A solution of N-[1-(6-bromo-3-fluoro-pyridin-2-yl)-2-((R)-1-cyano-2,2,2-trifluoro-1-methyl-ethoxy)-1-methyl-ethyl]-2-nitro-benzenesulfonamide (1000 mg, 1.801 mmol), potassium carbonate (548 mg, 3.96 mmol) and N-acetylcysteine (588 mg, 3.6 mmol) in ethanol (17 ml) was stirred at 80° C. for 3 days until all starting material was consumed. The reaction mixture was concentrated in vacuo and the yellow foam redissolved in ethyl acetate and 20% aqueous potassium carbonate solution. The organic phase was washed with sat. sodium bicarbonate solution and brine, dried over magnesium sulfate, filtered and evaporated. 660 mg yellow oil. The 2 diastereoisomers were separated via normal phase preparative HPLC chromatography (cychlohexane/ethyl acete/MeOH).

(2R,5S)-5-(6-Bromo-3-fluoro-pyridin-2-yl)-2,5-dimethyl-2-trifluoromethyl-5,6-dihydro-2H-[1,4]oxazin-3-ylamine (cis derivative)

76 mg. TLC (toluene/ethyl acetate 8:2+5% ETA) $R_f$=0.26; LCMS $Rt_{H4}$=0.73 min (100% purity, EI+ 370, 372); $^1$H-NMR (600 MHz, DMSO-D$_6$): 7.69-7.61 (m, 2H), 6.0 (broad s, 2H, NH₂, amidine), 4.15 (d, 1H, AB-system), 3.71 (s, 1H, AB-system), 1.59 (s, 3H, CH₃), 1.47 (s, 3H, CH₃).

(2R,5R)-5-(6-Bromo-3-fluoro-pyridin-2-yl)-2,5-dimethyl-2-trifluoromethyl-5,6-dihydro-2H-[1,4]oxazin-3-ylamine (trans derivative)

89 mg. TLC (toluene/ethyl acetate 8:2+5% ETA) $R_f$=0.31; LCMS $Rt_{H4}$=0.73 min (100% purity, EI+ 370, 372); ¹H-NMR (600 MHz, DMSO-D₆): 7.73-7.61 (m, 2H), 6.0 (broad s, 2H, NH2, amidine), 4.04 (d, 1H, AB-system), 3.72 (d, 1H, AB-system), 1.52 (s, 3H, CH₃), 1.48 (s, 3H, CH₃).

l) 5-Cyano-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide A mixture of (2R,5R)-5-(6-bromo-3-fluoro-pyridin-2-yl)-2,5-dimethyl-2-trifluoromethyl-5,6-dihydro-2H-[1,4]oxazin-3-ylamine (80 mg, 0.216 mmol), 5-cyano-3-methyl-pyridine-2-carboxylic acid amide (34.8 mg, 0.216 mmol, see Intermediates Amide 1), xantphos (11.26 mg, 0.019 mmol) and cesium carbonate (99 mg, 0.303 mmol) in dioxane (2 ml) was degassed for 5 minutes with argon. Pd₂(dba)₃ (5.94 mg, 6.48 µmol) was added, the microwave vial was sealed and stirred at 80° C. for 18 hours. The reaction mixture was diluted with water and TBME. The organic phase was washed with brine, dried over sodium sulfate, filtered and evaporated. 173 mg orange solid. Silica gel chromatography (applied on two 20×20 cm plate, 1 mm, dichloromethane:methanol 9:1, rechromatographed with dichloromethane:methanol 95:5 with double evolution of the plates) afforded the title compound: 15 mg and 21 mg. Combined amount: 36 mg (37% yield). TLC (dichloromethane/methanol 9:1) $R_f$=0.53; API ES+ MS 451. LCMS $Rt_{H4}$=0.87 min. (100%, ES+ 451), ¹H-NMR (400 MHz, CDCl₃): 10.80 (br s, 1H), 8.83 (br s, 1H), 8.41 (dd, 1H), 7.93 (br s, 1H), 7.55 (t, 1H), 5.8-4.6 (very broad, 2H), 4.23 (br s, 2H), 2.83 (s, 3H), 1.75 (s, 3H), 1.66 (s, 3H).

Example 12

5-Cyano-3-methyl-pyridine-2-carboxylic acid [6-((3S,6R)-5-amino-3,6-dimethyl-6-trifluoromethyl-3,6-dihydro-2H-[1,4]oxazin-3-yl)-5-fluoro-pyridin-2-yl]-amide

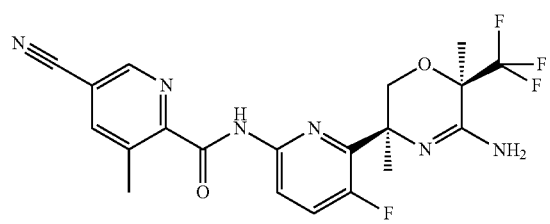 [SMILES: Cc1cc(C#N)cnc1C(=O)Nc1ccc(F)c([C@@]2(C)CO[C@@](C)(C(F)(F)F)C(N)=N2)n1]

5-Cyano-3-methyl-pyridine-2-carboxylic acid [6-((3S,6R)-5-amino-3,6-dimethyl-6-trifluoromethyl-3,6-dihydro-2H-[1,4]oxazin-3-yl)-5-fluoro-pyridin-2-yl]-amide can be prepared by a procedure analogous to that used in Example 11.

TLC (dichloromethane/methanol 9:1) $R_f$=0.47; API ES+ MS 451. LCMS $Rt_{H4}$=0.86 min. (100%, ES+ 451); ¹H-NMR (400 MHz, CDCl₃): 10.65 (br s, 1H), 8.83 (d, 1H), 8.37 (dd, 1H), 7.96 (d, 1H), 7.51 (dd, 1H), 6.0-5.0 (very broad, 2H), 4.38 (d, 1H), 4.09 (d, 1H), 2.85 (s, 3H), 1.78 (s, 3H), 1.71 (s, 3H).

Example 13

5-{2-[(5-Chloro-4,6-dideutero-3-trideuteromethyl-pyridine-2-carbonyl)-amino]-pyridin-4-yl}-5-fluoromethyl-5,6-dihydro-2H-[1,4]oxazin-3-yl-ammonium acetate

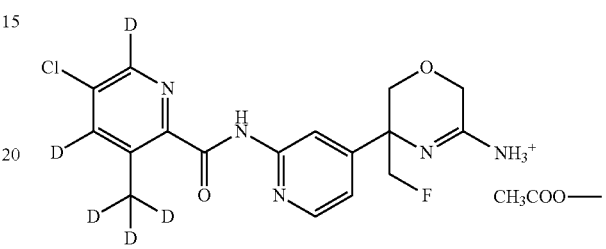

a) 2-(2-Bromo-pyridin-4-yl)-malonic acid diethyl ester

2-Bromo-4-methylpyridine (70.0 g, 407 mmol) was added drop wise to a cooled (−78° C.) solution of LDA (2.0 M in toluene/THF/ethyl benzene, 610.4 ml, 1.22 mol) in dry THF (600 ml) for 30 min. ethylchloroformate (132.3 g, 1.22 mol) was added to the resultant reaction mixture with addition funnel at −78° C. and stirring continued for 90 min. Reaction mixture was treated with saturated NH₄Cl solution and worked up with ethyl acetate by washing with water, brine followed by drying over anhy. Na₂SO₄. Organic layer ws concentrated under reduced pressure to obtain crude product which was purified by column chromatography with 10% ethyl acetate in Hexane to furnish title compound as a brown color oily liquid. Yield: 115.0 g (89%). TLC (10% ethyl acetate in hexane) $R_f$=0.15; LCMS: $Rt_{H8}$=1.475 [M+1]⁺= 315.8 and 317.8; HPLC $Rt_{H9}$=7.30 min (86.7%); ¹H NMR (400 MHz, CDCl₃) δ 8.38 (d, 1H), 7.56 (t, 1H), 7.34 (dd, 1H), 4.55 (s, 1H), 4.29-4.18 (m, 4H), 1.28 (t, 6H).

b) (2-Bromo-pyridin-4-yl)-acetic acid

A suspension of 2-(2-bromo-pyridin-4-yl)-malonic acid diethyl ester (115 g, 316 mmol) and K₂CO₃ (125.23 g, 907.5 mmol) in water (500 ml) was heated at 100° C. for 8 h under constant stirring. Reaction mixture was cooled to rt and concentrated under reduced pressure to remove solvent completely. The solid residue was dissolved in minimum quantity of water (25 ml) and washed with 20% ethyl acetate in hexane to remove non polar impurities. The aqueous layer was separated and cooled to 0° C. followed by adjusting pH 6 to 7 using aq. 6 N HCl. The precipitated solid was filtered using Buchner funnel, washed with ice cold water and dried under vacuum to furnish title compound as an off white solid. with sufficient purity. Yield: 60.0 g (76.3%). TLC (70% ethyl acetate in hexane) $R_f$=0.05; LCMS: $Rt_{H8}$=0.193; [M+1]⁺ = 215.9 and 217.9; HPLC $Rt_{H9}$=3.025 min (98%); ¹H NMR (400 MHz, CDCl₃): δ 12.71 (s, 1H), 8.33 (d, 1H), 7.61 (s, 1H), 7.37 (d, 1H), 3.71 (s, 3H).

c) (2-Bromo-pyridin-4-yl)-acetic acid ethyl ester

To a solution of (2-bromo-pyridin-4-yl)-acetic acid (60.0 g, 277.7 mmol) in ethanol (600 ml), conc: sulfuric acid (5.0 ml) was added at rt and the reaction mixture was heated at 90° C. for 9 h. Reaction mixture was cooled to rt and concentrated under reduced pressure to remove solvent completely. The residue obtained was cooled to 0° C. and pH was adjusted to 8 using 10% aqueous NaHCO$_3$ solution. The resultant contents were worked up with ethyl acetate by washing with water, brine and dried over anhy. Na$_2$SO$_4$. Organic layer was concentrated under reduced pressure to obtain crude compound. Column chromtography purification of the crude compound using 15% ethyl acetate in hexane as eluent furnished title compound as a brown oil. Yield: 65.0 g (88.5%). TLC (30% ethyl acetate in hexane) R$_f$=0.39; LCMS: Rt$_{H7}$=0.824 [M+1]$^+$=243.8 and 245.8; HPLC Rt$_{H9}$=3.759 min (69%); $^1$H NMR (300 MHz, CDCl$_3$): δ 8.32 (t, 1H), 7.43 (s, 1H), 7.21-7.15 (M, 1H), 4.18 (q, 2H), 1.27 (t, 3H).

d) 2-(2-Bromo-pyridin-4-yl)-3-hydroxy-2-hydroxymethyl-propionic acid ethyl ester To an ice cooled stirred mixture of (2-bromo-pyridin-4-yl)-acetic acid ethyl ester (40.0 g, 163.93 mmol) and paraformaldehyde (9.84 g, 327.8 mmol) in dry DCM was added 1,8-diazabicyclo[5.4.0]undec-7-ene (1.49 g, 1.49 ml, 9.83 mmol) and stirred for 2 h. Reaction mixture was treated with (1R)-(−)-10-camphor sulphonic acid (2.283 g, 9.83 mmol) at 0° C. and the organic layer was washed with brine and dried over anhydrous Na$_2$SO$_4$. Concentration of organic layer afforded gummy oily material. The crude compound was purified over triethyl amine treated silicagel using 5-8% methanol in DCM as eluent furnished title compound as a brown liquid. Yield=20.0 g (40%). TLC (30% ethyl acetate in hexane) R$_f$=0.06; LCMS: Rt$_{H7}$=0.191; [M+1]$^+$=303.9 and 305.8; HPLC Rt$_{H9}$=6.019 min (43%); $^1$H NMR (400 MHz, CDCl$_3$): δ 8.36-8.31 (m, 1H), 7.34-7.25 (m, 1H), 6.37-6.33 (m, 1H), 4.6 (d, 1H), 4.14-4.08 (m, 2H), 4.04-3.91 (m, 4H), 1.13 (t, 3H).

e) 5-(2-Bromo-pyridin-4-yl)-2,2-dimethyl-[1,3]dioxane-5-carboxylic acid ethyl ester A mixture of 2-(2-bromo-pyridin-4-yl)-3-hydroxy-2-hydroxymethyl-propionic acid ethyl ester (30.0 g, 98.6 mmol) 2,2-dimethoxy propane (51.11 g, [60.5 ml], 493.1 mmol) and (1R)-(−)-10-camphor sulphonic acid (5.72 g, 24.65 mmol) in DMF (100 ml) was heated at 80° C. for 10 h. Reaction mixture was cooled to rt and concentrated under reduced pressure. The residue was dissolved in ethyl acetate and worked up by washing with water, brine, followed by drying over anhy. Na$_2$SO$_4$. Organic layer was concentrated under reduced pressure and the crude product was purified by column chromatography using 10% ethyl acetate in Hexane to obtain title compound as a yellow solid. Yield=18.15 g (53%). TLC (30% ethyl acetate in hexane) R$_f$=0.52; LCMS: Rt$_{H7}$=1.487; [M+1]$^+$=344.0 and 346.0; HPLC Rt$_{H9}$=7.6 min (74%); $^1$H NMR (300 MHz, CDCl$_3$): δ 8.41-8.34 (t, 1H), 7.54 (s, 1H), 7.32-7.28 (m, 1H), 4.51 (dd, 2H), 4.27-4.21 (q, 4H), 1.45 (s, 3H), 1.39 (s, 3H), 1.23 (t, 3H).

f) 5-(2-Bromo-pyridin-4-yl)-2,2-dimethyl-[1,3]dioxane-5-carboxylic acid ethyl ester A solution of LiOH.H$_2$O (11.1 g, 263.5 mmol) in water (10 ml) was added to a solution of 5-(2-bromo-pyridin-4-yl)-2,2-dimethyl-[1,3]dioxane-5-carboxylic acid ethyl ester (18.1 g, 52.7 mmol) in ethanol (60 ml) at 0° C. and the resultant reaction mixture was stirred at rt for 3 h. Reaction mixture was concentrated under reduced pressure to remove solvent completely. The wet mass obtained was cooled to 0° C., acidified with glacial acetic acid (to maintain pH ~6) and the product was extracted with ethyl acetate (2×100 ml). Organic layer was washed with brine and concentrated to afford brown solid which was used in the next step without further purification. Yield=14.1 g (85%). TLC (50% ethyl acetate in hexane) R$_f$=0.03; LCMS: Rt$_{H8}$=0.343 [M+1]$^+$=316.0, 318.0; $^1$H NMR (300 MHz, CDCl$_3$): δ 8.28-8.21 (t, 1H), 7.7 (s, 1H), 7.58-7.54 (m, 1H), 4.21-3.95 (dd, 4H), 1.36 (s, 3H), 1.14 (s, 3H).

g) 5-(2-Bromo-pyridin-4-yl)-2,2-dimethyl-[1,3]dioxan-5-ylamine

Dipheny phosphoryl azide (14.3 mL, 66.45 mmol) was added to a solution of 5-(2-bromo-pyridin-4-yl)-2,2-dimethyl-[1,3]dioxane-5-carboxylic acid ethyl ester (14.0 g, 44.3 mmol) and triethyl amine (17.24 ml, 133.0 mmol) in toluene (100 ml) at 0° C. The resultant reaction mixture was heated to 80° C. under constant stirring for 7 h. Reaction mixture was concentrated under reduced pressure to remove solvent completely. The residue obtained after concentration was dissolved in THF (100 ml) and cooled to 0° C. 2 N aq. NaOH solution was added drop wise and stirred for 30 min at rt. Reaction mixture was concentrated under reduced pressure to remove THF and the residue obtained was extracted with ethylacetate. Organic layer was washed with water, brine and dried over anhy. Na$_2$SO$_4$. Organic layer was concentrated under reduced pressure to obtain brownish oily material which was solidified at low temperature (<10° C.). Yield=9.5 g (75%). TLC (50% ethyl acetate in hexane) R$_f$=0.15; LCMS: Rt$_{H7}$=0.083; [M+1]$^+$=287.0 and 289.0.

h) N-[5-(2-Bromo-pyridin-4-yl)-2,2-dimethyl-[1,3]dioxan-5-yl]-2-chloro-acetamide To a solution of 5-(2-bromo-pyridin-4-yl)-2,2-dimethyl-[1,3]dioxan-5-ylamine (9.5 g, 33.1 mmol) in DCM (100 ml) was added aq. Na$_2$CO$_3$ (8.7 g in 50 ml) at 0° C. and stirring continued for 5 min. Chloroacetyl chloride (2.9 ml, 36.41 mmol) was added to the resultant reaction mixture drop wise and stirred for 30 min at 0° C. Reaction mass was diluted with DCM (200 ml) and organic layer was washed successively washed with water, brine, dried over anhydrous Na$_2$SO$_4$ and concentrated under reduced pressure to obtain brown solid. The product was directly used in the next step with further purification. Yield=10.2 g (85%). TLC (50% ethyl acetate in hexane) R$_f$=0.15; LCMS: Rt$_{H8}$=0.55 [M+1]$^+$=363.0 and 364.9.

i) N-[1-(2-Bromo-pyridin-4-yl)-2-hydroxy-1-hydroxymethyl-ethyl]-2-chloro-acetamide A solution of N-[5-(2-bromo-pyridin-4-yl)-2,2-dimethyl-[1,3]dioxan-5-yl]-2-chloro-acetamide (10.0 g, 27.6 mmol) in DCM (150 ml) was cooled to 0° C. for 10 min. and trifluoromethyl acetic acid (15.0 ml) was added. Stirring continued for 2 h and the resultant contents were concentrated under reduced pressure. The residue formed was basified with aq. NH$_4$OH solution and the product was extracted with ethyl acetate (3×200 ml) by washing organic layer with brine (5.0 ml) and dried over anhy. Na$_2$SO$_4$. Organic layer was concentrated under reduced pressure to obtain title compound as a brown liquid which was carried to next step without any purification. Yield=8.1 g (91%). TLC (70% ethyl acetate in hexane) R$_f$=0.15; LCMS: Rt$_{H8}$=0.12 [M+1]$^+$=322.9 and 324.9; HPLC Rt$_{H9}$=5.266 min (61%), 5.104 (25%).

j) 5-(2-Bromo-pyridin-4-yl)-5-hydroxymethyl-morpholin-3-one

To a solution of N-[1-(2-bromo-pyridin-4-yl)-2-hydroxy-1-hydroxymethyl-ethyl]-2-chloro-acetamide (8.0 g, 24.8 mmol) in t-BuOH (50 ml) was added t-BuOK (5.5 g, 49.6 mmol) and NaI (0.375 g, 2.48 mmol) and heated to 90° C. for 1 h. Reaction mass was concentrated under reduced pressure and diluted the residue with EtOAc. Organic layer was separated and washed with ammonium chloride solution, brine followed by drying over anhy. Na$_2$SO$_4$. The crude product was purified by column chromatography using 5% methanol in DCM to obtain title compound as a pale brown gum. Yield=3.25 g (46%). TLC (ethyl acetate) R$_f$=0.17; LCMS: Rt$_{H8}$=0.12; [M+1]$^+$=286.7 and 289.

k) 5-(2-Bromo-pyridin-4-yl)-5-fluoromethyl-morpholin-3-one

To a suspension of 5-(2-bromo-pyridin-4-yl)-5-hydroxymethyl-morpholin-3-one (3.25 g, 11.0 mmol), Na$_2$CO$_3$ (3.5 g, 13.06 mmol) in dry THF (15 ml) was added diethylaminosulfur trifluoride (2.25 ml, 17.0 mmol) at 0° C. The reaction mixture was allowed to warm to rt and stirred for 2 h. Solid Na$_2$CO$_3$ (3.5 g) was again added to the reaction mixture and stirred for 4 h at rt. Solids present in the reaction mixture filtered through Buchner funnel. Filtrate was concentrated under reduced pressure and the crude product was purified by column chromatography using 5% methanol in DCM to obtain title compound as a pale yellow solid.

Yield=2.1 g (66%). TLC (50% ethyl acetate in hexane) R$_f$=0.17; LCMS: Rt$_{H7}$=0.201; [M+1]$^+$=289 and 291; HPLC: Rt$_{H9}$=5.171 min. (50%) and 5.063 (21%).

l) 5-Chloro-4,6-dideutero-3-trideuteromethyl-pyridine-2-carboxylic acid [4-(3-fluoromethyl-5-oxo-morpholin-3-yl)-pyridin-2-yl]-amide A stirred solution of 5-(2-bromo-pyridin-4-yl)-5-fluoromethyl-morpholin-3-one (0.2 g, 0.695 mmol), 5-chloro-4,6-dideutero-3-trideuteromethyl-pyridine-2-carboxylic acid (Acid 2) (0.135 g, 0.763 mmol) and cesium carbonate (0.678 g, 2.085 mmol) in 1,4-dioxane (5.0 ml) was degassed with argon for 10 min. 4,5-Bis(diphenyl phosphino)-9,9-dimethyl xanthenes (0.041 g, 0.035 mmol) was added to the resultant mixture and degassed again for 10 min. Tris(dibenzylideneacetone) di palladium(0) (0.032 g, 0.07 mmol) was then added finally and degassed with argon for further 5 min. Reaction mixture was heated to 80° C. for 20 h and cooled to rt. Water was added to the reaction mixture and product was extracted with ethyl acetate by washing with brine followed by drying over anhy. Na$_2$SO$_4$. The organic layer was concentrated under reduced pressure to obtain title compound as a sticky solid which was used for the next step without purification. Yield=0.14 g (52%). TLC (50% ethyl acetate in hexane) R$_f$=0.45; LCMS: Rt$_{H8}$=0.868 [M+1]$^+$=384.0; $^1$H NMR (300 MHz, CDCl$_3$): δ 10.7 (s, 1H), 8.51-8.41 (m, H) 7.51-7.46 (d, 1H), 7.34-7.16 (m, 1H), 4.99-4.60 (m, 2H), 4.34-3.79 (m, 4H).

m) 5-Chloro-4,6-dideutero-3-trideuteromethyl-pyridine-2-carboxylic acid [4-(3-fluoromethyl-5-thioxo-morpholin-3-yl)-pyridin-2-yl]-amide Lawesson's reagent (0.46 g, 1.135 mmol) was added to a stirred solution of 5-chloro-4,6-dideutero-3-trideuteromethyl-pyridine-2-carboxylic acid [4-(3-fluoromethyl-5-oxo-morpholin-3-yl)-pyridin-2-yl]-amide (0.14 g, 0.378 mmol) in THF (4.0 ml) and heated to reflux for 2 h. The reaction mixture was concentrated under reduced pressure to obtain crude product as a sticky solid which was purified by column chromatography using 25% ethyl acetate in hexane as eluent to obtain title compound as a sticky solid. Yield=0.095 g (65%). TLC (30% ethyl acetate in hexane) R$_f$=0.61; LCMS: Rt$_{H8}$=1.489 [M+1]$^+$=399.8.

n) 5-{2-[(5-Chloro-4,6-dideutero-3-trideuteromethyl-pyridine-2-carbonyl)-amino]-pyridin-4-yl}-5-fluoromethyl-5,6-dihydro-2H-[1,4]oxazin-3-yl-ammonium acetate A solution of 5-chloro-4,6-dideutero-3-trideuteromethyl-pyridine-2-carboxylic acid [4-(3-fluoromethyl-5-thioxo-morpholin-3-yl)-pyridin-2-yl]-amide (0.095 g, 0.238 mmol) in 10% methanolic ammonia (5.0 ml) was stirred in a sealed tube for 16 h at rt. Reaction mixture was concentrated under reduced pressure to obtain semi-solid. Product was purified by preparative HPLC method to obtain title compound as a semi solid. Conditions for preparative HPLC: Column: Agilent Zorbax XDB C18. Mobile phase: A: 10 mm; ammonium acetate; B: ACN, 60 ml; Flow: 20 ml/min.; Gradient: 0-30, 2-40, 10-80. Yield=28 mg (31%). LCMS: Rt$_{H7}$=0.191 [M+1]$^+$=383.1; HPLC: Rt$_{H9}$ 3.208 min (97%); $^1$H NMR (300 MHz, DMSO-d$_6$): δ 10.52 (s, 1H), 8.35 (dd, 2H), 7.28 (d, 1H), 6.15 (br. s, 1H), 4.51-4.28 (m, 2H), 4.07-3.94 (m, 3H)), 3.69 (d, 2H), 1.89 (s, 3H); $^{19}$F NMR (376.1): δ−218.9.

Examples 14 and 15

The compounds listed in Table 6 were prepared by a procedure analogous to those used in Example 13.

TABLE 6

| Example | Compound | $^1$H-NMR (δ; DMSO-d$_6$) | MS [m/z; (M + 1)$^+$] |
|---|---|---|---|
| 14 | (structure) | 10.3 (br. s, 1H), 8.83 (d, 1H, J = 2.0 Hz), 8.45 (s, 1H), 8.33 (d, 1H, J = 5.2 Hz), 8.26-8.18 (m, 2H), 7.31 (d, 1H, J = 5.6 Hz), 6.07 (brs, 2H), 4.51-4.28 (m, 2H), 4.06-3.93 (m, 4H), 3.7-3.67 (m, 2H). | LCMS: Rt$_{H7}$ = 0.112 [M + 1]$^+$ = 363.9 |

5-{2-[(5-Chloro-pyridine-2-carbonyl)-amino]-pyridin-4-yl}-5-fluoromethyl-5,6-dihydro-2H-[1,4]oxazin-3-yl-ammonium trifluoro-acetate

TABLE 6-continued

| Example | Compound | $^1$H-NMR (δ; DMSO-$d_6$) | MS [m/z; (M + 1)$^+$] |
|---|---|---|---|
| 15 | 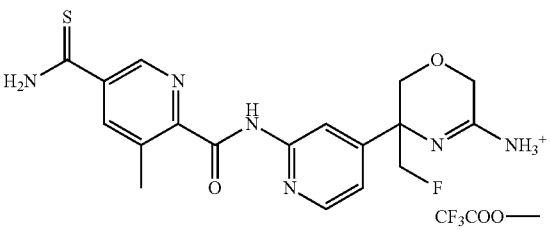<br>5-Fluoromethyl-5-{2-[(3-methyl-5-thiocarbamoyl-pyridine-2-carbonyl)-amino]-pyridin-4-yl}-5,6-dihydro-2H-[1,4]oxazin-3-yl-ammonium trifluoro-acetate | 8.96 (d, 1H), 8.51 (s, 2H), 8.45 (d, 2H), 8.19 (s, 1H), 7.32 (d, 2H), 5.11-4.99 (m, 2H), 4.72 (s, 3H), 4.27-4.19 (m, 2H), 4.16-4.08 (m, 2H). | LCMS: Rt$_{H7}$ = 0.118; [M + 1]$^+$ = 403.1 |

Example 16

5-Cyano-3-methyl-pyridine-2-carboxylic acid [4-((3R,6R)-5-amino-3,6-dimethyl-6-trifluoromethyl-3,6-dihydro-2H-[1,4]oxazin-3-yl)-5-fluoro-pyridin-2-yl]-amide

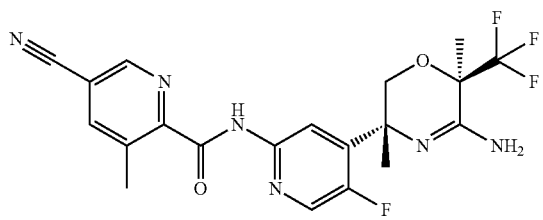 [SMILES: Cc1cc(C#N)cnc1C(=O)Nc1cc([C@]2(C)CO[C@@](C)(C(F)(F)F)C(N)=N2)c(F)cn1]

a) 2-(2-Bromo-5-fluoro-pyridin-4-yl)-propan-2-ol

To a solution of 2-bromo-5-fluoro-pyridine (CAS 41404-58-4, 25.0 g, 139 mmol) in THF (300 ml) was added dropwise LDA (100 ml of a 2M soln. in THF/heptane/ethylbenzene, 200 mmol) at −78° C. under a $N_2$ atmosphere. Stirring was continued for 1 h at −78° C., then acetone (20.44 ml, 16.17 g, 278 mmol) was added dropwise and stirring was continued at −78° C. for another 1 h. The reaction mixture was quenched with aq. 1M NH$_4$Cl soln. and diluted with EtOAc. The phases were separated and the aq. phase was twice reextracted with EtOAc. The combined org. phases were washed with brine, dried over Na$_2$SO$_4$, filtered, concentrated. Flash chromatography on silica gel (gradient cyclohexane:EtOAc 100:0 to 90:10) followed by crystallization from pentane yielded the title compound as a colourless solid. HPLC Rt$_{H4}$=0.81 min; ESIMS: 234, 236 [(M+H)$^+$]; $^1$H NMR (400 MHz, DMSO-$d_6$): δ 8.32 (br s, 1H), 7.71 (d, 1H), 5.57 (s, 1H), 4.90 (t, 1H), 3.65-3.57 (m, 1H), 3.53-3.44 (m, 1H), 1.39 (s, 3H).

b) 2-Bromo-5-fluoro-4-isopropenyl-pyridine

To a solution of 2-(2-bromo-5-fluoro-pyridin-4-yl)-propan-2-ol (24.7 g, 106 mmol) and methanesulfonic anhydride (55.1 g, 317 mmol) in DCM (250 ml) was added triethylamine (58.8 ml, 42.7 g, 422 mmol). The reaction mixture was stirred at rt for 20 h. Another 1 eq. (18 g) of methanesulfonic anhydride and 1.2 eq. (17 ml) of triethylamine were added and the reaction mixture was stirred an additional 20 h at rt. The reaction mixture was quenched with 1M aq. Na$_2$CO$_3$ sol. and diluted with DCM. The phases were separated and the aq. phase was reextracted twice with DCM. The combined org. phases were washed with brine, dried over Na$_2$SO$_4$, filtered and concentrated. Flash chromatography on silica gel (hexane:EtOAc 8:1) yielded the title compound as a clear colourless liquid. HPLC Rt$_{H4}$=1.12 min; ESIMS: 216, 218 [(M+H)$^+$]; $^1$H NMR (400 MHz, CDCl$_3$): δ 8.20 (d, 1H), 7.40 (d, 1H), 5.48-5.44 (m, 2H), 2.14 (s, 3H).

c) 2-(2-Bromo-5-fluoro-pyridin-4-yl)-propane-1,2-diol

To a solution of 2-bromo-5-fluoro-4-isopropenyl-pyridine (17.1 g, 79 mmol) in acetone (50 mL) and H$_2$O (100 mL) was added N-methylmorpholine oxide (10.51 g, 87 mmol) and OSO$_4$ (4.97 mL, 4.02 g, 0.396 mmol). The biphasic mixture was stirred at rt for 17 h. The reaction mixture was quenched with sodium hydrosulfite (1.516 g, 8.71 mmol) in H$_2$O (50 ml) and stirred at rt for 20 min. The reaction mixture was filtered through celite and the celite pad was washed three times with acetone. The combined filtrates were evaporated and the residue was taken up with EtOAc and 1N aq. NaOH soln. The phases were separated and the aq. phase was reextracted with EtOAc. The combined org. phases were dried over Na$_2$SO$_4$, filtered and concentrated to yield the title compound as a light purple solid. HPLC Rt$_{H4}$=0.60 min; ESIMS: 250, 252 [(M+H)$^+$]; $^1$H NMR (400 MHz, DMSO-$d_6$): δ 8.32 (d, 1H), 7.71 (d, 1H), 5.57 (s, 1H), 4.89 (t, 1H), 3.65-3.57 (m, 1H), 3.53-3.45 (m, 1H), 1.39 (s, 3H).

d) Methanesulfonic acid 2-(2-bromo-5-fluoro-pyridin-4-yl)-2-hydroxy-propyl ester To a suspension of 2-(2-bromo-5-fluoro-pyridin-4-yl)-propane-1,2-diol (17.45 g, 69.8 mmol) and triethylamine (19.45 ml, 14.12 g, 140 mmol) in DCM (350 ml) at 0° C. was added dropwise methanesulfonyl chloride (5.71 ml, 8.39 g, 73.3 mmol) over a period of 10 min. The reaction mixture was stirred at 0° C. for 30 min, then quenched with 1M aq. NaHCO$_3$ soln. The phases were separated, the aq. phase was twice reextracted with DCM and the combined org. phases were washed with brine, dried over Na$_2$SO$_4$, filtered and concentrated. Flash chromatography on silica gel (gradient heptane: EtOAc 0-5 min 88:12, 5-37.5 min 24:76) yielded the title compound as a clear oil. HPLC Rt$_{H4}$=0.76 min; ESIMS:

328, 330 [(M+H)⁺]; ¹H NMR (400 MHz, DMSO-d₆): δ 8.22 (d, 1H), 7.82 (d, 1H), 4.58-4.47 (m, 2H), 3.04 (s, 3H), 3.00 (s, 1H), 1.64 (s, 3H).

e) 1-Azido-2-(2-bromo-5-fluoro-pyridin-4-yl)-propan-2-ol

To a solution of methanesulfonic acid 2-(2-bromo-5-fluoro-pyridin-4-yl)-2-hydroxy-propyl ester (10.36 g, 31.6 mmol) in ethanol (160 ml) was added NaN₃ (5.13 g, 79.0 mmol) and NH₄Cl (8.44 g, 158.0 mmol). The reaction mixture was stirred at 80° C. for 20 h. The reaction mixture was diluted with H₂O and TBME and the phases were separated. The aq. phase was twice reextracted with TBME, the combined org. phases were washed with brine, dried over Na₂SO₄, filtered and concentrated. HPLC Rt$_{H4}$=0.89 min; ESIMS: 275, 277 [(M+H)⁺]; ¹H NMR (400 MHz, CDCl₃): δ 8.20 (d, 1H), 7.80 (d, 1H), 3.81 (d, 1H), 3.65 (d, 1H), 1.61 (s, 3H).

f) Methanesulfonic acid 2-azido-1-(2-bromo-5-fluoro-pyridin-4-yl)-1-methyl-ethyl ester At 0° C., methanesulfonyl chloride (2.04 ml, 3.00 g, 26.20 mmol) was dropwise added to a solution of 1-azido-2-(2-bromo-5-fluoro-pyridin-4-yl)-propan-2-ol (6.00 g, 21.81 mmol) and NEt₃ (3.65 ml, 2.65 g, 26.2 mmol) in DCM (200 ml). The reaction mixture was stirred at 0° C. for 1 h, then for another 1 h at 0° C. to rt. The reaction mixture was quenched with 1M aq. NaHCO₃ soln. and diluted with DCM. The phases were separated and the aq. phase was twice reextracted with DCM. The combined org. phases were dried over Na₂SO₄, filtered and concentrated. HPLC purification (Alltech Grom Saphir 65 Si 10 μM column, 250×50 mm, gradient n-heptane:EtOAc 0-1.6 min 85:15, 1.6-16 min 0:100, 16-21.2 min 0:100, flow 100 ml/min, detection 254 nm) yielded the title compound as well as recovered starting material that could be reacted again according to the above procedure. HPLC Rt$_{H4}$=0.96 min; ESIMS: 353, 355 [(M+H)⁺]; ¹H NMR (400 MHz, CDCl₃): δ 8.28 (d, 1H), 7.56 (d, 1H), 4.08 (d, 1H), 3.82 (d, 1H), 3.22 (s, 3H), 2.13 (s, 3H).

g) 2-Bromo-5-fluoro-4-[2-methyl-1-(2-nitro-benzenesulfonyl)-aziridin-2-yl]-pyridine A mixture of methanesulfonic acid 2-azido-1-(2-bromo-5-fluoro-pyridin-4-yl)-1-methyl-ethyl ester (2.1 g, 6.09 mmol) and PPh₃ (1.597 g, 6.09 mmol) in THF (20 mL) was stirred at rt for 30 min. The reaction mixture was evaporated to dryness, the residue was taken up with TBME and 10% aq. citric acid soln. The aq. phase was reextracted with TBME, the combined org. phases were washed with H₂O. The combined aq. phases were basified using 2N aq. NaOH soln. and three times extracted with TBME. The combined org. phases were dried over Na₂SO₄, filtered and concentrated to yield 2-bromo-5-fluoro-4-(2-methyl-aziridin-2-yl)-pyridine in a mixture with Ph₃PO that was used for the next step without further purification, HPLC Rt$_{H4}$=0.96 min; ESIMS: 231, 233 [(M+H)⁺].

To a solution of crude 2-bromo-5-fluoro-4-(2-methyl-aziridin-2-yl)-pyridine (3.17 g as a 45% mixture with Ph₃PO, 6.17 mmol) and 2-nitrobenzene-1-sulfonyl chloride (1.368 g, 6.17 mmol) in THF (23.15 mL) and H₂O (7.72 mL) was added N-methylmorpholine and the reaction mixture was stirred at rt for 1.5 h. Alox neutral (2-3 spatula) was added and the reaction mixture was filtered through celite, washed with DCM and the filtrates were diluted with DCM and 1M aq. NaHCO₃ soln. The phases were separated and the aq. phase was reextracted twice with DCM. The combined org. phases were dried over Na₂SO₄ and concentrated. Flash chromatography on silica gel (heptane:EtOAc 4:1 to 3:1) followed by recrystallization from EtOAc/hexane yielded the title compound as a colourless solid. HPLC Rt$_{H4}$=1.11 min; ESIMS: 416, 418 [(M+H)⁺]; ¹H NMR (400 MHz, CDCl₃): δ 8.31-8.30 (m, 1H), 8.23 (d, 1H), 7.86-7.77 (m, 3H), 7.68 (d, 1H), 3.28 (s, 1H), 2.78 (s, 1H), 2.09 (s, 3H).

h) (R)-2-[(RS)-2-(2-Bromo-5-fluoro-pyridin-4-yl)-2-(2-nitro-benzenesulfonylamino)-propoxy]-3,3,3-trifluoro-2-methyl-propionic acid ethyl ester To a solution of 2-bromo-5-fluoro-4-[2-methyl-1-(2-nitro-benzenesulfonyl)-aziridin-2-yl]-pyridine (795 mg, 1.91 mmol) and (R)-3,3,3-trifluoro-2-hydroxy-2-methyl-propionic acid ethyl ester (498 mg, 2.67 mmol) in DMF (8 ml, soln. predried over mol. sieves) was added NaH (99 mg of a 60% dispersion in mineral oil, 2.48 mmol) and the reaction mixture was stirred at rt for 3 h. The reaction mixture was quenched with aq. 1N HCl and diluted with H₂O and TBME. The phases were separated and the aq. phase was twice extracted with TBME. The combined org. phases were washed with H₂O, dried over Na₂SO₄, filtered and concentrated. Flash chromatography on silica gel (heptane:EtOAc 1:1) yielded the title compound (diastereomer mixture) as a colourless solid. HPLC Rt$_{H4}$=1.26 min; ESIMS: 602, 604 [(M+H)⁺]; ¹H NMR (400 MHz, CDCl₃): δ 7.99 (m, 1H), 7.95-7.93 (m, 1H), 7.79-7.61 (m, 4H), 6.94 (m, 1H), 4.45-4.33 (m, 2H), 3.94-3.81 (m, 2H), 1.85 (m, 3H), 1.61 (m, 3H), 1.40-1.34 (m, 3H).

i) (R)-2-[(RS)-2-(2-Bromo-5-fluoro-pyridin-4-yl)-2-(2-nitro-benzenesulfonylamino)-propoxy]-3,3,3-trifluoro-2-methyl-propionamide A solution of (R)-2-[(RS)-2-(2-Bromo-5-fluoro-pyridin-4-yl)-2-(2-nitro-benzenesulfonylamino)-propoxy]-3,3,3-trifluoro-2-methyl-propionic acid ethyl ester (920 mg, 1.527 mmol) in 7N NH₃/MeOH (11 ml) was stirred in a sealed glass vial at 55° C. for 44 h. The reaction mixture was evaporated to dryness to leave a yellow solid that was used for the next step without further purification (diastereomer mixture). Rt$_{H4}$=1.03 min; ESIMS: 573, 575 [(M+H)⁺]; ¹H NMR (400 MHz, CDCl₃): δ 8.00 (m, 1H), 7.97-7.91 (m, 1H), 7.80-7.63 (m, 3H), 7.55 (m, 1H), 6.63 (m, 1H), 6.41 (m, 1H), 5.74 (m, 1H), 4.15 (m, 1H), 3.97 (m, 1H), 1.84 (2s, 3H), 1.69 (2s, 3H).

j) N—[(RS)-1-(2-Bromo-5-fluoro-pyridin-4-yl)-2-((R)-1-cyano-2,2,2-trifluoro-1-methyl-ethoxy)-1-methyl-ethyl]-2-nitro-benzenesulfonamide To a dry solution of (R)-2-[(RS)-2-(2-bromo-5-fluoro-pyridin-4-yl)-2-(2-nitro-benzenesulfonyl-amino)-propoxy]-3,3,3-trifluoro-2-methyl-propionamide (860 mg, 1.35 mmol) in DCM (9 ml) was added at rt NEt₃ (0.470 ml, 342 mg, 3.38 mmol). At 0° C., trifluoroacetic anhydride (0.229 ml, 340 mg, 1.62 ml) was added dropwise. The reaction mixture was allowed to warm to rt and to stir for 1.5 h. The reaction mixture was diluted with 1M aq. Na₂CO₃ soln. and DCM. The phases were separated and the aq. phase was twice reextracted with DCM. The combined org. phases were dried over Na₂SO₄, filtered and concentrated to yield the crude title compound as an orange solid that was used in the next step without further purification (diastereomer mixture). Rt$_{H4}$=1.19 min; ESIMS: 555, 557 [(M+H)⁺]; ¹H NMR (400

MHz, CDCl₃): δ 8.01-7.93 (m, 2H), 7.79-7.63 (m, 3H), 7.59 (m, 1H), 4.26-4.16 (m, 2H), 1.85-1.84 (2d, 3H), 1.78-1.76 (2d, 3H).

k) (2R,5R)- and (2R,5S)-5-(2-Bromo-5-fluoro-pyridin-4-yl)-2,5-dimethyl-2-trifluoro-methyl-5,6-dihydro-2H-[1,4]oxazin-3-ylamine A mixture of N-[1-(2-bromo-5-fluoro-pyridin-4-yl)-2-((R)-1-cyano-2,2,2-trifluoro-1-methyl-ethoxy)-1-methyl-ethyl]-2-nitro-benzenesulfonamide (585 mg, 1.053 mmol), N-acetylcysteine (344 mg, 2.107 mmol) and K₂CO₃ (291 mg, 2.107 mmol) in EtOH (7 ml) was stirred at 85° C. for 68 h under N₂. The reaction mixture was concentrated to ⅓ of its volume and diluted with cold 10% aq. K₂CO₃ soln. and TBME. The phases were separated and the aq. phase was twice reextracted with TBME. The combined org. phases were washed with 1M aq. NaHCO₃ soln. and brine, was dried over Na₂SO₄, filtered and concentrated. HPLC purification (Alltech Grom Saphir 65 Si 10 μM column, 150×30 mm, gradient n-heptane:EtOAc:MeOH 0-1.2 min 68:30:2, 1.2-9 min 0:80:20, 9-12 min 0:65:35, flow: 50 ml/min, detection: 254 nm) separated the (2R,5R)- from the (2R,5S)-diastereomer of the title compound. Rt$_{H4}$=0.70 min; ESIMS: 370, 372 [(M+H)⁺]; ¹H NMR (400 MHz, DMSO-d₆): (2R,5R)-diastereomer δ 8.39 (br s, 1H), 7.81 (d, 1H), 6.28 (br s, 2H), 3.94 (d, 1H), 3.75 (d, 1H), 1.49 (s, 3H), 1.41 (s, 3H);

(2R,5S)-diastereomer δ 8.37 (d, 1H), 7.68 (d, 1H), 6.34 (br s, 2H), 3.91 (d, 1H), 3.83 (d, 1H), 1.59 (s, 3H), 1.40 (s, 3H).

l) 5-Cyano-3-methyl-pyridine-2-carboxylic acid [4-((3R,6R)-5-amino-3,6-dimethyl-6-trifluoromethyl-3,6-dihydro-2H-[1,4]oxazin-3-yl)-5-fluoro-pyridin-2-yl]-amide A mixture of 5-cyano-3-methyl-pyridine-2-carboxylic acid amide (43.5 mg, 0.270 mmol), (2R,5R)-5-(2-bromo-5-fluoro-pyridin-4-yl)-2,5-dimethyl-2-trifluoromethyl-5,6-dihydro-2H-[1,4]-oxazin-3-ylamine (100.0 mg, 0.270 mmol), Xantphos (14.1 mg, 0.024 mmol) and Cs₂CO₃ (123.0 mg, 0.378 mmol) in dioxane (2.5 ml) was degassed with argon for 5 min, then Pd₂(dba)₃ (7.42 mg, 8.11 μmol) was added and the reaction mixture was stirred at 60° C. for 24 h. The reaction mixture was diluted with H₂O and TBME. The phases were separated and the aq. phase was twice reextracted with TBME. The combined org. phases were washed with brine, dried over Na₂SO₄, filtered and concentrated. Prep HPLC (Alltech Grom Saphir 65 Si 10 μM column, 150×30 mm, gradient n-heptane:EtOAc:MeOH 0-1.2 min 68:30:2, 1.2-9 min 0:80:20, 9-12 min 0:65:35, flow: 50 ml/min, detection: 254 nm) yielded the parent compound as a colourless solid. Rt$_{H4}$=0.83 min; ESIMS: 451 [(M+H)⁺]; ¹H NMR (400 MHz, DMSO-d₆): δ 10.80 (br s, 1H), 8.98 (br s, 1H), 8.42 (s, 1H), 8.36 (dd, 1H), 8.30 (dd, 1H), 6.24 (br s, 2H), 3.97 (d, 1H), 3.82 (d, 1H), 2.58 (s, 3H), 1.49 (s, 3H), 1.44 (s, 3H).

The compound in Table 7 can be prepared by a procedure analogous to that used in Example 16.

TABLE 7

| Example | Compound | ¹H-NMR (δ; DMSO-d₆) | MS [m/z; (M + 1)⁺] |
| --- | --- | --- | --- |
| 17 | 5-Cyano-3-methyl-pyridine-2-carboxylic acid [4-((3S,6R)-5-amino-3,6-dimethyl-6-trifluoromethyl-3,6-dihydro-2H-[1,4]oxazin-3-yl)-5-fluoro-pyridin-2-yl]-amide | 10.75 (s, 1H), 8.97 (s, 1H), 8.42 (s, 2H), 8.27 (d, 1H), 6.21 (br s, 2H), 3.91 (s, 2H), 2.58 (s, 3H), 1.61 (s, 3H), 1.44 (s, 3H). | UPLCMS: Rt$_{H4}$ = 0.79 [M + 1] = 451 |

Example 18

5-Bromo-pyridine-2-carboxylic acid [5-(5-amino-3-fluoromethyl-3,6-dihydro-2H-[1,4]oxazin-3-yl)-6-chloro-pyridin-3-yl]-amide hydrochloride

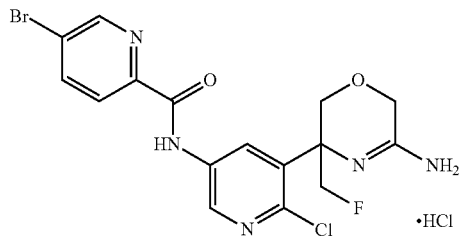 [SMILES: NC1=NC(CF)(c2cc(NC(=O)c3ccc(Br)cn3)cnc2Cl)COC1 ; Cl]

a) 5-Bromo-2-chloro-3-nitromethyl-pyridine

To a solution of 5-bromo-3-bromomethyl-2-chloro-pyridine (4.10 g, 14.37 mmol) in TBME (50.3 ml) in a tin-foil wrapped flask was added silver nitrite (2.65 g, 17.24 mmol) and the reaction mixture was stirred at room temperature for 15 h. The solid was filtered off, rinsed with TBME and the filtrate was evaporated. The residue was purified by chromatography on silica gel (cyclohexane to cyclohexane/EtOAc 3:2) to provide the title compound as pale brown oil.

HPLC: Rt$_{H4}$=0.91 min; ESIMS [M−H]⁻=248.9, 251.0; ¹H-NMR (600 MHz, DMSO-d₆): 8.71 (d, 1H), 8.40 (d, 1H), 5.92 (s, 2H).

b) 2-(5-Bromo-2-chloro-pyridin-3-yl)-2-nitropropane-1,3-diol

To a solution of 5-bromo-2-chloro-3-nitromethyl-pyridine (286 mg, 1.14 mmol) in dioxane (2.3 ml) was added 35% aq.

formaldehyde (215 mg, 2.50 mmol), triethylamine (0.079 ml, 0.57 mmol) and the reaction mixture was stirred at room temperature for 2 h, to the mixture was added a mixture of saturated aq. NaCl and 12N HCl (0.05 ml, 0.6 mmol). Then the mixture was extracted with TBME the combined organic layers were washed with saturated aq. NaCl, dried with $Na_2SO_4$ and evaporated. The residue was purified by chromatography on silica gel (cyclohexane to cyclohexane/EtOAc 1:1) to provide the title compound as colorless solid. M.p. 162-163° C. HPLC: $Rt_{H4}$=0.69 min; ESIMS $[M+H]^+$=311.0, 313.0; $^1$H NMR (600 MHz, DMSO-$d_6$): 8.64 (d, 1H), 8.11 (d, 1H), 5.60 (t, 2H), 4.34 (dd, 2H), 4.19 (dd, 2H).

c) 2-(5-Bromo-2-chloro-pyridin-3-yl)-2-nitropropane-1,3-diol

To a suspension of zinc dust (2.03 g, 31 mmol) in acetic acid (8.6 ml) was added dropwise within 1 h a solution of 2-(5-bromo-2-chloro-pyridin-3-yl)-2-nitropropane-1,3-diol (1.61 g, 5.17 mmol) in acetic acid (17.3 ml) and DMF (5.2 ml), while maintaining the temperature between 30 and 40° C. (ice cooling), the reaction mixture was stirred at 40° C. for 1.5 h. The mixture was filtered, the residue rinsed with methanol and at 0° C. the filtrate poured on a 1:1 mixture of EtOAc and saturated aq. $NaHCO_3$. The pH was adjusted to 12 by addition of 1N NaOH, the layers separated and the aq. phase extracted with EtOAc. The combined organic layers were washed with saturated aq. NaCl, dried with $Na_2SO_4$ and evaporated to provide the title compound as yellow solid.

HPLC: $Rt_{H5}$=0.22 min; ESIMS $[M+H]^+$=281.0, 283.0; $^1$H NMR (400 MHz, DMSO-$d_6$): 8.43 (d, 1H), 8.38 (d, 1H), 4.80 (t, 2H), 3.93 (dd, 2H), 3.67 (dd, 2H), 2.18 (br. s, 2H).

d) N-[1-(5-Bromo-2-chloro-pyridin-3-yl)-2-hydroxy-1-hydroxymethyl-ethyl]-2-chloro-acetamide To a suspension of 2-(5-bromo-2-chloro-pyridin-3-yl)-2-nitropropane-1,3-diol (904 mg, 3.21 mmol) in DCM (64 ml) was added pyridine (2.6 ml, 32.1 mmol), after cooling to –30° C. a solution of chloro-acetylchloride (1.022 ml, 12.84 mmol) in DCM (32 ml) was added within 10 min., the reaction mixture was stirred at –30° C. for 1.5 h. At –30° C. 1M HCl and DCM was added, the layers were separated, the aq. phase extracted with DCM and the combined organic layers washed with halfsaturated aq. $NaHCO_3$ and halfsaturated aq. NaCl, dried with $Na_2SO_4$ and evaporated. The obtained per-acetylated product was dissolved in methanol (19.3 ml) and $K_2CO_3$ powder (222 mg, 1.6 mmol) added, the mixture was stirred at room temperature for 30 min. After addition of 1M HCl and TBME the layers were separated, the aq. layer was extracted with TBME, the combined organic layers were washed with halfsaturated aq. NaCl, dried with $Na_2SO_4$ and evaporated. The residue was purified by chromatography on silica gel (cyclohexane/EtOAc 1:0 to cyclohexane/EtOAc 0:1) to provide the title compound as colorless solid.

HPLC: $Rt_{H5}$=0.51 min; ESIMS $[M+H]^+$=356.9, 358.9; $^1$H NMR (600 MHz, DMSO-$d_6$): 8.44 (d, 1H), 8.27 (s, 1H), 7.99 (s, 1H), 5.08 (t, 2H), 4.11 (s, 2H), 4.00-3.95 (m, 2H), 3.94-3.89 (m, 2H).

e) 5-(5-Bromo-2-chloro-pyridin-3-yl)-5-hydroxymethyl-morpholin-3-one

To a suspension of N-[1-(5-bromo-2-chloro-pyridin-3-yl)-2-hydroxy-1-hydroxymethyl-ethyl]-2-chloro-acetamide (622 mg, 1.74 mmol) in tert.-butanol (10.2 ml) was added at 0° C. potassium tert.-butoxide (292 mg, 2.61 mmol), the reaction mixture was stirred at room temperature for 1 h. Water was added and the tert.-butanol evaporated, the mixture was extracted with EtOAc, the combined organic layers were washed with halfsaturated aq. NaCl, dried with $Na_2SO_4$ and evaporated to provide the title compound as beige foam.

HPLC: $Rt_{H4}$=0.58 min; ESIMS $[M+H]^+$=320.9, 322.9; $^1$H NMR (600 MHz, DMSO-$d_6$): 8.56 (d, 1H), 8.39 (s, 1H), 8.21 (d, 1H), 5.44 (t, 1H), 4.42 (d, 1H), 4.04 (s, 2H), 3.94 (dd, 1H), 3.90 (d, 1H), 3.86 (d, 1H).

f) 5-(5-Bromo-2-chloro-pyridin-3-yl)-5-fluoromethyl-morpholin-3-one

To a suspension of 5-(5-bromo-2-chloro-pyridin-3-yl)-5-hydroxymethyl-morpholin-3-one (547 mg, 1.70 mmol) in THF (13.6 ml) was added at 0° C. within 5 min a solution of DAST (1.01 ml, 7.65 mmol) in THF (7.2 ml), the reaction mixture was stirred at room temperature for 6 h. The mixture was cooled to 0° C., halfsaturated aq. $Na_2CO_3$ was added and the mixture was extracted with EtOAc, the combined organic layers were washed with halfsaturated aq. NaCl, dried with $Na_2SO_4$ and evaporated. The residue was purified by chromatography on silica gel (cyclohexane to cyclohexane/EtOAc 1:4) to provide the title compound as colorless solid.

HPLC: $Rt_{H5}$=0.66 min; ESIMS $[M-H]^-$=320.8, 322.8; $^1$H NMR (600 MHz, DMSO-$d_6$): 8.80 (s, 1H), 8.63 (d, 1H), 8.12 (d, 1H), 5.01-4.93 (m, 1H), 4.92-4.85 (m, 1H), 4.37 (dd, 1H), 4.10 (s, 2H), 3.95 (d, 1H).

g) 5-[5-(Benzhydrylidene-amino)-2-chloro-pyridin-3-yl]-5-fluoromethyl-morpholin-3-one To a solution of 5-(5-bromo-2-chloro-pyridin-3-yl)-5-fluoromethyl-morpholin-3-one (199 mg, 0.615 mmol), benzophenone imine (86 mg, 0.473) and $Cs_2CO_3$ (620 mg, 1.89 mmol) in toluene (4.6 ml) and dioxane (4.6 ml) was added $Pd_2(dba)_3$ (22 mg, 0.024 mmol) and Xantphos (41 mg, 0.071 mmol) and the mixture was purged with nitrogen, the reaction mixture was heated to 100° C. for 4 h. After cooling to 0° C. water was added and the mixture was extracted with EtOAc, the combined organic layers were washed with water, dried with $Na_2SO_4$ and evaporated. The residue was purified by chromatography on silica gel (cyclohexane to cyclohexane/EtOAc 1:4) to provide the title compound as yellowish foam.

HPLC: $Rt_{H5}$=1.11 min; ESIMS $[M+H]^+$=424.1; $^1$H NMR (600 MHz, DMSO-$d_6$): 8.71 (s, 1H), 7.80 (s, 1H), 7.70 (d, 2H), 7.58 (t, 1H), 7.50 (t, 2H), 7.36 (d, 4H), 7.16 (d, 2H), 4.87-4.70 (m, 2H), 4.28 (d, 1H), 4.04 (d, 1H), 3.93 (d, 1H), 3.80 (d, 1H).

h) 5-(5-Amino-2-chloro-pyridin-3-yl)-5-fluoromethyl-morpholine-3-thione

To a solution of 5-[5-(benzhydrylidene-amino)-2-chloro-pyridin-3-yl]-5-fluoromethyl-morpholin-3-one (206 mg, 0.467 mmol) in THF (2.4 ml) was added Lawessons's reagent (189 mg, 0.467 mmol), the reaction mixture was heated to reflux for 1 h. The solvent was evaporated and the crude product dissolved in THF (12 ml), 2M HCl (6.3 ml) were added and the mixture stirred at room temperature for 17 h. After cooling to 0° C. aq. 2M $K_2CO_3$ was added and the basic mixture was extracted with EtOAc, the combined organic layers were washed with halfsaturated aq. NaCl, dried with $Na_2SO_4$ and evaporated. The residue was purified by chromatography on silica gel (cyclohexane/EtOAc 1:0 to cyclohexane/EtOAc 0:1) to provide the title compound as beige foam.

HPLC: $Rt_{H5}$=0.59 min; ESIMS $[M+H]^+$=276.0; $^1$H NMR (600 MHz, DMSO-$d_6$): 10.99 (s, 1H), 7.70 (d, 1H), 7.08 (d, 1H), 5.76 (s, 2H), 4.99 (dd, 1H), 4.82 (dd, 1H), 4.46-4.35 (m, 3H), 3.96 (d, 1H).

i) 5-Bromo-pyridine-2-carboxylic acid [6-chloro-5-(3-fluoromethyl-5-thioxo-morpholin-3-yl)-pyridin-3-yl]-amide A solution of 5-(5-amino-2-chloro-pyridin-3-yl)-5-fluoromethyl-morpholine-3-thione (33 mg, 0.12 mmol), 5-bromo-pyridine-2-carboxylic acid (36 mg, 0.18 mmol) and HOAt (29 mg, 0.215 mmol) in DMF (0.4 ml) was cooled to 0° C. and DIPEA (0.042 ml, 0.24 mmol) and EDC (34 mg, 0.18 mmol) were added, the reaction mixture was stirred at 0° C. for 10 min, then allowed to warm to room temperature over night. At 0° C. aq. 1M $KHCO_3$ was added and the mixture extracted with toluene. The combined organic layers were washed with water, dried with $Na_2SO_4$ and evaporated. The residue was taken up in DCM/MeOH 65/35 from which the product started to crystallize. Filtration, rinsing of the crystallized material with DCM and drying provide the title compound as yellow crystals.

TLC (cyclohexane/EtOAc 1:1) $R_f$=0.45; HPLC: $Rt_{H5}$=1.08 min; ESIMS [M+H]$^+$=458.9, 461.0.

j) 5-Bromo-pyridine-2-carboxylic acid [5-(5-amino-3-fluoromethyl-3,6-dihydro-2H-[1,4]oxazin-3-yl)-6-chloro-pyridin-3-yl]-amide hydrochloride To a suspension of 5-bromo-pyridine-2-carboxylic acid [6-chloro-5-(3-fluoromethyl-5-thioxo-morpholin-3-yl)-pyridin-3-yl]-amide (26 mg, 0.057 mmol) in 7M $NH_3$ in MeOH (0.23 ml) was added at −20° C., tert.-butylhydroperoxide (0.055 ml, 0.566 mmol) and aq. 25% $NH_3$ (0.15 ml, 0.99 mmol), the reaction mixture was stirred at room temperature for 80 min, 7M $NH_3$ in MeOH (0.69 ml) were added and stirring continued for 20 h. At 0° C. halfsaturated aq. $Na_2S_2O_3$ was added and the mixture extracted with EtOAc. The combined organic layers were washed with halfsaturated aq. NaCl, dried with $Na_2SO_4$ and evaporated. The residue was purified by preparative TLC DCM/MeOH 9:1 to yield the desired compound as colorless foam. The product was dissolved in DCM/MeOH, 5 equivalents of 5M HCl in $Et_2O$ were added and the solvents evaporated to provide the title compound as beige solid.

TLC (DCM/MeOH 9:1) $R_f$=0.22; HPLC: $Rt_{H5}$=0.71 min; ESIMS [M+H]$^+$=442.0, 443.9; $^1$H NMR (600 MHz, DMSO-$d_6$): 11.12 (s, 1H), 8.88 (d, 1H), 8.86 (s, 1H), 8.65 (d, 1H), 8.35 (dd, 1H), 8.09 (d, 1H), 6.02 (br. s, 2H), 4.80-4.66 (m, 2H), 4.13-3.93 (m, 4H).

Example 19

3-Amino-5-cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide

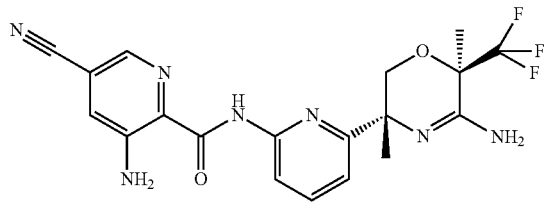 [SMILES: C[C@@]1(c2cccc(NC(=O)c3ncc(C#N)cc3N)n2)CO[C@@](C)(C(F)(F)F)C(N)=N1]

a) (2R,5R)-5-(6-Amino-pyridin-2-yl)-2,5-dimethyl-2-trifluoromethyl-5,6-dihydro-2H-[1,4]oxazin-3-ylamine To a suspension of (2R,5R)-5-(6-bromo-pyridin-2-yl)-2,5-dimethyl-2-trifluoromethyl-5,6-dihydro-2H-[1,4]oxazin-3-ylamine (6.0 g, 17.04 mmol, Example 8 step h), $Cu_2O$ (0.122 g, 0.852 mmol), $K_2CO_3$ (0.471 g, 3.41 mmol) and N,N'-dimethylethylenediamine (0.15 g, 1.704 mmol) were suspended in ethylene glycol (34 ml) were added 53 ml aq. $NH_3$ (25% w). The flask was sealed and the suspension was stirred to 60° C. for 20 h. A green solution was obtained. It was occasionally necessary to shake the flask to make sure that all insoluble parts went in solution. The mixture was partitioned between water and EtOAc. The aq. phase was extracted with EtOAc, the combined org layers were washed with brine, dried with $Na_2SO_4$ and evaporated to give 5.11 g of a green resin, which was purified by chromatography on silica gel (DCM/1-4% (EtOH 25% aq NH3 9:1)) to give 2.77 g of the title compound as a colorless foam.

HPLC: $Rt_{H2}$=2.480 min; ESIMS: 289 [(M+H)$^+$]; $^1$H-NMR (600 MHz, DMSO-$d_6$): 7.31 (t, 1H), 6.63 (d, 1H), 6.27 (d, 1H), 5.89 (br s, 2H), 5.77 (br s, 2H), 3.90 (d, 1H), 3.65 (d, 1H), 1.40 (s, 3H), 1.28 (s, 3H).

b) [(2R,5R)-5-(6-Amino-pyridin-2-yl)-2,5-dimethyl-2-trifluoromethyl-5,6-dihydro-2H-[1,4]oxazin-3-yl]-carbamic acid tert-butyl ester A solution of (2R,5R)-5-(6-amino-pyridin-2-yl)-2,5-dimethyl-2-trifluoromethyl-5,6-dihydro-2H-[1,4]oxazin-3-ylamine (2.77 g, 9.61 mmol), $Boc_2O$ (2.31 g, 10.57 mmol) and DIPEA (2.2 ml, 12.5 mmol) in DCM (28 ml) and THF (2 ml) was stirred for 3 days. The mixture was evaporated and purified by chromatography on silica gel (hexanes/10-20% EtOAc) to give 3.34 g of the title compound as a colorless solid. HPLC: $Rt_{H3}$=3.048 min; ESIMS: 389 [(M+H)$^+$]; $^1$H-NMR (600 MHz, DMSO-$d_6$): 10.88 (s, 1H), 7.43 (t, 1H), 6.48 (d, 1H), 6.41 (d, 1H), 6.01 (br s, 2H), 4.16 (d, 1H), 4.11 (d, 1H), 1.54 (s, 3H), 1.52 (s, 3H), 1.45 (s, 9H).

c) ((2R,5R)-5-{6-[(3-Amino-5-cyano-pyridine-2-carbonyl)-amino]-pyridin-2-yl}-2,5-dimethyl-2-trifluoromethyl-5,6-dihydro-2H-[1,4]oxazin-3-yl)-carbamic acid tert-butyl ester A mixture of [(2R,5R)-5-(6-amino-pyridin-2-yl)-2,5-dimethyl-2-trifluoromethyl-5,6-dihydro-2H-[1,4]oxazin-3-yl]-carbamic acid tert-butyl ester (80 mg, 0.206 mmol), 3-amino-5-cyano-pyridine-2-carboxylic acid (40.3 mg, 0.247 mmol, Acid-4, HOAt (50.5 mg, 0.371 mmol) in DMF (1 ml) and EDC.HCl (59.2 mg, 0,309 mmol) was stirred overnight. The reaction mixture was diluted with EtOAc, washed with aq. $NaHCO_3$ and brine, and dried with $MgSO_4.H_2O$. The title compound was obtained after chromatography on silica gel (toluene/1-3% EtOAc) to give 71 mg of the title compound as a pale yellow solid slightly contaminated with some starting material. HPLC: $Rt_{H1}$=3.608 min; ESIMS: 534 [(M+H)$^+$]; $^1$H-NMR (600 MHz, CDCl$_3$): 10.92 (s, 1H), 8.29 (d, 1H), 8.18 (s, 1H), 7.82 (t, 1H), 7.36 (s, 1H), 7.14 (d, 1H), 6.33 (br, 1H), 4.39 (d, 1H), 4.12 (d, 1H), 1.66 (s, 3H), 1.60 (s, 9H), 1.59 (s, 3H).

d) 3-Amino-5-cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide To a solution of ((2R,5R)-5-{6-[(3-amino-5-cyano-pyridine-2-carbonyl)-amin]-pyridin-2-yl}-2,5-dimethyl-2-trifluoromethyl-5,6-dihydro-2H-[1,4]oxazin-3-yl)-carbamic acid tert-butyl ester (71 mg, 0.133 mmol) in DCM (3 ml) was added TFA (1 ml). After stirring for 1.5 h the mixture was poured onto 10% aq. $Na_2CO_3$ and extracted three times with DCM. The combined organic layers were dried with K₂CO₃, filtered and evaporated. The title compound (46 mg) was obtained after chromatography on silica gel (hexanes/15-25% (EtOAc/EtOH 9:1)) as a yellow solid. HPLC: Rt$_{H3}$=3.027 min; ESIMS: 434 [(M+H)⁺]; ¹H-NMR (600 MHz, DMSO-d₆): 10.23 (s, 1H), 8.25 (s, 1H), 8.06 (d, 1H), 7.85 (t, 1H), 7.69 (s, 1H), 7.36-7.27 (m, broad, 3H), 6.12-6.00, (s, broad, 2H), 3.94 (d, 1H), 3.76 (d, 1H), 1.42 (s, 3H), 1.34 (s, 3H).

Examples 20 to 23

The compounds listed in Table 8 can be prepared by a procedure analogous to that used in Example 19.

Hydrochloride salts were obtained from solutions of the corresponding free base by addition of hydrochloric acid in dioxane or hydrochloric acid in diethylether and evaporation of the solvents.

TABLE 8

| Example | Compound | ¹H-NMR | MS [m/z; (M + 1)⁺] |
|---|---|---|---|
| 20 | 3-Chloro-5-cyano-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide | (δ; DMSO-d₆): 11.04 (br s, 1H), 9.07 (s, 1H), 8.78 (s, 1H), 8.02 (d, 1H), 7.86-7.82 (m, 1H), 7.34 (d, 1H), 6.02 (br s, 2H), 3.92 (d, 1H), 3.73 (d, 1H), 1.41 (s, 3H), 1.32 (s, 3H) | UPLCMS: Rt$_{H4}$ = 0.78 [M + 1] = 453 |
| 21 | 5-Chloro-4,6-dideuterio-3-trideuteriomethyl-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide | (δ; DMSO-d₆; 600 MHz): 10.41 (s, 1H), 8.08 (d, 1H), 7.83 (t, 1H), 7.30 (d, 1H), 6.10-5.98, (s, broad, 2H), 3.94 (d, 1H), 3.74 (d, 1H), 1.42 (s, 3H), 1.33 (s, 3H). | LCMS: Rt$_{H3}$ = 3.367 [M + 1] = 447, 449 |
| 22 | 5-Bromo-3-chloro-pyridine-2-carboxylic acid [6-((3R,6R)-5-amino-3,6-dimethyl-6-trifluoromethyl-3,6-dihydro-2H-[1,4]oxazin-3-yl)-pyridin-2-yl]-amide | (δ; DMSO-d₆; 600 MHz): 10.86 (s, 1H), 8.78 (s, 1H), 8.53 (s, 1H), 8.02 (d, 1H), 7.84 (t, 1H), 7.28 (d, 1H), 6.10-6.01, (s, broad, 2H), 3.94 (d, 1H), 3.73 (d, 1H), 1.41 (s, 3H), 1.32 (s, 3H). | LCMS: Rt$_{H3}$ = 3.180 [M + 1] = 506, 508, 510 |
| 23 | 3-Amino-5-(2,2,2-trifluoro-ethoxy)-pyrazine-2-carboxylic acid [6-((3R,6R)-5-amino-3,6-dimethyl-6-trifluoromethyl-3,6-dihydro-2H-[1,4]oxazin-3-yl)-pyridin-2-yl]-amide | (δ; DMSO-d₆; 600 MHz): 9.88 (s, 1H), 8.05-7.72 (s, broad, 2H), 8.03 (d, 1H), 7.82 (t, 1H), 7.72 (s, 1H), 7.28 (d, 1H), 6.08-6.01, (s, broad, 2H), 5.03 (q, 2H), 3.92 (d, 1H), 3.74 (d, 1H), 1.41 (s, 3H), 1.33 (s, 3H). | LCMS: Rt$_{H3}$ = 3.343 [M + 1] = 508 |

Example 24

3-Chloro-5-cyano-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide

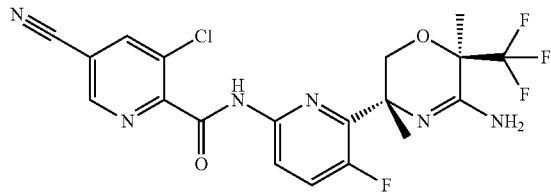 [SMILES: C[C@@]1(c2nc(NC(=O)c3ncc(C#N)cc3Cl)ccc2F)CO[C@@](C)(C(F)(F)F)C(N)=N1]

a) (2R,5R)-5-(6-Amino-3-fluoro-pyridin-2-yl)-2,5-dimethyl-2-trifluoromethyl-5,6-dihydro-2H-[1,4]oxazin-3-yl amine and (2R,5S)-5-(6-Amino-3-fluoro-pyridin-2-yl)-2,5-dimethyl-2-trifluoromethyl-5,6-dihydro-2H-[1,4]oxazin-3-yl amine A glass/stainless steel autoclave was purged with nitrogen and then a mixture of (2R,5S)-5-(6-bromo-3-fluoro-pyridin-2-yl)-2,5-dimethyl-2-trifluoromethyl-5,6-dihydro-2H-[1,4]oxazin-3-ylamine and (2R,5R)-5-(6-Bromo-3-fluoro-pyridin-2-yl)-2,5-dimethyl-2-trifluoromethyl-5,6-dihydro-2H-[1,4]oxazin-3-ylamine (13.3 g, 35.9 mmol, ca. 1:3 mixture, Example 11 (step k) or see alternative procedure below), Cu$_2$O (1.271 g, 8.88 mmol) and ammonia (150 ml, 25%, aq., 1078 mmol, 30 equivalents) in ethylene glycol (215 ml) was added. The autoclave was closed and the suspension heated up to 60° C. and the solution was stirred for about 48 hours (max. Pressure 0.9 bar, inside temperature 58-60° C.). The reaction mixture was diluted with ethyl acetate and water. The organic phase was washed with water and brine, dried over sodium sulfate, filtered and evaporated. The dark green crude product (13.64 g, containing some ethylen glycol, quantitative yield) was used in the next step without further purification.

LCMS: Rt$_{H4}$=0.62 min (23%, ES+307) and Rt$_{H4}$=0.65 min (74%, ES+307)

b) [(2R,5R)-5-(6-Amino-3-fluoro-pyridin-2-yl)-2,5-dimethyl-2-trifluoromethyl-5,6-dihydro-2H-[1,4]oxazin-3-yl]-carbamic acid tert-butyl ester and [(2R,5S)-5-(6-Amino-3-fluoro-pyridin-2-yl)-2,5-dimethyl-2-trifluoromethyl-5,6-dihydro-2H-[1,4]oxazin-3-yl]-carbamic acid tert-butyl ester A solution of (2R,5R)-5-(6-amino-3-fluoro-pyridin-2-yl)-2,5-dimethyl-2-trifluoromethyl-5,6-dihydro-2H-[1,4]oxazin-3-yl amine and (2R,5S)-5-(6-Amino-3-fluoro-pyridin-2-yl)-2,5-dimethyl-2-trifluoromethyl-5,6-dihydro-2H-[1,4]oxazin-3-yl amine (10.99 g, 35.9 mmol, ca. 3:1 mixture), Boc$_2$O (7.05 g, 32.3 mmol) and Hünig's base (7.52 ml, 43.1 mmol) in dichloromethane (120 ml) was stirred at 0° C. for 4 hours and then at rt over night. The reaction mixture was evaporated and the residue was diluted with ethyl acetate. Crushed ice was added and the mixture was washed with water and brine, dried over sodium sulfate, filtered and evaporated. The crude product (14.23 g) was triturated with toluene/cyclo-hexane/ethyl acetate 4:4:2, cooled and filtered. 5.14 g colorless solid. The filtrate was evaporated and the resulting mixture was filtered over silica (TBME) to give the 2 isomers as an 8:2 mixture (6.31 g). The colorless solid (5.14 g) was dissolved in dichloromethane and chromatographed over silicagel (toluene/cyclohexane/ethyl acetate 4:4:2) to afford the two isomers.

[(2R,5R)-5-(6-Amino-3-fluoro-pyridin-2-yl)-2,5-dimethyl-2-trifluoromethyl-5,6-dihydro-2H-[1,4]oxazin-3-yl]-carbamic acid tert-butyl ester 1.38 g, TLC R$_f$=0.16 (toluene:cyclohexane:ethyl acetate 4:4:2), [α]–86.4°, c=0.975 (19.5 mg in 2 ml CHCl$_3$), LC/MS Rt$_{H4}$=1.17 min (100%, ES+ 407/408), HPLC chiral (CHIRACEL oj-h, heptane/ethanol/methanol 80:10:10+0.1% dea) Rt=3.937 min (99.16%),% ee 98.3%. $^1$H-NMR (400 MHz, CDCl3): 11.50 (s, 1H, NH), 7.24 (t, 1H), 6.47 (br. d, 1H), 4.55-4.40 (br. s, 2H, NH$_2$), 4.35 (d, 1H, AB), 4.10 (d, 1H, AB-system), 1.71 (s, 3H, CH3), 1.69 (s, 3H, CH3), 1.55 (s, 9H).

[(2R,5S)-5-(6-Amino-3-fluoro-pyridin-2-yl)-2,5-dimethyl-2-trifluoromethyl-5,6-dihydro-2H-[1,4]oxazin-3-yl]-carbamic acid tert-butyl ester 1.12 g, TLC R$_f$=0.19 (toluene:cyclohexane:ethyl acetate 4:4:2), [α]+72.9°, c=1.01 (20.2 mg in 2 ml CHCl$_3$), LC/MS Rt$_{H4}$=1.16 min (100%, ES+ 407/408), HPLC chiral (CHIRACEL oj-h, heptane/ethanol/methanol 80:10:10+0.1% dea) Rt=5.36 min (99.44%),% ee 98.9%. $^1$H-NMR (400 MHz, CDCl$_3$): 11.65 (s, 1H, NH), 7.23 (t, 1H), 6.47 (br. d, 1H), 4.55-4.40 (br. s, 2H, NH2), 4.35 (dd, 1H, AB), 4.24 (d, 1H, AB-system), 1.78 (s, 3H, CH3), 1.70 (s, 3H, CH3), 1.58 (s, 9H).

Mixed fractions (2.53 g) and recovered material from the filtrate (6.31 g) were purified separately affording additional 4.13 g of [(2R,5R)-5-(6-amino-3-fluoro-pyridin-2-yl)-2,5-dimethyl-2-trifluoromethyl-5,6-dihydro-2H-[1,4]oxazin-3-yl]-carbamic acid tert-butyl ester and 1.07 g of [(2R,5S)-5-(6-amino-3-fluoro-pyridin-2-yl)-2,5-dimethyl-2-trifluoromethyl-5,6-dihydro-2H-[1,4]oxazin-3-yl]-carbamic acid tert-butyl ester.

c) ((2R,5R)-5-{6-[3-Chloro-5-cyano-pyridine-2-carbonyl)-amino]-3-fluoro-pyridin-2-yl}-2,5-dimethyl-2-trifluoromethyl-5,6-dihydro-2H-[1,4]oxazin-3-yl)-carbamic acid tert-butyl ester A mixture of [(2R,5R)-5-(6-amino-3-fluoro-pyridin-2-yl)-2,5-dimethyl-2-trifluoromethyl-5,6-dihydro-2H-[1,4]oxazin-3-yl]-carbamic acid tert-butyl ester (406 mg, 0.999 mmol), 3-chloro-5-cyanopicolinic acid (201 mg, 1.099 mmol), HOAt (245 mg, 1.798 mmol) and EDC hydrochloride (287 mg, 1.499 mmol) was stirred in DMF (10.2 ml) at rt for 44 hours. The reaction mixture was diluted with toluene and washed with sat. aq. sodium bicarbonate solution, water and brine, dried over sodium sulfate, filtered and evaporated. The crude product (595 mg) was chromatographed over silicagel (toluene: ethyl acetate 9:1) to yield the title compound: 455 mg (76% yield).

TLC (silica, toluene:ethyl acetate 9:1) R$_f$=0.28; ESIMS [M+H]$^+$571, 573;

$^1$H-NMR (400 MHz, CDCl$_3$): 11.7 (s, 1H, NH), 10.33 (s, 1H), 8.80 (s, 1H), 8.45 (br. d, 1H), 8.24 (s, 1H), 7.60 (br. t, 1H), 4.40 (d, 1H, AB), 4.20 (d, 1H, AB), 1.75 (s, 3H), 1.68 (s, 3H), 1.62 (s, 9H).

d) 3-Chloro-5-cyano-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide A mixture of ((2R,5R)-5-{6-[3-chloro-5-cyano-pyridine-2-carbonylamino]-3-fluoro-pyridin-2-yl}-2,5-dimethyl-2-trifluoromethyl-5,6-dihydro-2H-[1,4]oxazin-3-yl)-carbamic acid tert-butyl ester (450 mg, 0.788 mmol) and TFA (0.90 ml, 11.68 mmol) in dichloromethane (9 ml) was stirred at rt for 5 hours. The solvent was evaporated and the residue diluted with ethyl acetate and aq. ammonia. Ice was added and the organic phase was washed with water and brine, dried over sodium sulfate, filtered and evaporated. Colorless solid: 360 mg (96% yield).

LC-MS: $Rt_{H4}$=0.79 min (99%, ESI+471, 473);
$^1$H-NMR (400 MHz, CDCl$_3$): 10.2 (br. s, 1H, NH), 8.85 (d, 1H), 8.35 (dd, 1H), 8.20 (d, 1H), 7.50 (dd, 1H), 4.32 (d, 1H, AB), 3.93 (d, 1H, AB), 1.64 (s, 3H), 1.54 (s, 3H).

Alternative stereoselective procedure for the preparation of (2R,5R)-5-(6-bromo-3-fluoro-pyridin-2-yl)-2,5-dimethyl-2-trifluoromethyl-5,6-dihydro-2H-[1,4]oxazin-3-ylamine a) 2-Bromo-5-fluoro-4-triethylsilanyl-pyridine

A solution of diisopropylamine (25.3 g, 250 mmol) in 370 ml THF was cooled with a dry-ice acetone bath at −75° C. BuLi (100 ml, 250 mmol, 2.5 M in hexanes) was added dropwise while maintaining the temperature below −50° C. After the temperature of the mixture had reached −75° C. again, a solution of 2-bromo-5-fluoropyridine (36.7 g, 208 mmol) in 45 ml THF was added dropwise. The mixture was stirred for 1 h at −75° C. Triethylchlorosilane (39.2 g, 260 mmol) was added quickly. The temperature stayed below −50° C. The cooling bath was removed and the reaction mixture was allowed to warm to −15° C., poured onto aq. NH$_4$Cl (10%). TBME was added and the layers were separated. The organic layer was washed with brine, dried with MgSO$_4$.H$_2$O, filtered and evaporated to give a brown liquid which was distilled at 0.5 mm Hg to yield the title compound as a slightly yellow liquid (b.p. 105-111° C.). HPLC: $Rt_{H11}$=2.284 min; ESIMS: 290, 292 [(M+H)$^+$, 1Br]; $^1$H-NMR (400 MHz, CDCl$_3$): 8.14 (s, 1H), 7.40 (d, 1H), 1.00-0.82 (m, 15H).

b) 1-(6-Bromo-3-fluoro-4-triethylsilanyl-pyridin-2-yl)-ethanone

A solution of diisopropylamine (25.4 g, 250 mmol) in 500 ml THF was cooled to −75° C. BuLi (100 ml, 250 mmol, 2.5 M in hexanes) was added dropwise while maintaining the temperature below −50° C. After the reaction temperature had reached −75° C. again, a solution of 2-bromo-5-fluoro-4-triethylsilanyl-pyridine (56.04 g, 193 mmol) in 60 ml THF was added dropwise. The mixture was stirred in a dry ice bath for 70 minutes. N,N-dimethylacetamide (21.87 g, 250 mmol) was added quickly, the reaction temperature rose to −57° C. The reaction mixture was stirred in a dry ice bath for 15 min and then allowed to warm to −40° C. It was poured on a mixture of 2M aq. HCl (250 ml, 500 mmol), 250 ml water and 100 ml brine. The mixture was extracted with TBME, washed with brine, dried over MgSO$_4$.H$_2$O, filtered and evaporated to give a yellow oil which was purified on a silica gel column by eluting with hexane/0-5% TBME to yield 58.5 g of the title compound as a yellow liquid. TLC (Hex/TBME 99/1): $R_f$=0.25; HPLC: $Rt_{H11}$=1.921 min; ESIMS: 332, 334 [(M+H)$^+$, 1Br]; $^1$H-NMR (400 MHz, CDCl$_3$): 7.57 (d, 1H), 2.68 (s, 3H), 1.00-0.84 (m, 15H).

c) (S)-2-(6-Bromo-3-fluoro-4-triethylsilanyl-pyridin-2-yl)-2-trimethylsilanyloxy-propionitrile At first, the catalyst solution was prepared by dissolving water (54 mg, 3.00 mmol) in 100 ml dry DCM (≤0.001% water). This wet DCM (44 ml, 1.32 mmol water content) was added to a well stirred solution of titanium(IV) butoxide (500 mg, 1.47 mmol) in 20 ml dry DCM. The resulting clear solution was refluxed for 1 h. This solution was then cooled to rt and 2,4-di-tert-butyl-6-{[(E)-(S)-1-hydroxymethyl-2-methyl-propylimino]-methyl}-phenol [CAS 155052-31-6] (469 mg, 1.47 mmol) was added. The resulting yellow solution was stirred at rt for 1 h. This catalyst solution (0.023 M, 46.6 ml, 1.07 mmol) was added to a solution of 1-(6-bromo-3-fluoro-4-triethylsilanyl-pyridin-2-yl)-ethanone (35.53 g, 107 mmol) and trimethylsilyl cyanide (12.73 g, 128 mmol) in 223 ml dry DCM. The mixture was stirred for 2 days and evaporated to give 47 g of the crude title compound as an orange oil. HPLC: $Rt_{H12}$=2.773 min; ESIMS: 431, 433 [(M+H)$^+$, 1Br]; $^1$H-NMR (400 MHz, CDCl$_3$): 7.46 (d, 1H), 2.04 (s, 3H), 1.00 (t, 9H), 1.03-0.87 (m, 15H), 0.20 (s, 9H).

d) (R)-1-Amino-2-(6-bromo-3-fluoro-4-triethylsilanyl-pyridin-2-yl)-propan-2-ol hydrochloride Borane dimethyl sulfide complex (16.55 g, 218 mmol) was added to a solution of crude (S)-2-(6-bromo-3-fluoro-4-triethylsilanyl-pyridin-2-yl)-2-trimethylsilanyloxy-propionitrile (47 g, 109 mmol) in 470 ml THF. The mixture was refluxed for 2 h. The heating bath was removed and the reaction mixture was quenched by careful and dropwise addition of MeOH. After the evolution of gas had ceased, aq. 6M HCl (23.6 ml, 142 mmol) was added slowly. The resulting solution was evaporated and the residue was dissolved in MeOH and evaporated (twice) to yield 44.5 g of a yellow foam, pure enough for further reactions. HPLC: $Rt_{H1}$=2.617 min; ESIMS: 363, 365 [(M+H)$^+$, 1Br]; $^1$H-NMR (400 MHz, CDCl$_3$): 7.93 (s, br, 3H), 7.53 (d, 1H), 6.11 (s, br, 1H), 3.36-3.27 (m, 1H), 3.18-3.09 (m, 1H), 1.53 (s, 3H), 0.99-0.81 (m, 15H).

e) (R)—N-(2-(6-bromo-3-fluoro-4-(triethylsilyl)pyridin-2-yl)-2-hydroxypropyl)-4-nitrobenzenesulfonamide To a solution of crude (R)-1-amino-2-(6-bromo-3-fluoro-4-triethylsilanyl-pyridin-2-yl)-propan-2-ol hydrochloride (43.5 g, 109 mmol) in 335 ml THF was added a solution of NaHCO$_3$ (21.02 g, 250 mmol) in 500 ml water. The mixture was cooled to 0-5° C. and a solution of 4-nitrobenzenesulfonyl chloride (26.5 g, 120 mmol) in 100 ml THF was added in a dropwise. The resulting emulsion was stirred overnight while allowing the temperature to reach rt. The mixture was extracted with TBME. The organic layer was dried with MgSO$_4$.H$_2$O, filtered and evaporated to give an orange resin which was purified on a silca gel column by eluting with Hexanes/10-20% EtOAc to yield 37.56 g of the title compound as a yellow resin. TLC (Hex/EtOAc 3/1) $R_f$=0.34; HPLC: $Rt_{H11}$=1.678 min; ESIMS: 548, 550 [(M+H)$^+$, 1Br]; $^1$H-NMR (400 MHz, DMSO-d$_6$): 8.40 (d, 2H), 8.06 (t, 1H), 7.97 (d, 2H), 7.45 (d, 1H), 5.42 (s, 1H), 3.23 (d, 2H), 1.44 (s, 3H) 0.97-0.81 (m, 15H); Chiral HPLC (Chiralpak AD-H 1213, UV 210 nm): 90% ee.

f) 6-Bromo-3-fluoro-2-[(S)-2-methyl-1-(4-nitro-benzenesulfonyl)-aziridin-2-yl]-4-triethylsilanyl-pyridine A solution of triphenylphosphine (21.55 g, 82 mmol) and (R)—N-(2-(6-bromo-3-fluoro-4-(triethylsilyl)pyridin-2-yl)-2-hydroxypropyl)-4-nitrobenzenesulfonamide (37.56 g, 69 mmol) in 510 ml THF was cooled to 4° C. A solution of diethyl azodicarboxylate in toluene (40% by weight, 38.8 g, 89 mmol) was added in a dropwise while maintaining the temperature below 10° C. The cooling bath was removed and the rm was stirred at rt for 1 h. The reaction mixture was diluted with approx. 1000 ml toluene and THF was removed by evaporation at the rotavap. The resulting toluene solution of crude product was pre-purified on a silca gel column by eluting with hexanes/5-17% EtOAc. Purest fractions were combined, evaporated and crystallized from TBME/hexane to yield 29.2 g of the title compound as white crystals. HPLC: $Rt_{H11}$=2.546 min; ESIMS: 530, 532 [(M+H)$^+$, 1 Br]; $^1$H-NMR (400 MHz, CDCl$_3$): 8.40 (d, 2H), 8.19 (d, 2H), 7.39 (d, 1H), 3.14 (s, 1H), 3.02 (s, 1H), 2.01 (s, 3H) 1.03-0.83 (m, 15H); α[D]-35.7° (c=0.97, DCM).

g) 6-Bromo-3-fluoro-2-[(S)-2-methyl-1-(4-nitro-benzenesulfonyl)-aziridin-2-yl]-pyridine Potassium fluoride (1.1 g, 18.85 mmol) was added to a solution of 6-bromo-3-fluoro-2-[(S)-2-methyl-1-(4-nitro-benzenesulfonyl)-aziridin-2-yl]-4-triethylsilanyl-pyridine (5 g, 9.43 mmol) and AcOH (1.13 g, 9.43 mmol) in 25 ml THF. DMF (35 ml) was added and the suspension was stirred for 1 h at rt. The reaction mixture was poured onto a mixture of sat. aq. NaHCO$_3$ and TBME. The layers were separated and washed with brine and TBME. The combined organic layers were dried over MgSO$_4$.H$_2$O, filtered and evaporated to give a yellow oil which was crystallized from TBME/hexane to yield 3.45 g of the title compound as white crystals. HPLC: $Rt_{H13}$=2.612 min; ESIMS: 416, 418 [(M+H)$^+$, 1Br]; $^1$H-NMR (400 MHz, CDCl$_3$): 8.41 (d, 2H), 8.19 (d, 2H), 7.48 (dd, 1H), 7.35 (t, 1H), 3.14 (s, 1H), 3.03 (s, 1H), 2.04 (s, 3H); α[D]-35.7° (c=0.89, DCM).

h) (R)-2-[(R)-2-(6-Bromo-3-fluoro-pyridin-2-yl)-2-(4-nitro-benzenesulfonylamino)-propoxy]-3,3,3-trifluoro-2-methyl-propionic acid ethyl ester A solution of (R)-3,3,3-trifluoro-2-hydroxy-2-methyl-propionic acid ethyl ester (11.93 g, 64.1 mmol) in DMF (158 ml) was evacuated/flushed with nitrogen twice. A solution of KOtBu (6.21 g, 55.5 mmol) in DMF (17 ml) was added in a dropwise while maintaining a reaction temperature of ca 25° C. using cooling with a water bath. After 15 min solid 6-bromo-3-fluoro-2-[(S)-2-methyl-1-(4-nitro-benzenesulfonyl)-aziridin-2-yl]-pyridine (17.78 g, 42.7 mmol) was added and stirring was continued for 3 h. The reaction mixture was poured onto a mixture of 1M HCl (56 ml), brine and TBME. The layers were separated, washed with brine and TBME. The combined organic layers were dried over MgSO$_4$.H$_2$O, filtered and evaporated. The crude reaction product was purified via chromatography on silica gel (hexanes/25-33% TBME) to yield 16.93 g of the title compound as a yellow resin that was contaminated with an isomeric side-product (ratio 70:30 by $^1$H-NMR).
HPLC: $Rt_{H13}$=2.380 min; ESIMS: 602, 604 [(M+H)$^+$, 1 Br]; $^1$H-NMR (400 MHz, CDCl$_3$): 8.32 (d, 2H), 8.07 (d, 2H), 7.46-7.41 (m, 1H), 7.30-7.23 (m, 1H), 6.92 (s, 1H), 3.39-4.30 (m, 2H), 3.95 (d, 1H), 3.84 (d, 1H), 1.68 (s, 3H), 1.56 (s, 3H), 1.40-1.34 (m, 3H)+isomeric side-product.

i) (R)-2-[(R)-2-(6-Bromo-3-fluoro-pyridin-2-yl)-2-(4-nitro-benzenesulfonylamino)-propoxy]-3,3,3-trifluoro-2-methyl-propionamide A solution of (R)-2-[(R)-2-(6-bromo-3-fluoro-pyridin-2-yl)-2-(4-nitro-benzenesulfonylamino)-propoxy]-3,3,3-trifluoro-2-methyl-propionic acid ethyl ester (16.93 g, 28.1 mmol) in a NH$_3$/MeOH (7M, 482 ml) was stirred at 50° C. in a sealed vessel for 26 h. The reaction mixture was evaporated and the residue was crystallized from DCM to yield 9.11 g of the title compound as colorless crystals.
HPLC: $Rt_{H13}$=2.422 min; ESIMS: 573, 575 [(M+H)$^+$, 1 Br]; $^1$H-NMR (400 MHz, CDCl$_3$): 8.33 (d, 2H), 8.06 (d, 2H), 7.42 (dd, 1H), 7.30-7.26 (m, 1H), 7.17 (s, br, 1H), 6.41 (s, 1H), 5.57 (s, br, 1H), 4.15 (m, 2H), 1.68 (s, 3H), 1.65 (s, 3H).

j) N—[(R)-1-(6-Bromo-3-fluoro-pyridin-2-yl)-2-(R)-1-cyano-2,2,2-trifluoro-1-methyl-ethoxy)-1-methyl-ethyl]-4-nitro-benzenesulfonamide A suspension of (R)-2-[(R)-2-(6-bromo-3-fluoro-pyridin-2-yl)-2-(4-nitro-benzenesulfonylamino)-propoxy]-3,3,3-trifluoro-2-methyl-propionamide (8.43 g, 14.70 mmol) and triethylamine (5.12 ml, 36.8 mmol) in 85 ml DCM was cooled to 0-5° C. Trifluoroacetic anhydride (2.49 ml, 17.64 mmol) was added dropwise over 30 min. Additional triethylamine (1.54 ml, 11.07 mmol) and trifluoroacetic anhydride (0.75 ml, 5.29 mmol) were added to complete the reaction. The reaction mixture was quenched by addition of 14 ml aqueous ammonia (25%) and 14 ml water. The emulsion was stirred for 15 min, more water and DCM were added and the layers were separated. The organic layer was dried with MgSO$_4$ H$_2$O, filtered and evaporated. Purification by column chromatography on a silica gel (hexanes/10-25% EtOAc) gave 8.09 g of the title compound as a yellow resin.
HPLC: $Rt_{F13}$=3.120 min; ESIMS: 555, 557 [(M+H)$^+$, 1Br]; $^1$H-NMR (400 MHz, CDCl$_3$): 8.35 (d, 2H), 8.11 (d, 2H), 7.50 (dd, 1H), 7.32 (dd, 1H), 6.78 (s, 1H), 4.39 (d 1H), 4.22 (d, 1H), 1.68 (s, 6H).

k) (2R,5R)-5-(6-Bromo-3-fluoro-pyridin-2-yl)-2,5-dimethyl-2-trifluoromethyl-5,6-dihydro-2H-[1,4] oxazin-3-ylamine A solution of N—[(R)-1-(6-bromo-3-fluoro-pyridin-2-yl)-2-((R)-1-cyano-2,2,2-trifluoro-1-methyl-ethoxy)-1-methyl-ethyl]-4-nitro-benzenesulfonamide (9.18 g, 16.53 mmol) and N-acetylcysteine (5.40 g, 33.10 mmol) in 92 ml ethanol was evacuated and flushed with nitrogen. K$_2$CO$_3$ (4.57 g, 33.1 mmol) was added and the mixture was stirred at 80° C. for 3 days. The reaction mixture was concentrated in vacuo to about ¼ of the original volume and partitioned between water and TBME. The organic layer was washed with 10% aq. K$_2$CO$_3$ solution, dried over Na$_2$SO$_4$, filtered and evaporated to give a yellow oil. Column chromatography on silica (hexanes/14-50% (EtOAc:MeOH 95:5)) gave 4.55 g of the title compound as an off-white solid.
HPLC: $Rt_{H3}$=2.741 min; ESIMS: 370, 372 [(M+H)$^+$, 1Br]; $^1$H-NMR (400 MHz, DMSO-d$_6$): 7.71-7.62 (m, 2H), 5.97 (s, br, 2H), 4.02 (d 1H), 3.70 (d, 1H), 1.51 (s, 3H), 1.47 (s, 3H).

Examples 25 to 34

The compounds in Table 9 were prepared by similar procedures as for Example 11 or Example 24; Example 28 required intermediate [(2R,5S)-5-(6-Amino-3-fluoro-pyridin-2-yl)-2,5-dimethyl-2-trifluoro-methyl-5,6-dihydro-2H-[1,4]oxazin-3-yl]-carbamic acid tert-butyl ester from Example 24 (step b, second isomer).

TABLE 9

| Example | Compound | ¹H-NMR | MS [m/z; (M + 1)⁺] |
|---|---|---|---|
| 25 | 5-Methoxy-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 600 MHz): 10.40 (br. s, 1H, NH), 8.28 (d, 1H), 8.18 (br. d, 1H), 7.72 (t, 1H), 7.44 (d, 1H), 6.00 (br. s, 2H, NH₂), 4.11 (d, 1H, AB), 3.91 (s, 3H), 3.75 (d, 1H, AB), 2.70 (s, 3H), 1.50 (s, 3H), 1.49 (s, 3H). | LCMS: Rt$_{H4}$ = 0.88; [M + 1]⁺ = 456.4 |
| 26 | 3-Amino-5-(2,2,2-trifluoro-ethoxy)-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆ + 1 drop TFA, 600 MHz): 10.10 (br. s, 1H, NH), 9.68 (s, 1H, NH-amidine), 9.50 (s, 1H, NH-amidine), 8.26 (dd, 1H), 8.20-7.70 (broad, 2H, NH₂-pyrazine), 7.92 (t, 1H), 7.67 (s, 1H), 5.02 (q, 2H), 4.40 (d, 1H, AB), 4.25 (d, 1H, AB), 1.70 (s, 3H), 1.68 (s, 3H). | LCMS: Rt$_{H4}$ = 0.93; [M + 1]⁺ = 526.3 |
| 27 | 3-Amino-5-cyano-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 600 MHz): 10.30 (br. s, 1H, NH), 8.23 (d, 1H), 8.12 (br. d, 1H), 7.75 (t, 1H), 7.69 (d, 1H), 7.31 (br. s, 2H, NH₂-pyridine), 5.95 (br. s, 2H, NH₂-amidine), 4.11 (d, 1H, AB), 3.72 (d, 1H, AB), 1.50 (s, 3H), 1.49 (s, 3H). | LCMS: Rt$_{H4}$ = 0.86; [M + 1]⁺ = 452.1 |
| 28 | 3-Chloro-5-cyano-pyridine-2-carboxylic acid [6-((3S,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 600 MHz): 11.10 (s, 1H, NH), 9.10 (s, 1H), 8.79 (s, 1H), 8.10 (br. d, 1H), 7.72 (br. t, 1H), 5.90 (br. s, 2H, NH₂-amidine), 4.20 (br. s, 1H, AB), 3.70 (br. s, 1H, AB), 1.60 (s, 3H), 1.50 (s, 3H). | LCMS: Rt$_{H4}$ = 0.77; [M + 1]⁺ = 471.1 |

TABLE 9-continued

| Example | Compound | ¹H-NMR | MS [m/z; (M + 1)⁺] |
|---|---|---|---|
| 29 | 5-Difluoromethoxy-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 600 MHz): 10.45 (br. s, 1H, NH), 8.44 (s, 1H), 8.18 (d, 1H), 7.76 (s, 1H), 7.72 (t, 1H), 7.45 (t, 1H), 5.90 (br. s, 2H, NH₂), 4.11 (d, 1H, AB), 3.72 (d, 1H, AB), 2.68 (s, 3H), 1.50 (s, 3H), 1.49 (s, 3H). | LCMS: Rt$_{H4}$ = 0.90; [M + 1]⁺ = 492.3 |
| 30 | 3-Chloro-5-difluoromethoxy-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 600 MHz): 10.90 (br. s, 1H, NH), 8.59 (s, 1H), 8.11 (d, 1H), 8.10 (s, 1H), 7.72 (t, 1H), 7.49 (t, 1H), 5.88 (br. s, 2H, NH₂), 4.11 (d, 1H, AB), 3.72 (d, 1H, AB), 1.50 (s, 3H), 1.49 (s, 3H). | LCMS: Rt$_{H4}$ = 0.85; [M + 1]⁺ = 512.2 |
| 31 | 3,5-Dichloro-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 10.92 (br. s, 1H, NH), 8.73 (br. s, 1H), 8.44 (d, 1H), 8.12 (dd, 1H), 7.73 (dd, 1H), 5.88 (br. s, 2H, NH2), 4.11 (d, 1H, AB), 3.72 (d, 1H, AB), 1.51 (s, 3H), 1.48 (s, 3H). | LCMS: Rt$_{H4}$ = 0.86; [M + 1]+ = 480, 482, 484 |
| 32 | 5-Fluoromethoxy-3-methyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 10.42 (br. s, 1H, NH), 8.43 (d, 1H), 8.16 (dd, 1H), 7.73 (dd, 1H), 7.66 (d, 1H), 6.04 (d, 2H, CH₂F), 5.91 (br. s, 2H, NH2), 4.13 (d, 1H, AB), 3.74 (d, 1H, AB), 2.70 (s, 3H), 1.51 (s, 3H), 1.49 (s, 3H). | LCMS: Rt$_{H4}$ = 0.87; [M + 1]+ = 474 |

TABLE 9-continued

| Example | Compound | ¹H-NMR | MS [m/z; (M + 1)⁺] |
|---|---|---|---|
| 33 | 5-Methyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 10.19 (br. s, 1H, NH), 9.22 (d, 1H), 8.73 (d, 1H), 8.18 (dd, 1H), 7.79 (dd, 1H), 5.92 (br. s, 2H, NH2), 4.15 (d, 1H, AB), 3.76 (d, 1H, AB), 2.66 (s, 3H), 1.52 (s, 3H), 1.50 (s, 3H). | LCMS: Rt$_{H4}$ = 0.78; [M + 1]⁺ = 427 |
| 34 | 3-Chloro-5-trifluoromethyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 11.15 (br. s, 1H, NH), 9.06 (s, 1H), 8.69 (s, 1H), 8.13 (dd, 1H), 7.75 (dd, 1H), 5.88 (br. s, 2H, NH2), 4.13 (d, 1H, AB), 3.73 (d, 1H, AB), 1.52 (s, 3H), 1.49 (s, 3H). | LCMS: Rt$_{H4}$ = 0.93; [M + 1]+ = 514, 516 |

Examples 35 to 36

The compounds in Table 10 can be prepared by a procedure analogous to that used in Example 16.

TABLE 10

| Example | Compound | ¹H-NMR (δ; DMSO-d₆) | MS [m/z; (M + 1)⁺] |
|---|---|---|---|
| 35 | 3-Chloro-5-cyano-pyridine-2-carboxylic acid [4-((3R,6R)-5-amino-3,6-dimethyl-6-trifluoromethyl-3,6-dihydro-2H-[1,4]oxazin-3-yl)-5-fluoro-pyridin-2-yl]-amide | 11.23 (br s, 1H), 9.08 (d, 1H), 8.79 (d, 1H), 8.33-8.30 (m, 2H), 6.23 (br s, 2H), 3.97 (d, 1H), 3.82 (d, 1H), 1.49 (s, 3H), 1.44 (s, 3H) | UPLCMS: Rt$_{H4}$ = 0.78 [M + 1] = 471.2 |

| Example | Compound | ¹H-NMR (δ; DMSO-d₆) | MS [m/z; (M + 1)⁺] |
|---|---|---|---|
| 36 | 3-Chloro-5-difluoromethoxy-pyridine-2-carboxylic acid [4-((3R,6R)-5-amino-3,6-dimethyl-6-trifluoromethyl-3,6-dihydro-2H-[1,4]oxazin-3-yl)-5-fluoro-pyridin-2-yl]-amide | 10.95 (s, 1H), 8.56 (d, 1H), 8.37-8.25 (m, 2H), 8.09 (d, 1H), 7.48 (t, 1H), 6.23 (br s, 2H), 3.97 (d, 1H), 3.82 (d, 1H), 1.49 (s, 3H), 1.44 (s, 3H) | UPLCMS: Rt$_{H4}$ = 0.89 [M + 1] = 512.2 |

Example 37

5-Cyano-3-methyl-pyridine-2-carboxylic acid [4-((R)-5-amino-6,6-bis-fluoromethyl-3-methyl-3,6-dihydro-2H-[1,4]oxazin-3-yl)-5-fluoro-pyridin-2-yl]-amide a) 2-[2-(2-Bromo-5-fluoro-pyridin-4-yl)-2-(2-nitro-benzenesulfonylamino)-propoxy]-3-fluoro-2-fluoromethyl-propionic acid ethyl ester A solution of 3-fluoro-2-fluoromethyl-2-hydroxy-propionic acid ethyl ester (see Intermediates Hydroxyester 1, 0.606 g, 3.60 mmol) in DMF (7 ml) was predried over activated 4 Å molecular sieves, then a suspension of NaH (0.135 g of a 60% dispersion in mineral oil, 3.36 mmol) was added and the reaction mixture was stirred at rt for 10 min. A solution of 2-bromo-5-fluoro-4-[2-methyl-1-(2-nitro-benzenesulfonyl)-aziridin-2-yl]-pyridine (see Example 16, step g, 1.0 g, 2.403 mmol) in DMF (7 ml, soln. predried over activated 4 Å molecular sieves) was slowly added. The reaction mixture was stirred at rt for 3.5 h, then quenched with aq. 1N HCl soln. and diluted with H₂O and TBME. The phases were separated and the aq. layer was twice reextracted with TBME. The combined organic layers were washed with H₂O, dried over Na₂SO₄, filtered and concentrated. The resulting crude title compound was purified by NP-HPLC (Alltech Grom Saphir65 Si 10 μm column, 250×50 mm, gradient n-heptane:EtOAc 75:25 to 0:100).

HPLC: Rt$_{H4}$=1.18 min; ESIMS [M+H]⁺=584, 586 (1Br); ¹H-NMR (400 MHz, DMSO-d₆): δ 8.76 (s, 1H), 8.21 (d, 1H), 7.94-7.92 (m, 2H), 7.88-7.75 (m, 2H), 7.70 (d, 1H), 4.85-4.46 (m, 4H), 4.20 (q, 2H), 4.04 (d, 1H), 3.83 (d, 1H), 1.62 (s, 3H), 1.21 (t, 3H).

b) 2-[2-(2-Bromo-5-fluoro-pyridin-4-yl)-2-(2-nitro-benzenesulfonylamino)-propoxy]-3-fluoro-2-fluoromethyl-propionamide A solution of 2-[2-(2-bromo-5-fluoro-pyridin-4-yl)-2-(2-nitro-benzenesulfonylamino)-propoxy]-3-fluoro-2-fluoromethyl-propionic acid ethyl ester (970 mg, 1.660 mmol) and 7M NH₃ in MeOH (10 ml) was stirred in a in a sealed glass vial at 55° C. for 20 h. Another 3 ml of 7N NH₃/MeOH were added and stirring was continued for 16 h at 55° C. The reaction mixture was concentrated and yielded the title compound as a yellow solid that was used in the next step without further purification.

HPLC: Rt$_{H4}$=0.95 min; ESIMS [M+H]⁺=555, 557 (1Br); ¹H-NMR (400 MHz, DMSO-d₆): δ 9.01 (s, 1H), 8.25 (d, 1H), 7.99-7.90 (m, 2H), 7.85-7.58 (m, 5H), 4.73-4.51 (m, 4H), 3.96 (d, 1H), 3.90 (d, 1H), 1.58 (s, 3H).

c) N-[1-(2-Bromo-5-fluoro-pyridin-4-yl)-2-(cyano-bis-fluoromethyl-methoxy)-1-methyl-ethyl]-2-nitro-benzenesulfonamide To a solution of 2-[2-(2-bromo-5-fluoro-pyridin-4-yl)-2-(2-nitro-benzenesulfonylamino) propoxy]-3-fluoro-2-fluoromethyl-propionic acid ethyl ester (900 mg, 1.621 mmol) in DCM (11 ml) was added NEt₃ (0.565 ml, 410 mg, 4.050 mmol). The reaction mixture was cooled to 0° C., then TFA anhydride (0.275 ml, 408 mg, 1.945 mmol) was added dropwise. The reaction mixture was allowed to warm to rt and to stir for 18 h. In order to obtain complete conversion, the reaction mixture was cooled again to 0° C. and more TFA anhydride (0.450 ml, 670 mg, 3.190 mmol) followed by NEt₃ (0.230 ml, 168 mg, 1.659 mmol) was added and the reaction mixture was allowed to warm to rt and to stir for another 30 min.

The reaction mixture was diluted with sat. aq. Na₂CO₃ soln. and DCM. The phases were separated and the aq. phase was twice reextracted with DCM. The combined organic phases were washed with brine, dried over Na₂SO₄, filtered and concentrated. The resulting crude title compound was purified by NP-HPLC (Alltech Grom Saphir65 Si 10 μm column, 150×30 mm, gradient n-heptane:EtOAc 85:15 to 0:100).

HPLC: Rt$_{H4}$=1.09 min; ESIMS [M+H]⁺=537, 339 (1Br); ¹H-NMR (400 MHz, DMSO-d₆): δ 9.02 (s, 1H), 8.24 (d, 1H), 7.94-7.90 (m, 2H), 7.87-7.75 (m, 2H), 7.61 (d, 1H), 4.95-4.48 (m, 4H), 4.14-4.02 (m, 2H), 1.60 (s, 3H).

d) 5-(2-Bromo-5-fluoro-pyridin-4-yl)-2,2-bis-fluoromethyl-5-methyl-5,6-dihydro-2H-[1,4]oxazin-3-ylamine A solution of N-[1-(2-bromo-5-fluoro-pyridin-4-yl)-2-(cyano-bis-fluoromethyl-methoxy)-1-methyl-ethyl]-2-nitrobenzenesulfonamide (840 mg, 1.563 mmol), N-acetyl-L-cysteine (510 mg, 3.13 mmol) and $K_2CO_3$ (432 mg, 3.130 mmol) in abs. EtOH (10 ml) was stirred at 85° C. for 18 h. N-acetyl-L-cysteine (250 mg, 1.533 mmol) and $K_2CO_3$ (210 mg, 1.519 mmol) was added and stirring at 85° C. was continued for 18 h. The reaction mixture was concentrated to ⅓ of its volume, quenched with 10% aq. $K_2CO_3$ soln. and 3× extracted with TBME. The combined org. phases were washed with sat. aq. $NaHCO_3$ soln, brine, dried over $Na_2SO_4$, filtered and concentrated to leave the crude title compound that was purified by NP-HPLC (Alltech Grom Saphir65 Si 10 μm column, 150×30 mm, gradient n-heptane:EtOAc:MeOH 68:30:2 to 0:65:35),
HPLC: $Rt_{H4}$=0.57 min; ESIMS $[M+H]^+$=352, 354 (1Br);
$^1$H-NMR (400 MHz, DMSO-$d_6$): δ 8.35 (d, 1H), 7.76 (d, 1H), 6.32 (br s, 2H), 4.98-4.71 (m, 2H), 4.66-4.39 (m, 2H), 3.94 (dd, 1H), 3.82 (d, 1H), 1.40 (s, 3H).

e) 5-Cyano-3-methyl-pyridine-2-carboxylic acid [4-(5-amino-6,6-bis-fluoromethyl-3-methyl-3,6-dihydro-2H-[1,4]oxazin-3-yl)-5-fluoro-pyridin-2-yl]-amide A mixture of 5-cyano-3-methyl-pyridine-2-carboxylic acid amide (see Intermediates Amide 1, 96 mg, 0.596 mmol), 5-(2-bromo-5-fluoro-pyridin-4-yl)-2,2-bis-fluoromethyl-5-methyl-5,6-dihydro-2H-[1,4]oxazin-3-ylamine (210 mg, 0.596 mmol), Xantphos (31.1 mg, 0.054 mmol) and $Cs_2CO_3$ (272 mg, 0.835 mmol) in dioxane (6 ml) was degassed with argon, $Pd_2(dba)_3$ (16.38 mg, 0.018 mmol) was added and the reaction mixture was stirred at 60° C. for 16 h. More $Pd_2(dba)_3$ (8.19 mg, 0.009 mmol) and Xantphos (15.60 mg, 0.027 mmol) was added and stirring was continued at 60° C. for 4 h. The reaction mixture was filtered through celite and the celite pad rinsed with DCM. The combined filtrates were concentrated and the resulting crude title compound was purified by NP-HPLC (Alltech Grom Saphir65 Si 10 μm column, 150×30 mm, gradient n-heptane:EtOAc:MeOH 68:30:2 to 0:65:35), then by RP-HPLC (Waters SunFire C18 column, 5 μM, 30×100 mm, gradient 10 to 30% ACN+0.1% TFA) and obtained as a free base after filtration over an SCX cartridge.
HPLC: $Rt_{H4}$=0.72 min; ESIMS $[M+H]^+$=433;
$^1$H-NMR (400 MHz, DMSO-$d_6$): δ 10.75 (s, 1H), 8.98 (s, 1H), 8.42 (s, 2H), 8.28 (s, 1H), 6.20 (br s, 2H), 5.05-4.45 (m, 4H), 4.02-3.84 (m, 2H), 2.58 (s, 3H), 1.45 (s, 3H)

f) 5-Cyano-3-methyl-pyridine-2-carboxylic acid [4-((R)-5-amino-6,6-bis-fluoromethyl-3-methyl-3,6-dihydro-2H-[1,4]oxazin-3-yl)-5-fluoro-pyridin-2-yl]-amide Racemic (5-cyano-3-methyl-pyridine-2-carboxylic acid [4-(5-amino-6,6-bis-fluoromethyl-3-methyl-3,6-dihydro-2H-[1,4]oxazin-3-yl)-5-fluoro-pyridin-2-yl]-amide was separated into the pure enantiomers by preparative chiral HPLC (column: Chiralpak AD-H 20×250 mm, 5 uM; solvent: n-heptane/ethanol 75:25; flow: 12 ml/min; detection at 220 nm). Enantiomer 1: Rt 8.964 min. Enantiomer 2: Rt 16.220 min (determined by analytical HPLC using Chiralpak AD-H 250×4.6 mm, 5 uM column; solvent: n-heptane/ethanol/MeOH 70:25:5+DEA; flow: 1.600 ml/min; detection at 220 nm). The absolute configuration of enantiomer 2 was assigned (R) in analogy to similar structures of which the configuration has been determined by X-ray crystallography.
$^1$H-NMR (400 MHz, DMSO-$d_6$): δ 10.76 (s, 1H), 8.98 (s, 1H), 8.42 (s, 2H), 8.28 (s, 1H), 6.21 (br s, 2H), 5.02-4.45 (m, 4H), 3.95 (d, 1H), 3.89 (d, 1H), 2.58 (s, 3H), 1.44 (s, 3H).

Example 38

5-Cyano-3-methyl-pyridine-2-carboxylic acid [6-((R)-5-amino-3-difluoromethyl-3,6-dihydro-2H-[1,4]oxazin-3-yl)-5-fluoro-pyridin-2-yl]-amide

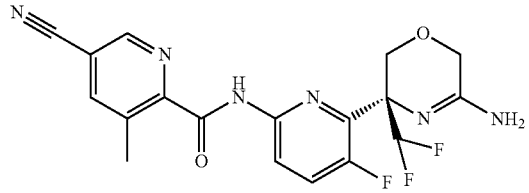 [SMILES: Cc1cc(C#N)cnc1C(=O)Nc1ccc(F)c([C@]2(C(F)F)COCC(N)=N2)n1]

a) 2-Bromo-5-fluoro-4-triethylsilanylpyridine

To a solution of diisopropylamine (25.3 g, 250 mmol) in THF (400 ml) was added n-BuLi (100 ml, 2.5 mol/L in hexanes) below −50° C. A solution of 2-bromo-5-fluoropyridine (41.9 g, 238 mmol) in THF (60 ml) was added to the LDA-solution at −78° C. in a dropwise manner below −63° C. After 60 minutes at −78° C. triethylchlorosilane (44 ml, 262 mmol) was added in a fast manner keeping the temperature below −50° C. The cooling bath was removed and the reaction mixture was allowed to reach −20° C. The reaction mixture was poured on a mixture of 1M aq. HCl (250 ml) and aq. $NH_4Cl$ (10%). Tert.-butyl methyl ether was added and the layers were separated. The organic phase was washed with brine, dried over magnesium sulfate, filtered and evaporated to give a yellow liquid. Distillation (bp. 99-101° C., 0.5 mm Hg). afforded the title compound as a slightly yellow liquid: 66.26 g (96% yield)
$^1$H-NMR (400 MHz, CDCl$_3$): 8.17 (s, 1H), 7.42 (d, 1H), 1.01-0.97 (m, 9H), 0.92-0.87 (m, 6H).

b) 1-(6-Bromo-3-fluoro-4-triethylsilanyl-pyridin-2-yl)-2,2-difluoro-ethanone

To a freshly prepared solution of LDA (6.25 mmol) in THF (5 ml) was added dropwise a solution of 2-bromo-5-fluoro-4-triethylsilanylpyridine (1.6 g, 5.51 mmol) in THF (12 ml) at −78° C. Stirring was continued at −78° C. for 3 hours. Ethyl 2,2-difluoroacetate (0.58 ml, 5.51 mmol) was added dropwise and the solution was stirred at −78° C. for 3 hours. The reaction mixture was quenched with sat. ammonium chloride solution (20 ml) and ethyl acetate was added. The organic phase was washed with brine, dried over sodium sulfate, filtered and evaporated. The crude brown oil (2.11 g) was chromatographed over silica gel (cyclohexane/ethyl acetate) to give the title compound. 1.53 g (75% yield, mixture of ketone and hydrate form).
TLC (cyclohexane/ethyl acetate 10:1) $R_f$=0.26; $^1$H-NMR (400 MHz, CDCl$_3$): 7.70 (d, 1H), 6.96 (t, 1H, CHF$_2$)), 1.02-0.98 (m, 9H), 0.96-0.92 (m, 6H).

c) (S)-2-Methyl-propane-2-sulfinic acid[1-(6-bromo-3-fluoro-4-triethylsilanyl-pyridin-2-yl)-2,2-difluoro-ethylidene]-amide A mixture of 1-(6-bromo-3-fluoro-4-triethylsilanyl-pyridin-2-yl)-2,2-difluoro-ethanone (9.8 g, 26.6 mmol), (S)-2-methylpropane-2-sulfinamide (3.23 g, 26.6 mmol) and tetraethoxytitanium (13.81 ml, 53.2 mmol) in THF (66.5 ml) was stirred at 80° C. in 3 capped microwave vials (3×25 ml) for 3 hours. The cold reaction mixture was poured into ice cold water and the precipitate was filtered through a pad of hyflo and washed thoroughly with ethyl acetate. The organic phase was washed with brine, dried over sodium sulfate, filtered and evaporated. The crude product (12.5 g) was chromatographed over silica gel (cyclohexane:ethyl acetate 5:1) to afford the title compound. 7.96 g (63% yield).

TLC (cyclohexane/ethyl acetate 5:1) $R_f$=0.65; LCMS $Rt_{H4}$=1.53 min. (100% pure, ESI+471, 473); $^1$H-NMR (400 MHz, CDCl$_3$): 7.50 (d, 1H), 6.49 (t, 1H, CHF$_2$), 1.33 (s, 9H), 1.03-0.98 (m, 9H), 0.93-0.89 (m, 6H).

d) (S)-2-Methyl-propane-2-sulfinic acid[(S)-1-(6-bromo-3-fluoro-4-triethylsilanyl-pyridin-2-yl)-1-difluoromethyl-allyl]-amide and (S)-2-Methyl-propane-2-sulfinic acid[(R)-1-(6-bromo-3-fluoro-4-triethylsilanyl-pyridin-2-yl)-1-difluoromethyl-allyl]-amide Vinylmagnesium bromide 1M in THF (2.3 ml, 2.3 mmol) was added to dichloromethane (5 ml) and the solution was cooled down to −78° C. (S)-2-Methyl-propane-2-sulfinic acid[1-(6-bromo-3-fluoro-4-triethylsilanyl-pyridin-2-yl)-2,2-difluoro-ethylidene]-amide (500 mg, 1.06 mmol) in dichloromethane (5 ml) was added dropwise to the above solution keeping the temperature below −65° C. After 30 minutes the reaction was quenched at −78° C. with ammonium chloride solution (10%) and the reaction mixture was extracted with TBME. The organic layer was washed with brine, dried over sodium sulfate, filtered and evaporated. 620 mg (quant. yield) as a 4:1 mixture of diastereoisomers used without purification in the next step.

TLC (cyclohexane/ethyl acetate 10:1) $R_f$=0.15 and (cyclohexane/ethyl acetate 10:1);

$R_f$=0.10; LCMS $Rt_{H4}$=1.50 min. (ESI+499, 501); $^1$H-NMR (400 MHz, CDCl$_3$): 8.56 (s, 1H, NH), 7.47 and 7.45 (d, 1H), 6.60-6.30 (t, 1H, CHF$_2$), 6.25-6.16 (m, 1H), 5.65-5.30 (m, 2H), 1.34 and 1.31 (s, 9H), 0.99-0.96 (m, 9H), 0.90-0.84 (m, 6H).

e) (S)-2-Methyl-propane-2-sulfinic acid [(R)-1-(6-bromo-3-fluoro-4-triethylsilylanyl-pyridin-2-yl)-2,2-difluoro-1-hydroxymethyl-ethyl]-amide and (S)-2-Methyl-propane-2-sulfinic acid [(S)-1-(6-bromo-3-fluoro-4-triethylsilylanyl-pyridin-2-yl)-2,2-difluoro-1-hydroxymethyl-ethyl]-amide A mixture of (S)-2-methyl-propane-2-sulfinic acid[(S)-1-(6-bromo-3-fluoro-4-triethylsilanyl-pyridin-2-yl)-1-difluoromethyl-allyl]-amide and (S)-2-Methyl-propane-2-sulfinic acid[(R)-1-(6-bromo-3-fluoro-4-triethylsilanyl-pyridin-2-yl)-1-difluoromethyl-allyl]-amide from step d) (5.137 g, 10.28 mmol) was dissolved in dichloromethane (77 ml) and methanol (25.7 ml), sodium bicarbonate (1.296 g, 15.43 mmol) was added and the reaction mixture was cooled to −78° C. Ozone was bubbled through the solution until a blue coloration appeared (4 hr). Excess ozone was blown out with nitrogen until the blue color has disappeared. Sodium borohydride (1.945 g, 51.4 mmol) was added to the solution and the reaction mixture was stirred at −78° C. for 3 hours. The reaction mixture was diluted with TBME and 2N HCl to destroy excess sodium borohydride. The organic layer was washed carefully with 1N HCl solution and brine, dried over sodium sulfate, filtered and evaporated. 6.15 g yellow oil. The crude product was chromatographed over silica gel (120 g, cyclohexane/ethyl acetate 3:1) to give the title compounds:

(S)-2-Methyl-propane-2-sulfinic acid [(R)-1-(6-bromo-3-fluoro-4-triethylsilylanyl-pyridin-2-yl)-2,2-difluoro-1-hydroxymethyl-ethyl]-amide 2.36 g (45.6% yield).

TLC (cyclohexane/ethyl acetate 3:1) $R_f$=0.24; LCMS $Rt_{H4}$=1.36 min. (93% pure, ESI+ 503, 505);

$^1$H-NMR (400 MHz, CDCl$_3$): 7.46 (d, 1H), 6.24 (t, 1H, CHF$_2$), 4.60 (br. s, 1H, NH), 4.47 (br. s, 2H, AB), 3.48 (br. s, 1H, OH), 1.32 (s, 9H), 0.99 (t, 9H), 0.89 (q, 6H).

(S)-2-Methyl-propane-2-sulfinic acid [(S)-1-(6-bromo-3-fluoro-4-triethylsilylanyl-pyridin-2-yl)-2,2-difluoro-1-hydroxymethyl-ethyl]-amide 1.72 g (33.2% yield).

TLC (cyclohexane/ethyl acetate 3:1) $R_f$=0.31;

LCMS $Rt_{H4}$=1.43 min. (100% pure, ESI+ 503, 505);

$^1$H-NMR (400 MHz, CDCl$_3$): 7.47 (d, 1H), 6.62 (br. s, 1H), 6.23 (t, 1H, CHF$_2$), 4.51-4.48 (d, 1H, AB), 4.36-4.32 (d, 1H, AB), 1.42 (s, 9H), 0.99 (t, 9H), 0.89 (q, 6H).

f) (R)-2-Amino-2-(6-bromo-3-fluoro-4-triethylsilanyl-pyridin-2-yl)-3,3-difluoro-propan-1-ol To a solution of (S)-2-methyl-propane-2-sulfinic acid [(R)-1-(6-bromo-3-fluoro-4-triethylsilylanyl-pyridin-2-yl)-2,2-difluoro-1-hydroxymethyl-ethyl]-amide (2.3 g, 4.57 mmol) in dichloromethane (45 ml) was added HCl (5.48 ml, 16.45 mmol, 3 molar in methanol) and the reaction mixture was stirred for 5 hours at room temperature. The solvent was removed in vacuo and the residue diluted with ethyl acetate and poured onto a mixture of ammonia 2N/ice. The layers were separated and the organic phase was washed with water and brine, dried over sodium sulfate, filtered and evaporated. 2.15 g. Used in next step without further purification.

LCMS $Rt_{H4}$=1.18 min. (94% purity, ESI+399, 401); $^1$H-NMR (400 MHz, CDCl$_3$): 7.43 (d, 1H), 6.16 (t, 1H, CHF$_2$), 4.13-4.10 (d, 1H, AB), 3.99-3.93 (d, 1H, AB), 2.52 (br. s, 3H, OH, NH$_2$), 0.99 (t, 9H), 0.89 (q, 6H).

g) N—[(R)-1-(6-Bromo-3-fluoro-4-triethylsilanyl-pyridin-2-yl)-2,2-difluoro-1-hydroxymethyl-ethyl]-2-chloro-acetamide To a solution of (R)-2-amino-2-(6-bromo-3-fluoro-4-triethylsilanyl-pyridin-2-yl)-3,3-difluoro-propan-1-ol (2.15 g, 5.38 mmol) in dichloromethane (14.55 ml) was added an aq. sodium carbonate solution (14.55 ml, 10% aq. solution) at 0° C. 2-Chloroacetyl chloride (0.518 ml, 6.46 mmol) was added dropwise at 0° C. and the ice bath was removed after the addition. The reaction mixture was stirred at rt for 15 min. Methanol was added and the reaction mixture was stirred at 50° C. for 10 min. The reaction mixture was diluted with dichloromethane and water. The mixture was extracted with dichloromethane, dried over sodium sulfate, filtered and evaporated. The crude light yellow oil (2.91 g) was chromatographed over silica gel (40 g redisep column, cyclohexane/ethyl acetate 10-70%) to give the title compound. 2.32 g (91% yield).

TLC (cyclohexane/ethyl acetate 2:1) R$_f$=0.53; LCMS Rt$_{H4}$=1.30 min. (ESI+475, 477, 479);

$^1$H-NMR (400 MHz, CDCl$_3$): 8.17 (br. s, 1H, NH), 7.47 (d, 1H), 6.58 (t, 1H, CHF$_2$), 4.64-4.55 (m, 1H, AB), 4.20-4.12 (m, 3H, AB), 0.98 (t, 9H), 0.89 (q, 6H).

h) (R)-5-(6-Bromo-3-fluoro-pyridin-2-yl)-5-difluoromethyl-morpholin-3-one

To a solution of N—[(R)-1-(6-bromo-3-fluoro-4-triethylsilanyl-pyridin-2-yl)-2,2-difluoro-1-hydroxymethyl-ethyl]-2-chloro-acetamide (2.32 g, 4.88 mmol) in t-butanol (50 ml) was added potassium tert-butoxide (7.31 ml, 7.31 mmol, 1M in THF) and the solution was stirred in a closed vial for 18 h at 100° C. The reaction mixture was diluted with ethyl acetate, washed with water, sat. NaHSO$_4$ solution and brine, dried over sodium sulfate, filtered and evaporated. The crude product (2.36 g) was chromatographed over silica gel (24 g redisep column, cyclohexane/ethyl acetate 10-80%) to give the title compound. 1.13 g (71% yield). Triethylsilylated lactam (640 mg) was recovered.

TLC (cyclohexane/ethyl acetate 1:1) R$_f$=0.25;

LCMS Rt$_{H4}$=0.79 min. (ESI+325, 327); $^1$H-NMR (400 MHz, CDCl$_3$): 7.59-7.57 (m, 1H), 7.51 (br. s, 1H, NH), 7.45-7.42 (m, 1H), 6.23 (t, 1H, CHF$_2$), 4.86 (d, 1H, AB), 4.38 (d, 1H, AB), 4.16 (d, 1H, AB), 3.97 (d, 1H, AB).

i) (R)-5-(6-Bromo-3-fluoro-pyridin-2-yl)-5-difluoromethyl-morpholin-3-thione To a solution of (R)-5-(6-bromo-3-fluoro-pyridin-2-yl)-5-difluoromethyl-morpholin-3-one (1.13 g, 3.48 mmol) in pyridine (34.8 ml) was added phosphorous pentasulfide, the vial was sealed and the reaction mixture was stirred at 100° C. for 2 h. The reaction mixture was diluted with 2M HCl solution and ethyl acetate. The organic layer was washed with brine, dried over sodium sulfate, filtered and evaporated. The crude product (1.4 g) was used in the next step without purification.

LCMS Rt$_{H4}$=0.98 min. (ESI+ 341, 343); $^1$H-NMR (400 MHz, CDCl$_3$): 9.40 (br. s, 1H, NH), 7.62 (dd, 1H), 7.45 (dd, 1H), 6.25 (t, 1H, CHF$_2$), 4.93 (dd, 1H, AB), 4.79 (d, 1H, AB), 4.44 (d, 1H, AB), 4.00 (dd, 1H, AB).

j) (R)-5-(6-Bromo-3-fluoro-pyridin-2-yl)-5-difluoromethyl-5,6-dihydro-2H-[1,4]oxazin-3-ylamine To a solution of (R)-5-(6-bromo-3-fluoro-pyridin-2-yl)-5-difluoromethyl-morpholin-3-thione (611 mg, 1.79 mmol) in methanol (15 ml) was added ammonia (5.12 ml, 35.8 mmol, 7M in methanol), the vial was sealed and the reaction mixture was stirred at rt for 20 h. The reaction mixture was diluted with ethyl acetate. The organic layer was washed with aq. sodium thiosulfate solution (10%), water and brine, dried over sodium sulfate, filtered and evaporated. The crude product (640 mg) was chromatographed over silica gel (14 g, dichloromethane/methanol 95/5+0.5% NH$_3$) to give the title compound. 180 mg (31% yield).

LCMS Rt$_{H4}$=0.55 min. (ESI+325, 327); $^1$H-NMR (400 MHz, CDCl$_3$): 7.45 (dd, 1H), 7.32 (dd, 1H), 6.31 (t, 1H, CHF$_2$), 4.38 (d, 1H, AB), 4.22 (d, 1H, AB), 4.15 (d, 1H, AB), 4.10 (d, 1H, AB), 3.0-1.5 (very br. s, 2H, NH$_2$).

k) [(R)-5-(6-Bromo-3-fluoro-pyridin-2-yl)-5-difluoromethyl-5,6-dihydro-2H-[1,4]oxazin-3-yl]-carbamic acid tert-butyl ester A solution of (R)-5-(6-bromo-3-fluoro-pyridin-2-yl)-5-difluoromethyl-5,6-dihydro-2H-[1,4]oxazin-3-ylamine (180 mg, 0.555 mmol), BOC-anhydride (121 mg, 0.555 mmol) and Hünig's base (108 mg, 0.833 mmol) in dichloromethane (5.5 ml) was stirred at rt for 18 h. The reaction mixture was diluted dichloromethane and washed with aq. saturated bicarbonate solution and brine, dried over sodium sulfate, filtered and evaporated. The crude product (352 mg light yellow solid) was chromatographed over silica gel (4 g, cyclohexane/ethyl acetate 5-40%) to give the title compound. 190 mg (81% yield).

TLC (cyclohexane/ethyl acetate 3:1) R$_f$=0.30;

LCMS Rt$_{H4}$=1.11 min. (93% purity, ESI+424, 426); $^1$H-NMR (400 MHz, DMSO-d$_6$): 9.97 (s, 1H, NH), 7.77-7.75 (m, 2H), 6.40 (t, 1H, CHF$_2$), 4.51 (br. s, 2H, AB), 4.21 (d, 1H, AB), 3.88 (d, 1H, AB), 1.41 (s, 9H).

l) ((R)-5-{6-[(5-Cyano-3-methyl-pyridine-2-carbonyl)-amino]-3-fluoro-pyridin-2-yl}-5-difluoromethyl-4,6-dihydro-2H-[1,4]oxazin-3-yl)-carbamic acid tert-butyl ester A mixture of [(R)-5-(6-bromo-3-fluoro-pyridin-2-yl)-5-difluoromethyl-5,6-dihydro-2H-[1,4]oxazin-3-yl]-carbamic acid tert-butyl ester (90 mg, 0.212 mmol), 4-cyano-3-methyl-pyridine-2-carboxylic acid amide (41 mg, 0.255 mmol), XANTPHOS (11.05 mg, 0.019 mmol) and cesium carbonate (97 mg, 0.297 mmol) in dioxane (3 ml) was degassed with argon for 5 minutes. Pd2(dba)$_3$ (5.83 mg, 6.36 µmol) was added and the sealed vial was heated at 60° C. for 18 h. The reaction mixture was diluted with water and TBME. The phases were separated and the aq. phase was extracted with TBME. The combined organic layers were washed with brine, dried over sodium sulfate, filtered and evaporated. The crude product was chromatographed over silica gel (12 g redisep column, cyclohexane/ethyl acetate 5-40%) to give the title compound. 76 mg (71% yield).

TLC (cyclohexane/ethyl acetate 3:1) R$_f$=0.15; LCMS Rt$_{H4}$=1.16 min. (100% purity, ESI+505).

m) 5-Cyano-3-methyl-pyridine-2-carboxylic acid [6-((R)-5-amino-3-difluoromethyl-3,6-dihydro-2H-[1,4]oxazin-3-yl)-5-fluoro-pyridin-2-yl]-amide A solution of ((R)-5-{6-[(5-cyano-3-methyl-pyridine-2-carbonyl)-amino]-3-fluoro-pyridin-2-yl}-5-difluoromethyl-4,6-dihydro-2H-[1,4]oxazin-3-yl)-carbamic acid tert-butyl ester (75 mg, 0.149 mmol) and TFA (115 µl, 1.48 mmol) in dichloromethane was stirred at rt for 2 h. The reaction mixture was diluted with ethyl acetate and poured into an ice/ammonia 2M mixture. The organic layer was washed with water and brine, dried over sodium sulfate, filtered and evaporated. 62 mg solid (quantitative yield).

TLC (dichloromethane/methanol 95/5+0.5% ammonia) R$_f$=0.21;

LCMS Rt$_{H4}$=0.75 min. (ESI+ 405); $^1$H-NMR (400 MHz, DMSO-d$_6$): 10.75 (br. s, 1H, NH), 9.02 (s, 1H), 8.44 (s, 1H), 8.20 (d, 1H), 7.78 (t, 1H), 6.36 (t, 1H, CHF$_2$), 6.06 (br. s, 2H, NH$_2$), 4.27 (d, 1H, AB), 4.04-3.86 (m, 3H, AB), 2.61 (s, 3H).

Example 39

5-Cyano-3-methyl-pyridine-2-carboxylic acid [6-((S)-5-amino-3-difluoromethyl-3,6-dihydro-2H-[1,4]oxazin-3-yl)-5-fluoro-pyridin-2-yl]-amide

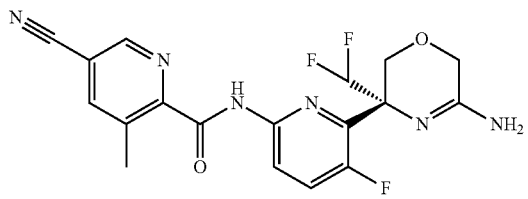 [SMILES: Cc1cc(C#N)cnc1C(=O)Nc1ccc(F)c([C@@]2(C(F)F)COCC(N)=N2)n1]

Example 39 (enantiomer of Example 38) was prepared in analogy to Example 38 with intermediate (S)-2-Methyl-propane-2-sulfinic acid [(S)-1-(6-bromo-3-fluoro-4-triethylsilylanyl-pyridin-2-yl)-2,2-difluoro-1-hydroxymethyl-ethyl]-amide from step e).

LCMS Rt$_{H4}$=0.75 min. (ESI+405); $^1$H-NMR (400 MHz, DMSO-d$_6$): 10.75 (br. s, 1H, NH), 9.02 (s, 1H), 8.44 (s, 1H), 8.20 (d, 1H), 7.78 (t, 1H), 6.36 (t, 1H, CHF$_2$), 6.06 (br. s, 2H, NH$_2$), 4.27 (d, 1H, AB), 4.04-3.86 (m, 3H, AB), 2.61 (s, 3H).

Example 40

3-Chloro-5-cyano-pyridine-2-carboxylic acid [6-((R)-5-amino-3-difluoromethyl-3,6-dihydro-2H-[1,4]oxazin-3-yl)-5-fluoro-pyridin-2-yl]-amide Example 40 was prepared in analogy to Example 38 using Amide-2 in step m). LCMS Rt$_{H12}$=0.66 min. (ESI+ 424); $^1$H-NMR (400 MHz, DMSO-d$_6$): δ 11.22 (br. s, 1H, NH), 9.11 (s, 1H), 8.81 (s, 1H), 8.16 (dd, 1H), 7.79 (dd, 1H), 6.31 (t, 1H), 6.04 (br. s, 2H, NH$_2$), 4.29 (d, 1H, AB), 3.96 (dd, 2H), 3.87 (d, 1H, AB).

Examples 41 to 48

The compounds in Table 11 were prepared by similar procedures as described for Example 11 or Example 24 and using Acids 5, 6, 7, 8 and 9 for Examples 42, 43, 45, 47 and 48 respectively.

TABLE 11

| Example | Compound | $^1$H-NMR | MS [m/z; (M + 1)$^+$] |
|---|---|---|---|
| 41 | 3,5-Dimethyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d$_6$, 400 MHz): 10.44 (br. s, 1H, NH), 8.52 (s, 1H), 8.15 (br. d, 1H), 7.74 (dd, 1H), 5.90 (br. s, 2H, NH$_2$), 4.12 (d, 1H, AB), 3.73 (d, 1H, AB), 2.80 (s, 3H), 2.57 (s, 3H), 1.50 (s, 3H), 1.48 (s, 3H). | LCMS: Rt$_{H13}$ = 0.79; [M + 1]$^+$ = 440.2 |
| 42 | 3-Amino-5-(3-fluoro-propoxy)-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d$_6$, 400 MHz): 9.88 (br. s, 1H, NH), 8.12 (dd, 1H), 7.72 (dd, 1H), 7.57 (s, 1H), 5.90 (br s, 2H, NH$_2$), 4.68 (t, 1H), 4.56 (t, 1H), 4.42 (t, 2H), 4.12 (d, 1H, AB), 3.73 (d, 1H, AB), 2.20-2.11 (m, 2H), 1.51 (s, 3H), 1.48 (s, 3H). | LCMS: Rt$_{H4}$ = 0.91; [M + 1]$^+$ = 503.0 |

TABLE 11-continued

| Example | Compound | ¹H-NMR | MS [m/z; (M + 1)⁺] |
|---|---|---|---|
| 43 | 3-Amino-5-(2-methoxy-ethyl)-5H-pyrrolo[2,3-b]pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 10.26 (br. s, 1H, NH), 8.18 (dd, 1H), 7.74 (dd, 1H), 7.63 (d, 1H), 7.51 (br. s, 2H, NH₂), 6.58 (d, 1H), 5.92 (br. s, 2H, NH₂), 4.26 (t, 2H), 4.15 (d, 1H, AB), 3.78 (d, 1H, AB), 3.70 (t, 2H), 3.32 (s, 3H), 1.53 (s, 3H), 1.51 (s, 3H). | LCMS: Rt$_{H12}$ = 0.84; [M + 1]⁺ = 525.2 |
| 44 | 3-Amino-5-trifluoromethyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 10.24 (br. s, 1H, NH), 8.37 (s, 1H), 8.12 (dd, 1H), 7.78 (dd, 1H), 5.91 (br. s, 2H, NH₂), 4.15 (d, 1H, AB), 3.75 (d, 1H, AB), 1.52 (s, 3H), 1.51 (s, 3H). | LCMS: Rt$_{H12}$ = 0.86; [M + 1]⁺ = 496.4 |
| 45 | 3-Amino-5-(2,2-difluoro-ethyl)-5H-pyrrolo[2,3-b]pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide | (δ; DMSO-d₆, 400 MHz): 10.23 (s broad, 1H, NH), 8.14 (dd, 1H), 7.76 (dd, 1H), 7.60 (d, 1H), 7.55 (s broad, 2H, NH₂), 6.64 (d, 1H), 6.41 (tt, 1H), 5.90 (s broad, 2H, NH₂), 4.54 (td, 2H), 4.12 (d, 1H, AB), 3.75 (d, 1H, AB), 1.50 (s, 3H), 1.48 (s, 3H). | LCMS: Rt$_{H12}$ = 0.87; [M + 1]⁺ = 531.1 |
| 46 | 4-Chloro-1-difluoromethyl-1H-pyrazole-3-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide | (δ; DMSO-d₆, 400 MHz): 10.15 (br. s, 1H, NH), 8.80 (s, 1H), 8.03 (dd, 1H), 7.92 (t, 1H), 7.75 (dd, 1H), 5.88 (br. s, 2H, NH₂), 4.14 (d, 1H, AB), 3.73 (d, 1H, AB), 1.52 (s, 3H), 1.48 (s, 3H). | LCMS: Rt$_{H12}$ = 0.79; [M + 1]⁺ = 485.5-487.1 |

TABLE 11-continued

| Example | Compound | ¹H-NMR | MS [m/z; (M + 1)⁺] |
|---|---|---|---|
| 47 | 6-Chloro-1-(2,2-difluoro-ethyl)-1H-pyrrolo[3,2-b]pyridine-5-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide | (δ; DMSO-d₆, 400 MHz): 10.77 (br. s, 1H, NH), 8.37 (s, 1H), 8.17 (dd, 1H), 7.88 (d, 1H), 7.72 (dd, 1H), 6.81 (d, 1H), 6.44 (tt, 1H), 5.87 (br. s, 2H, NH₂), 4.84 (td, 2H), 4.14 (d, 1H, AB), 3.73 (d, 1H, AB), 1.52 (s, 3H), 1.49 (s, 3H). | LCMS: Rt$_{H12}$ = 0.86; [M + 1]⁺ = 549.1 |
| 48 | 6-Chloro-1-(2-methoxy-ethyl)-1H-pyrrolo[3,2-b]pyridine-5-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]-amide | (δ; DMSO-d₆, 400 MHz): 10.72 (br. s, 1H, NH), 8.30 (s, 1H), 8.17 (dd, 1H), 7.87 (d, 1H), 7.72 (dd, 1H), 6.73 (d, 1H), 5.88 (br. s, 2H, NH₂), 4.44 (t, 2H), 4.15 (d, 1H, AB), 3.74 (d, 1H, AB), 3.67 (t, 2H), 3.22 (s, 3H), 1.52 (s, 3H), 1.49 (s, 3H). | LCMS: Rt$_{H12}$ = 0.86; [M + 1]⁺ = 543.2 |

Preparation of Intermediates

The substituted acid building blocks were either commercially available or can be prepared as described in the literature e.g. DE19725802A1, Tetrahedron: Asymmetry 1999, 10(4), 679-687, or in an analogous manner, or can be prepared as described hereafter or in an analogous manner.

Acid 1: 5-Cyano-3-methyl-pyridine-2-carboxylic Acid a) 5-Bromo-3-methyl-pyridine-2-carboxylic acid tert-butyl ester To a solution of 5-bromo-3-methyl-pyridine-2-carboxylic acid (10.20 g, 47.2 mmol) and di-tert-butyldicarbonate (20.61 g, 94 mmol) in 100 ml THF were added DMAP (0.577 g). Evolution of CO₂ started immediately and the mixture was stirred for 2 h at rt. TBME and sat aq NaHCO₃ were added. The layers were separated and the organic layer washed with sat aq NaHCO₃ and brine, and dried with MgSO₄.H₂O. Chromatography on silica gel (hexanes/EtOAc 1-7%) provided the title compound as a yellow liquid.

HPLC: Rt$_{H3}$=3.018 min; ESIMS [M+H]⁺=272, 274 (1 Br); ¹H-NMR (360 MHz, CDCl₃): δ 8.59 s, 1H), 7.77 (s, 1H), 2.52 (s, 3H), 1.65 (s, 9H).

b) 5-Bromo-3-methyl-pyridine-2-carboxylic acid tert-butyl ester

A mixture of 5-bromo-3-methyl-pyridine-2-carboxylic acid tert-butyl ester (6.0 g, 22.05 mmol), Zn(CN)₂ (1.813 g, 15.43 mmol), Zn powder (0.144 g, 2.205 mmol) and Pd₂(dba)₃.CHCl₃ (0.571 g, 0.551 mmol) were suspended in 10 ml DMF under nitrogen atmosphere. tBu₃P (0.321 ml, 1.323 mmol) was added and the mixture was stirred for 5 h at 60° C. After being cooled down the mixture was diluted with TBME, filtered over celite and washed with brine three times. The crude product was purified by column chromatography on silica gel (hexanes/EtOAc 5-15%) to give the title compound as an off white solid. TLC (hexanes/EtOAc 3:1): R$_f$=0.31; HPLC: Rt$_{H3}$=2.431 min; ESIMS [M+Na]⁺=241; ¹H-NMR (360 MHz, CDCl₃): δ 8.78 (s, 1H), 7.88 (s, 1H), 2.56 (s, 3H), 1.67 (s, 9H); Ft-IR: 2231 cm⁻¹ (CN).

c) 5-cyano-3-methyl-pyridine-2-carboxylic acid

To a solution of 5-cyano-3-methyl-pyridine-2-carboxylic acid tert-butyl ester (8.50 g, 38.9 mmol) in 1,3-dimethoxybenzene (51 ml, 389 mmol) was added TFA (85 ml) and stirred for 6.5 h. The reaction mixture was diluted with toluene and evaporated. The residue was taken up in toluene and evaporated (2×). The product was crystallized from TBME/hexanes to give the title compound as a white powder. HPLC: Rt$_{H1}$=2.314 min; ESIMS [M+Na]⁺=163; ¹H-NMR (360 MHz, CDCl₃): δ 8.77 (s, 1H), 8.07 (s, 1H), 2.87 (s, 3H).

Acid 2: 5-Chloro-4,6-dideutero-3-trideuteromethyl-pyridine-2-carboxylic acid

A suspension of 500 mg (2.91 mmol) 5-chloro-3-methyl-pyridine-2-carboxylic acid (CAS Nr.: 886365-46-4) in 9 ml of D$_2$O (99.96% D) was treated with 1 ml of a 40% solution of NaOD in D$_2$O. The homogeneous solution was heated in a 100 ml Teflon vessel with a Synthos 3000 Microwave apparatus. The mixture was heated at 160° C. for 5 h and cooled down. 1H-NMR and MS analyses of the product showed that deuteration had progressed to a high degree. Only minor amounts of tetradeutero derivatives were present. The reaction mixture was acidified to pH3 with 2N HCl and extracted with EtOAc. The org. phase was dried with MgSO$_4$.H$_2$O and evaporated to give the title compound as a white solid, pure enough for further transformations.

HPLC: Rt$_{H1}$=2.820 min; ESIMS [M+H]$^+$=177 (5D); $^1$H-NMR (360 MHz, D$_2$O): δ non deuterated impurities.

Acid-3: 3-Amino-5-(2,2,2-trifluoro-ethoxy)-pyrazine-2-carboxylic acid a) 3-Amino-5-(2,2,2-trifluoro-ethoxy)-pyrazine-2-carboxylic acid methyl ester A mixture of 2,2,2-trifluorethanol (6.9 ml, 96 mmol) and cesium carbonate (1.56 g, 4.8 mmol) was stirred for 20 min, 3-amino-5-chloro-pyrazine-2-carboxylic acid methyl ester (600 mg, 3.2 mmol; GB 1248146) was added and the mixture was stirred at rt for 42 h. To complete the reaction the mixture was heated to reflux for another 3 h. Saturated aq. NH$_4$Cl was added and the mixture was extracted with EtOAc, the combined organic layers were washed with saturated aq. sodium chloride, dried with Na$_2$SO$_4$ and evaporated. The residue was purified by chromatography on silica gel (cyclohexane to cyclohexane/EtOAc 3:7) to provide the title compound as colorless solid.

HPLC: Rt$_{H4}$=0.83 min; ESIMS [M+H]$^+$=252.2; $^1$H-NMR (400 MHz, DMSO-d$_6$): δ 7.66 (s, 1H), 7.60 (br s, 2H), 5.03 (q, 2H), 3.81 (s, 3H).

b) 3-Amino-5-(2,2,2-trifluoro-ethoxy)-pyrazine-2-carboxylic acid

To a solution of 3-amino-5-(2,2,2-trifluoro-ethoxy)-pyrazine-2-carboxylic acid methyl ester (400 mg, 1.59 mmol) in 20 ml THF was added 2.5 ml (2.5 mmol) 1N sodium hydroxide and the mixture was stirred at room temperature overnight. To the mixture were added (2.39 ml, 2.39 mmol) 1N HCl after stirring for 5 min toluene was added and the solvents were evaporated to provide the title compound together with sodium chloride as an off-white solid. The mixture was used for coupling reactions without further purification.

HPLC: Rt$_{H4}$=0.71 min; ESIMS [M+H]$^+$=238.2; $^1$H NMR (400 MHz, DMSO-d$_6$): δ 7.46 (s, 1H), 4.97 (q, 2H).

Acid-4: 3-Amino-5-cyano-pyridine-2-carboxylic acid a) 5-Bromo-3-nitro-pyridine-2-carboxylic acid tert-butyl ester

To an ice cooled solution of 5-bromo-3-nitro-pyridine-2-carboxylic acid (4.84 g, 19.59 mmol, CAS 954240-89-2) in THF (59 ml) was added DMAP (239 mg, 1.96 mmol) and Boc$_2$O (5.56 g, 25.5 mmol) and the reaction mixture was heated to 60° C. for 3 h. After cooling to 0° C. half saturated aq. sodium bicarbonate was added and the mixture extracted with EtOAc. The combined organic layers were washed with water and half saturated aq. NaCl, dried with Na$_2$SO$_4$ and evaporated. The residue was purified by chromatography on silica gel (cyclohexane to cyclohexane/EtOAc 3:2) to provide the title compound as pale beige solid.

HPLC: Rt$_{H5}$=1.17 min; ESIMS [M+H]$^+$=304.1; $^1$H-NMR (600 MHz, DMSO-d$_6$): δ 9.11 (s, 1H), 8.92 (s, 1H), 1.53 (s, 9H).

b) 5-Cyano-3-nitro-pyridine-2-carboxylic acid tert-butyl ester

To a solution of 5-bromo-3-nitro-pyridine-2-carboxylic acid tert-butyl ester (888 mg, 2.93 mmol) in DMF (8.8 ml) was added zinc cyanide (206 mg, 1.76 mmol) and zinc dust (2 mg, 0.03 mmol). The mixture was purged with nitrogen (3 times) bis(tri-tert-butylphosphine)palladium(0) (150 mg, 0.293 mmol) was added and the mixture was heated to 80° C. for 4 h. After cooling to 0° C. water was added and the mixture extracted with EtOAc, the combined organic layers were washed with half saturated aq. NaCl, dried with Na$_2$SO$_4$ and evaporated. The residue was purified by chromatography on silica gel (cyclohexane to cyclohexane/EtOAc 1:4) to provide the title compound as beige solid.

HPLC: Rt$_{H5}$=1.04 min; ESIMS [M+H]$^+$=248.0; $^1$H-NMR (600 MHz, DMSO-d$_6$): δ 9.39 (s, 1H), 9.29 (s, 1H), 1.55 (s, 9H).

c) 3-Amino-5-cyano-pyridine-2-carboxylic acid tert-butyl ester

To a mixture of 5-cyano-3-nitro-pyridine-2-carboxylic acid tert-butyl ester (130 mg, 0.522 mmol) in water (3 ml) was added acetic acid (0.149 ml, 2.61 mmol), the mixture was stirred at room temperature for 20 min, sodium dithionite (454 mg, 2.61 mmol) was added and stirring was continued for 23 h. Additional sodium dithionite (182 mg, 1.043 mmol) was added and the reaction mixture stirred for another 48 h. The mixture was extracted with DCM, the combined organic layers were washed with water and saturated aq. NaCl, dried with Na$_2$SO$_4$ and evaporated to provide the title compound as yellow solid. The product was used for the next step without further purification.

HPLC: Rt$_{H4}$=0.86 min; ESIMS [M+H]$^+$=220.2; $^1$H-NMR (400 MHz, DMSO-d$_6$): δ 8.15 (d, 1H), 7.61 (d, 1H), 6.95 (br. s, 2H), 1.55 (s, 9H).

d) 3-Amino-5-cyano-pyridine-2-carboxylic acid

To a mixture of 3-amino-5-cyano-pyridine-2-carboxylic acid tert-butyl ester (60 mg, 0.274 mmol) and 1,3-dimethoxybenzene (0.358 ml, 2.74 mmol) was added dropwise within 10 min TFA (0.59 ml, 7.66 mmol) and the reaction mixture was stirred for 6 h. Toluene was added and the solvents were evaporated to provide the title compound as yellow solid. The product was used for the next step without further purification.

HPLC: Rt$_{H4}$=0.38 min; ESIMS [M+H]$^+$=164.1; $^1$H-NMR (400 MHz, DMSO-d$_6$): δ 13.05 (br. s, 1H), 8.16 (d, 1H), 7.64 (d, 1H), 7.08 (br. s, 2H).

Acid-5: 3-(Di-tert-butoxycarbonyl-amino)-5-(3-fluoro-propoxy)-pyrazine-2-carboxylic acid a) 3-(Di-tert-butoxycarbonyl-amino)-5-(3-fluoropropoxy)-pyrazine-2-carboxylic acid 3-fluoro-propyl ester About a 1:1 mixture of 3-(di-tert-butoxycarbonyl-amino)-5-(3-fluoro-propoxy)-pyrazine-2-carboxylic acid methyl ester and 3-(di-tert-butoxycarbonyl-amino)-5-(3-fluoro-propoxy)-pyrazine-2-carboxylic acid 3-fluoro-propyl ester was obtained following the procedure described for acid-3 step a).

To an ice cooled solution of this mixture (245 mg, 0.89 mmol), DIPEA (1.31 ml, 7.48 mmol) and DMAP (13 mg, 0.11 mmol) in DCM (10 ml) was added a solution of Boc$_2$O (1.05 g, 4.81 mmol) in DCM (10 ml) and the mixture was stirred and allowed to warm to r.t. overnight. After addition of water the mixture was extraced with EtOAc (3×) and the combined organic layers were washed with 0.5N HCl, saturated aq. sodium chloride, dried with Na$_2$SO$_4$ and evaporated. The residue was purified by chromatography on silica gel (cyclohexane+5% NEt$_3$ to cyclohexane+0.5% NEt$_3$/EtOAc+ 0.5% NEt$_3$ 3:7) to provide the title compound together with the 3-(di-tert-butoxycarbonyl-amino)-5-(3-fluoro-propoxy)-pyrazine-2-carboxylic acid methyl ester as yellow viscous oil. This mixture was used for the next step.

HPLC: Rt$_{H4}$=1.19 min; ESIMS [M+H]$^+$=476.3; (Me-Ester: HPLC: Rt$_{H4}$=1.15 min; ESIMS [M+H]$^+$=430.3).

b) 3-(Di-tert-butoxycarbonyl-amino)-5-(3-fluoro-propoxy)-pyrazine-2-carboxylic acid To a solution of 3-(di-tert-butoxycarbonyl-amino)-5-(3-fluoro-propoxy)-pyrazine-2-carboxylic acid 3-fluoro-propyl ester and 3-(di-tert-butoxycarbonyl-amino)-5-(3-fluoro-propoxy)-pyrazine-2-carboxylic acid methyl ester (395 mg, 0.92 mmol) in THF (10 ml) was added 0.5N LiOH (2.02 ml, 1.01 mmol) and the mixture was stirred for 5.5 h. To the reaction mixture was added 1N HCl (0.92 ml, 0.92 mmol) after stirring for 5 min toluene was added and the solvents were evaporated to provide the title compound together with lithium chloride as a light yellow solid. The mixture was used for coupling reactions without further purification.

HPLC: Rt$_{H4}$=0.98 min; ESIMS [M-Boc+H]$^+$=316.2; $^1$H NMR (400 MHz, DMSO-d$_6$): δ 8.26 (s, 1H), 4.67 (t, 1H), 4.55 (t, 1H), 4.41 (t, 2H), 2.22-2.07 (m, 2H), 1.32 (s, 18H).

Acid-6: 3-Amino-5-(2-methoxy-ethyl)-5H-pyrrolo[2,3-b]pyrazine-2-carboxylic acid a) 3-Amino-6-bromo-5-(2-methoxy-ethylamino)-pyrazine-2-carboxylic acid methyl ester To a mixture of 3-amino-5,6-dichloro-pyrazine-2-carboxylic acid methyl ester [CAS 1458-18-0] and 3-amino-6-bromo-5-chloro-pyrazine-2-carboxylic acid methyl ester [CAS 14340-25-1] (799 mg, 3 mmol) in DMF was added 2-methoxy-ethylamine (0.31 ml, 3.6 mmol) and NEt$_3$ (2.09 ml, 15 mmol) and the mixture was stirred at r.t. for 3.5 h. The reaction mixture was poured into water (150 ml) and extracted with toluene (2×150 ml). The organic layers were washed with half-saturated aq. sodium chloride, combined, dried with Na$_2$SO$_4$ and evaporated. The residue was purified by chromatography on silica gel (cyclohexane/EtOAc 100:0 to 0:100%) to provide the title compound together with 3-amino-6-chloro-5-(2-methoxy-ethylamino)-pyrazine-2-carboxylic acid methyl ester (about 1:1) as colorless solid. This mixture was used for the next step.

HPLC: Rt$_{H4}$=0.77 min; ESIMS [M+H]$^+$=305.1; (Cl-pyrazine: HPLC: Rt$_{H4}$=0.73 min; ESIMS [M+H]$^+$=261.1).

b) 3-Amino-5-(2-methoxy-ethylamino)-6-trimethyl-silanylethynyl-pyrazine-2-carboxylic acid methyl ester To a solution of ethynyl-trimethyl-silane (1.05 g, 10.7 mmol), bis(triphenylphosphine)palladium(II) chloride (150 mg, 0.214 mmol), Copper(I) iodide (41 mg, 0.214 mmol) and NEt$_3$ (2.09 ml, 14.98 mmol) in THF (17 ml) was added under an argon atmosphere a mixture (about 1:1) of 3-amino-6-bromo-5-(2-methoxy-ethylamino)-pyrazine-2-carboxylic acid methyl ester and 3-amino-6-chloro-5-(2-methoxy-ethylamino)-pyrazine-2-carboxylic acid methyl ester (651 mg, 2.14 mmol) and the mixture was heated to 80° C. for 17 h. The reaction mixture was filtered through Hyflo and the solvent evaporated. The residue was purified by chromatography on silica gel (cyclohexane to cyclohexane/EtOAc 60:40) to provide the title compound as brown solid.

HPLC: Rt$_{H4}$=1.12 min; ESIMS [M+H]$^+$=323.3; $^1$H NMR (400 MHz, DMSO-d$_6$): δ 7.46 (br, 2H), 6.65 (t, 1H), 3.73 (s, 3H), 3.59-3.45 (m, 4H), 3.28 (s, 3H), 0.25 (s, 9H).

c) 3-Amino-5-(2-methoxy-ethyl)-5H-pyrrolo[2,3-b]pyrazine-2-carboxylic acid

To a solution of 3-amino-5-(2-methoxy-ethylamino)-6-trimethylsilanylethynyl-pyrazine-2-carboxylic acid methyl ester (487 mg, 1.51 mmol) in THF (7.6 ml) was added a suspension of KOtBu (356 mg, 3.17 mmol) in THF (7.6 ml) and the reaction mixture was stirred at r.t. for 2 h. At 0° C. solid NH$_4$Cl (848 mg) was added and the mixture stirred for 30 min. After addition of half-saturated NH$_4$Cl solution (15 ml) the mixture was extracted with EtOAc (2×15 ml), the pH of the aq. phase was adjusted the pH to 4 by addition of 1N HCl. The aq. phase was extracted with DCM/EtOH 9:1 (2×100 ml), the combined organic layers were dried with Na$_2$SO$_4$ and evaporated. The residue was filtered through a plug of silica gel (DCM/EtOH 90:10) to provide the title compound as brown powder. This material was used for coupling reactions without further purification.

HPLC: Rt$_{H4}$=0.53 min; ESIMS [M+H]$^+$=237.1; $^1$H NMR (600 MHz, DMSO-d$_6$): δ 12.59 (br s, 1H), 7.55 (d, 1H), 7.26 (br s, 2H), 6.46 (d, 1H), 4.21 (t, 2H), 3.66 (t, 2H), 3.22 (s, 3H).

Acid-7: 3-Amino-5-(2,2-difluor-ethyl)-5H-pyrrolo[2,3-b]pyrazine-2-carboxylic acid 3-Amino-5-(2,2-difluoro-ethylamino)-6-trimethylsilanyl-ethynyl-pyrazine-2-carboxylic acid methyl ester was prepared by similar procedures as for Acid-6 (steps a and b) applying 80° C. in step a) instead of room temperature.

a) 3-Amino-5-(2,2-difluoro-ethyl)-6H-pyrrolo[2,3-b]pyrazine-2-carboxylic acid methyl ester To a solution of 3-amino-5-(2,2-difluoro-ethylamino)-6-trimethylsilanylethynyl-pyrazine-2-carboxylic acid methyl ester (624 mg, 1.9 mmol) in DMF (19 ml) was added Copper(I) iodide (181 mg, 0.95 mmol) and the mixture was heated to 120° C. for 2 h. The reaction mixture was filtered through Hyflo, the residue washed with toluene. The combined organic phases were extracted with water, dried with Na$_2$SO$_4$ and evaporated. The residue was purified by chromatography on silica gel (cyclohexane to cyclohexane/EtOAc 40:60) to provide the title compound as yellow solid.

HPLC: Rt$_{H4}$=0.67 min; ESIMS [M+H]$^+$=257.1; $^1$H NMR (400 MHz, DMSO-d$_6$): δ 7.64-7.51 (m, 1H), 7.27 (br s, 2H), 6.56 (m, 1H), 6.43 (t, 1H), 4.62-4.46 (m, 2H), 3.86 (s, 3H).

b) 3-Amino-5-(2,2-difluor-ethyl)-5H-pyrrolo[2,3-b]pyrazine-2-carboxylic acid

To a solution of 3-amino-5-(2,2-difluoro-ethyl)-6H-pyrrolo[2,3-b]pyrazine-2-carboxylic acid methyl ester (192 mg, 0.749 mmol) in THF (3.8 ml) was added a solution of 1M LiOH (0.824 ml, 0.824 mmol) and the reaction mixture was stirred at r.t. for 20 h. At 0° C. 1M HCl (0.749 ml) was added and the mixture diluted with toluene (7.5 ml). The solvents were evaporated to provide the title compound together with LiCl as brown powder. This material was used for coupling reactions without further purification.

HPLC: $Rt_{H4}$=0.57 min; ESIMS [M+H]$^+$=243.1; $^1$H NMR (600 MHz, DMSO-d$_6$): δ 12.71 (br s, 1H), 7.56 (d, 1H), 7.35 (br s, 2H), 6.55 (d, 1H), 6.41 (t, 1H), 4.61-4.43 (m, 2H).

Acid-8: 6-Chloro-1-(2,2-difluoro-ethyl)-1H-pyrrolo[3,2-b]pyridine-5-carboxylic acid a) 6-Chloro-1-(2,2-difluoro-ethyl)-1H-pyrrolo[3,2-b]pyridine-5-carboxylic acid ethyl ester To a solution of 6-chloro-1H-pyrrolo[3,2-b]pyridine-5-carboxylic acid ethyl ester (210 mg, 0.935 mmol) in DMF (10 ml) was added cesium carbonate (457 mg, 1.402 mmol), after 15 min stirring at room temperature 1,1-difluoro-2-iodoethane (538 mg, 2.8 mmol) was added and stirring was continued over night. Tetrabutylammonium iodide (34.5 mg, 0.093 mmol) was added and stirring was continued for another 48 h. To the reaction mixture was added saturated aq. NH4Cl and the mixture was extracted with MTBE (2×). The combined organic layers were washed with half-saturated aq. NaCl, dried with Na$_2$SO$_4$ and evaporated. The residue was purified by chromatography on silica gel (cyclohexane to cyclohexane/EtOAc 20:80) to provide the title compound as yellow solid.

HPLC: $Rt_{H4}$=0.88 min; ESIMS [M+H]$^+$=289.4/291.1; $^1$H NMR (400 MHz, DMSO-d$_6$): δ 8.34 (s, 1H), 7.83 (d, 1H), 6.74 (d, 1H), 6.40 (t, 1H), 4.78 (td, 2H), 4.35 (q, 2H), 1.31 (t, 3H).

b) 6-Chloro-1-(2,2-difluoro-ethyl)-1H-pyrrolo[3,2-b]pyridine-5-carboxylic acid

To a solution of 6-chloro-1-(2,2-difluoro-ethyl)-1H-pyrrolo[3,2-b]pyridine-5-carboxylic acid ethyl ester (150 mg, 0.520 mmol) in THF (10 ml) was added 1N aq. sodium hydroxide (0.624 ml, 0.624 mmol) and mixture was stirred at 65° C. for 4.5 h. The solvents were evaporated, the residue was dissolved in water, acidified with 2N aq. HCl and the mixture extracted with EtOAc. The combined organic layers were dried with Na$_2$SO$_4$ and evaporated to provide the title compound as light orange solid.

HPLC: $Rt_{H4}$=0.50 min; ESIMS [M+H]$^+$=261.0/263.1; $^1$H NMR (400 MHz, DMSO-d$_6$): δ 13.36 (s, 1H), 8.31 (s, 1H), 7.81 (d, 1H), 6.72 (d, 1H), 6.39 (t, 1H), 4.87-4.67 (m, 2H).

Acid-9: 6-Chloro-1-(2-methoxy-ethyl)-1H-pyrrolo[3,2-b]pyridine-5-carboxylic acid 6-Chloro-1-(2-methoxy-ethyl)-1H-pyrrolo[3,2-b]pyridine-5-carboxylic acid was prepared by similar procedures as for Acid-9 [steps a) and b)] using 1-bromo-2-methoxy-ethane in step a) instead of 1,1-difluoro-2-iodo-ethane without addition of tetrabutylammonium iodide and stirring only once over night.

HPLC: $Rt_{H4}$=0.47 min; ESIMS [M+H]$^+$=255.1/257.1; $^1$H NMR (400 MHz, DMSO-d$_6$): δ 13.26 (br. s, 1H), 8.22 (s, 1H), 7.79 (d, 1H), 6.63 (d, 1H), 4.38 (t, 2H), 3.62 (t, 2H), 3.17 (s, 3H).

Amide 1: 5-Cyano-3-methyl-pyridine-2-carboxylic acid amide

To a white suspension of 5-cyano-3-methyl-pyridine-2-carboxylic acid (84 mg, 0.518 mmol) in DCM (1.5 ml) was added oxalyl chloride (0.068 ml, 99 mg, 0.777 mmol) and a catalytic amount of DMF. The reaction mixture was stirred at rt for 1 h and was then added dropwise to a 25% aq. NH$_4$OH soln. (0.300 ml) at 0° C. The reaction mixture was stirred for 10 min at rt, H$_2$O and TBME were added, the phases were separated and the aq. phase was twice reextracted with TBME. The combined org. phases were dried over Na$_2$SO$_4$, filtered and concentrated to leave a white powder that was used in the next step without further purification. $Rt_{H4}$=0.47 min; ESIMS: 162 [(M+H)$^+$]; $^1$H NMR (400 MHz, DMSO-d$_6$): δ 8.68 (d, 1H), 7.91 (d, 1H), 7.80 (br s, 1H), 5.57 (br s, 1H), 2.80 (s, 3H).

Amide 2: 3-Chloro-5-cyano-pyridine-2-carboxylic acid amide was prepared from 3-chloro-5-cyano-pyridine-2-carboxylic acid (CAS 1200497-81-9) in analogy to the procedure described for Amide 1.

$Rt_{H4}$=0.45 min;
$^1$H NMR (400 MHz, DMSO-d$_6$): δ 9.01 (d, 1H), 8.70 (d, 1H), 8.17 (br s, 1H), 7.94 (br s, 1H).

Amide 3: 3-Chloro-5-difluoromethoxy-pyridine-2-carboxylic acid amide was prepared from 3-chloro-5-difluoromethoxy-pyridine-2-carboxylic acid (CAS 1262860-72-9) in analogy to above procedure. $Rt_{H4}$=0.62 min; ESIMS: 223 [(M+H)$^+$];
$^1$H NMR (400 MHz, DMSO-d$_6$): δ 8.49 (d, 1H), 8.08-7.97 (m, 2H), 7.73 (br s, 1H), 7.45 (t, 1H).

Hydroxyester 1:
3-Fluoro-2-fluoromethyl-2-hydroxy-propionic acid ethyl ester a) 3-Fluoro-2-fluoromethyl-2-trimethylsilanyloxy-propionitrile To 1,3-difluoro-propan-2-one (8.5 g, 90 mmol) was added drop wise over 30 min TMS-Cyanide (8.97 g, 90 mmol). The reaction mixture was stirred for 16 h at ambient temperature. Yield=17.4 g (100%).
$^1$H-NMR (400 MHz, CDCl$_3$) δ 4.55 (d, 2H), 4.44 (d, 2H), 0.28 (s, 9H).
$^{19}$F-NMR (376 MHz, CDCl$_3$) δ-226 (t).

b) 3-Fluoro-2-fluoromethyl-2-hydroxy-propionic acid

3-Fluoro-2-fluoromethyl-2-trimethylsilanyloxy-propionitrile (17.4 g, 90 mmol) was treated with 37% HCl (300 ml) and heated to gentle reflux for 3 h. The reaction mixture was cooled to ambient temperature and concentrated in vacuo. The solid thus obtained was redisolved in 300 ml ethanol and concentrated in vacuo and dried in high vacuum.

The solid thus obtained (17 g) contained significant amount of ammonium-chloride and was used without further purification.
$^1$H-NMR (400 MHz, DMSO-d$_6$) δ 7.0-7.3 (m, 4H), 5.6-6.5 (s, 1H), 4.43-4.58 (m, 4H).
$^{13}$C-NMR (150 MHz, DMSO-d$_6$) δ 171(t), 85 (d), 83 (d), 75 (t).

c) 3-Fluoro-2-fluoromethyl-2-hydroxy-propionic acid ethyl ester

Crude 3-fluoro-2-fluoromethyl-2-hydroxy-propionic acid (17 g) was dissolved in ethanol (400 ml) and H$_2$SO$_4$ (98%, 30 g) was added. The reaction mixture was refluxed for 16 h. The reaction mixture was cooled to ambient temperature and filtered. The solution was carefully treated with 30 g solid $Na_2CO_3$ and the resulting mixture was stirred for 30 min at room temperature. 400 ml DCM were added and the mixture was filtered. The solution was concentrated (50° C., 150 mbar) and further purified by distillation (82° C., 20 mbar) to give a colorless liquid.

Yield=9.8 g (97%).

$^1$H-NMR (400 MHz, DMSO-$d_6$) δ 4.43-4.65 (m, 4H), 4.30 (q, 2H), 3.63-3.88 (s, 1H), 1.30 (t, 3H).

The invention claimed is:

1. A compound of formula (I), or a pharmaceutically acceptable salt thereof,

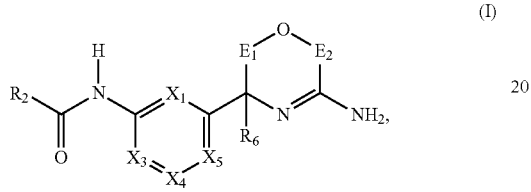

(I)

in which
either
  $X_1$ is $CR_1$ or N;
  $X_3$ is $CR_3$ or N;
  $X_4$ is $CR_4$ or N;
  $X_5$ is $CR_5$ or N;
  wherein at least one of $X_1$, $X_3$, $X_4$ and $X_5$ is N and not more than 2 of $X_1$, $X_3$, $X_4$ and $X_5$ are N;
or
  $X_1$ is $CR_1$ or N;
  $X_3$ is $CR_3$, N or S;
  $X_4$ is a bond;
  $X_5$ is $CR_5$, N or S;
  wherein at least one of $X_1$, $X_3$ and $X_5$ is N or S, not more than 2 of $X_1$, $X_3$ and $X_5$ are N and not more than 1 of $X_3$ and $X_5$ are S;
$R_1$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;
$R_2$ is an aryl, heteroaryl or non-aromatic heterocyclyl group $G_1$, which group $G_1$ is optionally substituted by 1, 2, 3 or 4 substituents independently selected from the group, consisting of cyano, amino, amino-$(C_{1-8})$alkyl, N—$(C_{1-4})$alkyl-amino-$(C_{1-8})$alkyl, N,N-di$(C_{1-4})$alkyl-amino-$(C_{1-8})$alkyl, aminocarbonyl, thiocarbamoyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{3-8})$cycloalkyl-$(C_{1-8})$alkoxy, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3, or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

$R_3$ is hydrogen, cyano, halogen, $(C_{1-8})$alkyl, halogen-$(C_{1-8})$alkyl, $(C_{1-8})$alkoxy; halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_4$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_5$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

or $R_4$ and $R_5$, taken together, are —C(H)=C(H)—C(H)=C(H)— or a $(C_{1-8})$alkylene group, in which $(C_{1-8})$ alkylene group 1 or 2 —$CH_2$— ring members are optionally replaced with hetero ring members independently selected from the group, consisting of —N(H)—, —N[$(C_{1-8})$alkyl]-, —O—, —S—, —S(=O)— or —S(=O)$_2$—;

$R_6$ is $(C_{1-8})$alkyl, halogen-$(C_{1-8})$alkyl, hydroxy-$(C_{1-8})$alkyl, $(C_{1-8})$alkoxy-$(C_{1-8})$alkyl, mercapto-$(C_{1-8})$alkyl, $(C_{1-8})$alkylthio-$(C_{1-8})$alkyl, amino-$(C_{1-8})$alkyl, N—$(C_{1-4})$alkyl-amino-$(C_{1-8})$alkyl, N,N-di$(C_{1-4})$alkyl-amino-$(C_{1-8})$alkyl, $(C_{2-8})$alkenyl, or $(C_{2-8})$alkynyl;

or $R_5$ and $R_6$, taken together, are a $(C_{1-4})$alkylene group, in which $(C_{1-4})$alkylene group 1 —$CH_2$— ring member is optionally replaced with a hetero ring member independently selected from the group, consisting of —N(H)—, —O—, —S—, —S(=O)— or —S(=O)$_2$—;

$E_1$ is —C($R_7$)($R_8$)—, or —C($R_7$)($R_8$)—C($R_9$)($R_{10}$)—;
$E_2$ is —C($R_{11}$)($R_{12}$)—, or —C($R_{11}$)($R_{12}$)—C($R_{13}$)($R_{14}$)—;

either
each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_7$ and $R_8$, taken together, are oxo or —$CH_2$—$CH_2$—;

either
each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_9$ and $R_{10}$, taken together, are oxo or —$CH_2$—$CH_2$—;

either each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{11}$ and $R_{12}$, taken together, are oxo or —$CR_{15}R_{16}$—$CR_{17}R_{18}$—
wherein $R_{15}$, $R_{16}$, $R_{17}$ and $R_{18}$ are independently selected from hydrogen and fluoro; and
either
each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{13}$ and $R_{14}$, taken together, are oxo or —$CH_2$—$CH_2$—.

2. The compound of claim 1, or a pharmaceutically acceptable salt thereof, wherein $R_1$ is hydrogen.

3. The compound of claim 1, or a pharmaceutically acceptable salt thereof, wherein $R_2$ is a 5- or 6-membered heteroaryl group in which structure 1, 2, 3, or 4 ring members are hetero ring members independently selected from the group consisting of a nitrogen ring member, an oxygen ring member and a sulfur ring member, which group is optionally substituted by 1, 2, 3 or 4 substituents independently selected from the group, consisting of cyano, amino, aminocarbonyl, thiocarbamoyl, halogen, $(C_{1-4})$alkyl, halogen-$(C_{1-4}$alkyl, hydroxy, oxo, $(C_{1-4})$alkoxy, halogen-$(C_{1-4})$alkoxy, $(C_{1-4})$alkylthio, halogen-$(C_{1-4})$alkylthio, $(C_{1-4})$alkoxy-$(C_{1-4})$alkyl, $(C_{1-4})$alkoxy-$(C_{1-4})$alkoxy, $(C_{1-4})$alkoxy-$(C_{1-4})$alkylthio, $(C_{1-4})$alkylthio-$(C_{1-4})$alkyl, $(C_{1-4})$alkylthio-$(C_{1-4})$alkoxy, $(C_{1-4})$alkylthio-$(C_{1-4})$alkylthio, $(C_{2-4})$alkenyl, $(C_{2-4})$alkynyl, $(C_{2-4})$alkenoxy, and $(C_{2-4})$alkynoxy.

4. The compound of claim 1, or a pharmaceutically acceptable salt thereof, wherein $R_3$ is hydrogen.

5. The compound of claim 1, or a pharmaceutically acceptable salt thereof, wherein
$X_1$ is CH or N;
$X_3$ is CH or N;
$X_4$ is $CR_4$ or N;
$X_5$ is $CR_5$;
wherein one and not more than one of $X_1$, $X_3$ and $X_4$ is N.

6. The compound of claim 1, or a pharmaceutically acceptable salt thereof, wherein $R_4$ is hydrogen, or halogen; and $R_5$ is hydrogen, or halogen.

7. The compound of claim 1, or a pharmaceutically acceptable salt thereof, wherein $R_6$ is $(C_{1-3})$alkyl, or halogen-$(C_{1-3})$alkyl.

8. The compound of claim 1, or a pharmaceutically acceptable salt thereof, wherein $E_1$ is —$C(R_7)(R_8)$— and
either
each of $R_7$ and $R_8$ is hydrogen;
or
$R_7$ and $R_8$, taken together, are oxo.

9. The compound of claim 1, or a pharmaceutically acceptable salt thereof,
wherein $E_2$ is —$C(R_{11})(R_{12})$— and either
each of $R_{11}$ and $R_{12}$ is independently selected from the group, consisting of hydrogen, $(C_{1-3})$alkyl and halogen-$(C_{1-3})$alkyl;
or
$R_{11}$ and $R_{12}$, taken together, are oxo.

10. The compound of claim 1, or a pharmaceutically acceptable salt thereof, which is selected from the group consisting of:

5-Bromo-pyridine-2-carboxylic acid [6-(5-amino-3-methyl-3,6-dihydro-2H-[1,4]-oxazin-3-yl)-pyridin-2-yl]-amide;
5-Chloro-pyridine-2-carboxylic acid [6-(5-amino-3-fluoromethyl-3,6-dihydro-2H-[1,4]oxazin-3-yl)-pyridin-2-yl]-amide;
5-Bromo-pyridine-2-carboxylic acid [6-(5-amino-3-fluoromethyl-3,6-dihydro-2H-[1,4]oxazin-3-yl)-pyridin-2-yl]-amide;
5-Cyano-3-methyl-pyridine-2-carboxylic acid [6-(5-amino-3-fluoromethyl-3,6-dihydro-2H-[1,4]oxazin-3-yl)-pyridin-2-yl]-amide;
4,6-Dideutero-5-chloro-3-trideuteromethyl-pyridine-2-carboxylic acid [6-(5-amino-3-fluoromethyl-3,6-dihydro-2H-[1,4]oxazin-3-yl)-pyridin-2-yl]-amide;
5-Thiocarbamoyl-pyridine-2-carboxylic acid [6-(5-amino-3-fluoromethyl-3,6-dihydro-2H-[1,4]oxazin-3-yl)-pyridin-2-yl]-amide;
5-Cyano-3-methyl-pyridine-2-carboxylic acid [6-(5-amino-3,6-dimethyl-6-trifluoro-methyl-3,6-dihydro-2H-[1,4]oxazin-3-yl)-pyridin-2-yl]-amide;
5-Cyano-pyridine-2-carboxylic acid [6-(5-amino-3,6-dimethyl-6-trifluoromethyl-3,6-dihydro-2H-[1,4]oxazin-3-yl)-pyridin-2-yl]-amide;
5-Cyano-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]-amide;
4,6-Dideutero-5-chloro-3-trideuteromethyl-pyridine-2-carboxylic acid [4-(5-amino-3-fluoromethyl-3,6-dihydro-2H-[1,4]oxazin-3-yl)-pyridin-2-yl]-amide;
5-Chloro-pyridine-2-carboxylic acid [4-(5-amino-3-fluoromethyl-3,6-dihydro-2H-[1,4]oxazin-3-yl)-pyridin-2-yl]-amide;
5-Cyano-3-methyl-pyridine-2-carboxylic acid [4-(5-amino-3,6-dimethyl-6-trifluoromethyl-3,6-dihydro-2H-[1,4]oxazin-3-yl)-5-fluoro-pyridin-2-yl]-amide;
5-Bromo-pyridine-2-carboxylic acid [5-(5-amino-3-fluoromethyl-3,6-dihydro-2H-[1,4]oxazin-3-yl)-6-chloro-pyridin-3-yl]-amide;
3-Amino-5-cyano-pyridine-2-carboxylic acid [6-(5-amino-3,6-dimethyl-6-trifluoromethyl-3,6-dihydro-2H-[1,4]oxazin-3-yl)-pyridin-2-yl]-amide;
3-Chloro-5-cyano-pyridine-2-carboxylic acid [6-(5-amino-3,6-dimethyl-6-trifluoromethyl-3,6-dihydro-2H-[1,4]oxazin-3-yl)-pyridin-2-yl]-amide;
5-Chloro-4,6-dideuterio-3-trideuteriomethyl-pyridine-2-carboxylic acid [6-(5-amino-3,6-dimethyl-6-trifluoromethyl-3,6-dihydro-2H-[1,4]oxazin-3-yl)-pyridin-2-yl]-amide;
5-Bromo-3-chloro-pyridine-2-carboxylic acid [6-(5-amino-3,6-dimethyl-6-trifluoromethyl-3,6-dihydro-2H-[1,4]oxazin-3-yl)-pyridin-2-yl]-amide;
3-Amino-5-(2,2,2-trifluoro-ethoxy)-pyrazine-2-carboxylic acid [6-(5-amino-3,6-dimethyl-6-trifluoromethyl-3,6-dihydro-2H-[1,4]oxazin-3-yl)-pyridin-2-yl]amide;
3-Chloro-5-cyano-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]-amide;
5-Methoxy-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;
3-Amino-5-(2,2,2-trifluoro-ethoxy)-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl] amide;

3-Amino-5-cyano-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

5-Difluoromethoxy-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Chloro-5-difluoromethoxy-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3,5-Dichloro-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

5-Fluoromethoxy-3-methyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

5-Methyl-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Chloro-5-trifluoromethyl-pyridine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Chloro-5-cyano-pyridine-2-carboxylic acid [4-(5-amino-3,6-dimethyl-6-trifluoromethyl-3,6-dihydro-2H-[1,4]oxazin-3-yl)-5-fluoro-pyridin-2-yl]-amide;

3-Chloro-5-difluoromethoxy-pyridine-2-carboxylic acid [4-(5-amino-3,6-dimethyl-6-trifluoromethyl-3,6-dihydro-2H-[1,4]oxazin-3-yl)-5-fluoro-pyridin-2-yl]-amide;

5-Cyano-3-methyl-pyridine-2-carboxylic acid [4-(5-amino-6,6-bis-fluoromethyl-3-methyl-3,6-dihydro-2H-[1,4]oxazin-3-yl)-5-fluoro-pyridin-2-yl]-amide;

5-Cyano-3-methyl-pyridine-2-carboxylic acid [6-(5-amino-3-difluoromethyl-3,6-dihydro-2H-[1,4]oxazin-3-yl)-5-fluoro-pyridin-2-yl]amide;

3-Chloro-5-cyano-pyridine-2-carboxylic acid [6-(5-amino-3-difluoromethyl-3,6-dihydro-2H-[1,4]oxazin-3-yl)-5-fluoro-pyridin-2-yl]amide;

3,5-Dimethyl-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Amino-5-(3-fluoro-propoxy)-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Amino-5-(2-methoxy-ethyl)-5H-pyrrolo[2,3-b]pyrazine-2-carboxylic acid [6-((5-amino-3,6-dimethyl-6-trifluoromethyl-3,6-dihydro-2H-[1,4]oxazin-3-yl)-5-fluoro-pyridin-2-yl]amide;

3-Amino-5-trifluoromethyl-pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]amide;

3-Amino-5-(2,2-difluoro-ethyl)-5H-pyrrolo[2,3-b]pyrazine-2-carboxylic acid [6-(5-amino-3,6-dimethyl-6-trifluoromethyl-3,6-dihydro-2H-[1,4]oxazin-3-yl)-5-fluoro-pyridin-2-yl]-amide;

4-Chloro-1-difluoromethyl-1H-pyrazole-3-carboxylic acid [6-(5-amino-3,6-dimethyl-6-trifluoromethyl-3,6-dihydro-2H-[1,4]oxazin-3-yl)-5-fluoro-pyridin-2-yl]-amide;

6-Chloro-1-(2,2-difluoro-ethyl)-1H-pyrrolo[3,2-b]pyridine-5-carboxylic acid [6-(5-amino-3,6-dimethyl-6-trifluoromethyl-3,6-dihydro-2H-[1,4]oxazin-3-yl)-5-fluoro-pyridin-2-yl]-amide; and 6-Chloro-1-(2-methoxy-ethyl)-1H-pyrrolo[3,2-b]pyridine-5-carboxylic acid [6-(5-amino-3,6-dimethyl-6-trifluoromethyl-3,6-dihydro-2H-[1,4]oxazin-3-yl)-5-fluoro-pyridin-2-yl]-amide.

11. A pharmaceutical composition comprising a compound of claim 1, or a pharmaceutically acceptable salt thereof, as active pharmaceutical ingredient in association with at least one pharmaceutically acceptable carrier or diluent.

12. A pharmaceutical combination comprising a therapeutically effective amount of a compound of claim 1, or a pharmaceutically acceptable salt thereof, and a second drug substance, for simultaneous or sequential administration.

13. A compound of formula (I), or a pharmaceutically acceptable salt thereof,

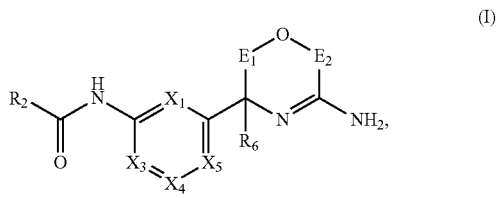

(I)

in which $X_1$ is $CR_1$ or N;

$X_3$ is $CR_3$ or N;

$X_4$ is $CR_4$ or N;

$X_5$ is $CR_5$ or N;

wherein at least one of $X_1$, $X_3$, $X_4$ and $X_5$ is N and not more than 2 of $X_1$, $X_3$, $X_4$ and $X_5$ are N;

$R_1$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_2$ is an aryl, heteroaryl or non-aromatic heterocyclyl group $G_1$, which group $G_1$ is optionally substituted by 1, 2, 3 or 4 substituents independently selected from the group, consisting of cyano, amino, amino-$(C_{1-8})$alkyl, aminocarbonyl, thiocarbamoyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{3-8})$cycloalkyl-$(C_{1-8})$alkoxy, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3, or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

$R_3$ is hydrogen, cyano, halogen, $(C_{1-8})$alkyl, halogen-$(C_{1-8})$alkyl, $(C_{1-8})$alkoxy; halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_4$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

$R_5$ is hydrogen, cyano, halogen, $(C_{1-8})$alkyl, halogen-$(C_{1-8})$alkyl, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, or $(C_{2-8})$alkynyl;

or $R_4$ and $R_5$, taken together, are —C(H)═C(H)—C(H)═C(H)— or a $(C_{1-8})$alkylene group, in which $(C_{1-8})$alkylene group 1 or 2 —CH$_2$— ring members are optionally replaced with hetero ring members independently selected from the group, consisting of —N(H)—, —N[$(C_{1-8})$alkyl]-, —O—, —S—, —S(═O)— or —S(═O)—;

$R_6$ is $(C_{1-8})$alkyl, halogen-$(C_{1-8})$alkyl, hydroxy-$(C_{1-8})$alkyl, $(C_{1-8})$alkoxy-$(C_{1-8})$alkyl, mercapto-$(C_{1-8})$alkyl, $(C_{1-8})$alkylthio-$(C_{1-8})$alkyl, amino-$(C_{1-8})$alkyl, N—$(C_{1-4}$alkyl-amino-$(C_{1-8})$alkyl, $(C_{2-8})$alkenyl, or $(C_{2-8})$alkynyl;

or $R_5$ and $R_6$, taken together, are a $(C_{1-4})$alkylene group, in which $(C_{1-4})$alkylene group 1 —CH$_2$— ring member is optionally replaced with a hetero ring member independently selected from the group, consisting of —N(H)—, —O—, —S—, —S(═O)— or —S(═O)$_2$—;

$E_1$ is —C($R_7$)($R_8$)—, or —C($R_7$)($R_8$)—C($R_9$)($R_{10}$)—;
$E_2$ is —C($R_{11}$)($R_{12}$)—, or —C($R_{11}$)($R_{12}$)—C($R_{13}$)($R_{14}$)—;

either each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_7$ and $R_8$, taken together, are oxo or —CH$_2$—CH$_2$—;
either each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_9$ and $R_{10}$, taken together, are oxo or —CH$_2$—CH$_2$—;
either each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_{11}$ and $R_{12}$, taken together, are oxo or —CR$_{15}$R$_{16}$—CR$_{17}$R$_{18}$—
wherein $R_{15}$, $R_{16}$, $R_{17}$ and $R_{18}$ are independently selected from hydrogen and fluoro; and
either each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or $R_{13}$ and $R_{14}$, taken together, are oxo or —CH$_2$—CH$_2$—.

14. The compound of claim 13, or a pharmaceutically acceptable salt thereof, having formula (Id)

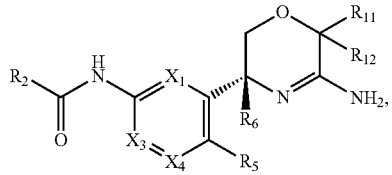

in which
$X_1$ is CH or N;
$X_3$ is CH or N;
$X_4$ is CR$_4$ or N;
wherein one and not more than one of $X_1$, $X_3$ and $X_4$ is N;

$R_2$ is a pyridyl or pyrazinyl group which is substituted by 2 or 3 substituents and wherein one of the substituents is located at the para position and one of the substituents is located at the ortho position of the pyridyl or pyrazinyl group relative to the amide linker and wherein the substituents are independently selected from the group, consisting of cyano, amino, halogen, $(C_{1-4})$alkyl, halogen-$(C_{1-4}$alkyl, hydroxy, oxo, $(C_{1-4})$alkoxy and halogen-$(C_{1-4}$alkoxy;

$R_4$ and $R_5$ are independently hydrogen, or halogen;
$R_6$ is methyl, fluoromethyl, difluoromethyl or trifluoromethyl; and
each of $R_{11}$ and $R_{12}$ is independently selected from the group, consisting of hydrogen, methyl, fluoromethyl, difluoromethyl and trifluoromethyl.

15. The compound of claim 14, or a pharmaceutically acceptable salt thereof, having formula (Ie)

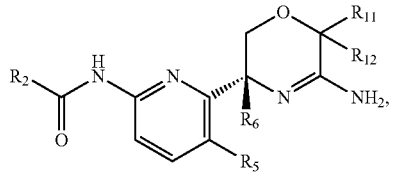

in which
$R_2$ is a pyridin-2-yl or pyrazin-2-yl group which is substituted by 2 substituents and wherein one of the substituents is located at the para position and one of the substituents is located at the ortho position of the pyridin-2-yl or pyrazin-2-yl group relative to the amide linker and wherein the substituents are independently selected from the group, consisting of cyano, amino, fluoro, bromo, chloro, hydroxyl, oxo, methyl, fluoromethyl, difluoromethyl, trifluoromethyl, methoxy, fluoromethoxy, difluoromethoxy and trifluoromethoxy;

$R_5$ is hydrogen or fluoro;
$R_6$ is methyl, fluoromethyl or difluoromethyl; and
each of $R_{11}$ and $R_{12}$ is independently selected from the group, consisting of hydrogen, methyl, fluoromethyl, difluoromethyl and trifluoromethyl;

or a pharmaceutically acceptable salt thereof.

16. The compound of claim 15, or a pharmaceutically acceptable salt thereof, wherein $R_5$ is fluoro.

17. The compound 3-chloro-5-trifluoromethyl-pyridine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide, or a pharmaceutically acceptable salt thereof, having the formula

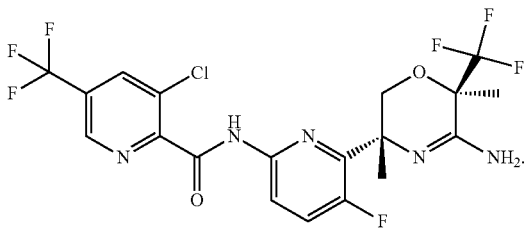 [SMILES: C[C@@]1(c2nc(NC(=O)c3ncc(C(F)(F)F)cc3Cl)ccc2F)CO[C@@](C)(C(F)(F)F)C(N)=N1]

18. A pharmaceutical composition comprising a compound of claim 17, or a pharmaceutically acceptable salt thereof, as active pharmaceutical ingredient in association with at least one pharmaceutically acceptable carrier or diluent.

19. A pharmaceutical combination comprising a therapeutically effective amount of a compound of claim 17, or a pharmaceutically acceptable salt thereof, and a second drug substance, for simultaneous or sequential administration.

20. The compound 3-chloro-5-cyano-pyridine-2-carboxylic acid [6-((3S,6R)-5-amino-3,6-dimethyl-6-trifluoromethyl-3,6-dihydro-2H-[1,4]oxazin-3-yl)-5-fluoro-pyridin-2-yl]amide, or a pharmaceutically acceptable salt thereof, having the formula

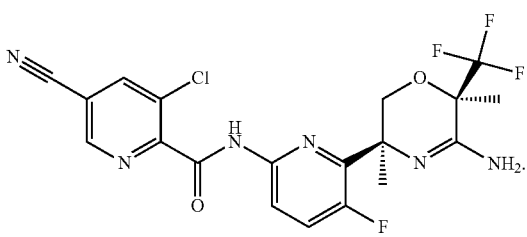 [SMILES: C[C@]1(c2nc(NC(=O)c3ncc(C#N)cc3Cl)ccc2F)CO[C@@](C)(C(F)(F)F)C(N)=N1]

21. A pharmaceutical composition comprising a compound of claim 20, or a pharmaceutically acceptable salt thereof, as active pharmaceutical ingredient in association with at least one pharmaceutically acceptable carrier or diluent.

22. A pharmaceutical combination comprising a therapeutically effective amount of a compound of claim 20, or a pharmaceutically acceptable salt thereof, and a second drug substance, for simultaneous or sequential administration.

23. The compound 3-amino-5-trifluoromethyl-pyrazine-2-carboxylic acid [6-((3R,6R)-5-amino-3,6-dimethyl-6-trifluoromethyl-3,6-dihydro-2H-[1,4]oxazin-3-yl)-5-fluoro-pyridin-2-yl]amide, or a pharmaceutically acceptable salt thereof, having the formula

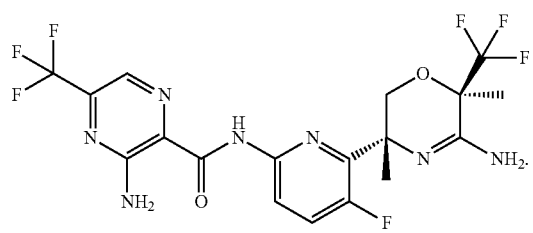 [SMILES: C[C@@]1(c2nc(NC(=O)c3ncc(C(F)(F)F)nc3N)ccc2F)CO[C@@](C)(C(F)(F)F)C(N)=N1]

24. A pharmaceutical composition comprising a compound of claim 23, or a pharmaceutically acceptable salt thereof, as active pharmaceutical ingredient in association with at least one pharmaceutically acceptable carrier or diluent.

25. A pharmaceutical combination comprising a therapeutically effective amount of a compound of claim 23, or a pharmaceutically acceptable salt thereof, and a second drug substance, for simultaneous or sequential administration.

* * * * *